(12) United States Patent
Mukumoto et al.

(10) Patent No.: US 6,410,293 B1
(45) Date of Patent: Jun. 25, 2002

(54) DNA FRAGMENTS CONTAINING BIOTIN BIOSYNTHETASE GENE AND USE OF THE SAME

(75) Inventors: Fujio Mukumoto; Shoichi Nishio, both of Toyonaka; Jiro Akimaru, Nishinomiya; Satoshi Mitsuda, Takarazuka, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/180,109

(22) PCT Filed: Mar. 2, 1998

(86) PCT No.: PCT/JP98/00858

§ 371 (c)(1),
(2), (4) Date: Dec. 3, 1998

(87) PCT Pub. No.: WO98/39452

PCT Pub. Date: Sep. 11, 1998

(30) Foreign Application Priority Data

Mar. 3, 1997 (JP) ............................................. 9-047838

(51) Int. Cl.$^7$ ................................................ C12N 9/10
(52) U.S. Cl. .................... 435/193; 435/183; 435/252.1; 435/252.3; 435/320.1; 536/23.1
(58) Field of Search ................................ 435/183, 193, 435/252.1, 252.3, 320.1; 536/23.1

(56) References Cited

FOREIGN PATENT DOCUMENTS

| EP | 87300716.5 | * | 10/1989 | |
| EP | 0635572 A2 | | 1/1995 | |
| GB | 2216530 A | * | 10/1989 | ........... C12N/15/00 |
| JP | 41-21756 | | 12/1941 | |
| JP | 42-3074 | | 2/1942 | |
| JP | A56-160998 | | 12/1981 | |
| JP | A61-202686 | | 9/1986 | |
| JP | A2-27980 | | 1/1990 | |
| JP | 6-133790 | | 5/1994 | |
| JP | B27-40922 | | 5/1995 | |
| JP | A7-231789 | | 9/1995 | |

OTHER PUBLICATIONS

GenBank Accesion No. A11530, Feb. 1994.*
GenBank Accesion No. J04423, Feb. 1994.*
Swiss–Prot Accesion No. P54967, Oct. 1996.*
Swiss–Prot Accesion No. P19206, Nov. 1990.*
Swiss–Prot Accesion No. P53557, Oct. 1996.*
Swiss–Prot Accesion No. P46396, Nov. 1995.*
Swiss–Prot Accesion No. P12996, Jan. 1990.*
Swiss–Prot Accesion No. Q47862, Nov. 1997.*
Swiss–Prot Accesion No. P46715, Nov. 1995.*
Preston, G.M. Cloning gene family members using the polymerase chain reaction with degenerate oligonucleotide primers. In cDNA Library Protocols. Ed. I.G. Cowell and C.A. Austin. New Jersey: Humana Press inc. 1997, pp. 97–111.*
Imai et al. Molecular cloning of a pseudomonas paucimobilis gen encoding a 17–kilodalton polypeptide that eliminates HCI molecules from gamma–hexachlorocyclohexane. Journal of Bacteriology. Nov. 1991, vol. 173, No. 21, pp. 6811–6819.*
Flint et al. Purification and characterization of biotin synthases. Methods in enzymology. 1997, vol. 279, pp. 349–356.*
Yamazaki et al. Linkage of genes essential for synthesis of a polysaccharide capsule in sphingomonas strain S88. Journal of Bacteriology, May 1996, vol. 178, No. 9, pp. 2676–2687.*
Henikoff. Unidirectional digestion with exonuclease III in DNA sequence analysis. Methods in Enzymology. 1997, vol. 155, pp. 156–165.*
Otsuka et al, The Journal of Biological Chemistry, vol. 263, No., 36, Issue of Dec. 25, pp. 19577–19585, 1998.
Ohsawa et al, Gene, 80 (1989) 39–48, 1989 Elsevier Science Publishers B.V (Biomedical Division).
Gloeckler et al, Gene 87 (1990) 63–70 Elsevier Science Publishers B.V. (Biomedical Division).
Sakurai et al, Microbiology (1996), 142–3295–3303.
Ifuku and Yanagi, Fermentation and Industry, 46, 102–111 (1998).

* cited by examiner

*Primary Examiner*—Nashaat T. Nashed
*Assistant Examiner*—Christian L. Fronda
(74) *Attorney, Agent, or Firm*—Birch, Stewart, Kolasch & Birch, LLP

(57) ABSTRACT

A DNA fragment containing a gene concerned in biotin biosynthesis and derived from a microorganism belonging to the genus Sphingomonas, a plasmid containing said DNA fragment, and a biotin-producing transformant containing said plasmid. There is provided a technique for utilizing a gene concerned in biotin biosynthesis and derived from a microorganism belonging to the genus Sphingomonas, for breeding of a biotin-producing micro-organism by genetic engineering.

24 Claims, 5 Drawing Sheets

SEQUENCE LISTING

<160> NUMBER OF SEQ ID NOS: 52

<210> SEQ ID NO 1
<211> LENGTH: 369
<212> TYPE: PRT
<213> ORGANISM: Sphingomonas paucimobilis
<220> FEATURE:
<223> OTHER INFORMATION: Strain = JCM7511

<400> SEQUENCE: 1

```
Met Leu Asp Phe His Arg Ala Asp Leu Ala Arg Leu Ala Ala Arg Asp
 1               5                  10                  15

Arg Leu Arg Val Leu Ala Pro Gln Arg Gly Lys Asp Phe Ala Ser Asn
             20                  25                  30

Asp Tyr Leu Gly Leu Ala Asn Ser Pro Arg Leu Ala Ala Ala Ile Ala
         35                  40                  45

Ala Ala Val Glu Glu Gly Val Pro Val Gly Ser Gly Ser Arg Leu
     50                  55                  60

Leu Arg Gly Asn His Pro Glu His Glu Ala Leu Glu Ala Asp Ala Ala
 65                  70                  75                  80

Ala Phe Phe Gly Ala Glu Ala Ser Leu Tyr Phe Ser Ser Gly Tyr Gly
                 85                  90                  95

Ala Asn Val Ala Ile Leu Ala Thr Leu Pro Gln Arg Gly Asp Leu Ile
            100                 105                 110

Val His Asp Ser Leu Val His Ala Ser Met Arg Leu Val His His Gln
        115                 120                 125

His Arg Ile Val Pro Ile Gly Gly Arg Leu Glu Ile Gly Glu Arg Arg
    130                 135                 140
```

Gly Val Ala Val His Ala Val Lys Ala Phe Asp Arg Asp Pro His Gly
145                 150                 155                 160

Ala Leu Ala Ala Leu Val Ala Pro Cys Pro Asp Arg Ile Leu Glu Gly
            165                 170                 175

Arg Cys Ile Val Met Arg Arg His Gly Leu Gly Thr Arg Gln Ala
                180                 185                 190

His Pro Leu Met His Ala Thr Gly Val Phe Gly Glu Arg Gly Gln Gly
            195                 200                 205

Leu Ser Ile Ala Gly Glu Arg Val Val Thr Leu His Thr Cys Gly Lys
        210                 215                 220

Ala Met Gly Cys Glu Gly Ala Leu Val Ala Gly Pro Thr Ile Val Arg
225                 230                 235                 240

Asp Tyr Leu Val Asn Arg Gly Arg Gly Phe Ile Phe Ser Thr Ala Pro
            245                 250                 255

Ser Pro Leu Met Ala Arg Gly Val Arg Glu Ala Leu Arg Ile Leu Ala
            260                 265                 270

Asp Glu Pro Glu Arg Arg Thr Ala Leu His Asp Arg Ile Ala Leu Ala
        275                 280                 285

Gly Ala Arg Leu Gly Arg Arg Gly Ala Leu Ala Gln Gly Thr Pro Ile
290                 295                 300

Leu Pro Leu Ile Leu His Asp Asn Gly Arg Thr Met Arg Ala Ala Glu
305                 310                 315                 320

Ala Leu Gln Ala Leu Gly Tyr Asp Ile Arg Gly Ile Arg Pro Pro Thr
            325                 330                 335

Val Pro Val Gly Ser Ala Arg Leu Arg Leu Ser Ile Thr Leu Asn Val
            340                 345                 350

Glu Ala Ala Asp Ile Leu Ala Leu Asp Gln Ala Leu Gln Glu Val Leu
        355                 360                 365

Ala

<210> SEQ ID NO 2
<211> LENGTH: 387
<212> TYPE: PRT
<213> ORGANISM: Sphingomonas sp.
<220> FEATURE:
<223> OTHER INFORMATION: Strain = SC42405

<400> SEQUENCE: 2

Met Ser Arg Leu Asp Ser Phe Phe Ala Ala Leu Asp Arg Ile Asp
1               5                   10                  15

Arg Ala Gly Gln Arg Arg Thr Leu Arg Pro Ala Ala Leu Glu Lys Gly
            20                  25                  30

Gly Arg Val His Arg Asp Gly His Glu Leu Ile Asp Phe Ser Ser Asn
        35                  40                  45

Asp Tyr Leu Gly Leu Ala Arg His Pro Leu Leu Ile Glu Arg Ala Arg
    50                  55                  60

Ala Trp Thr Glu Ala His Gly Thr Gly Ser Gly Ala Ser Arg Leu Val
65                  70                  75                  80

Thr Gly Thr Ser Ala Thr His Leu Ala Ile Glu Ala Arg Ile Ala Arg
                85                  90                  95

Phe Lys His Ala Glu Ala Ala Leu Val Phe Ala Ser Gly Trp Gln Ala
            100                 105                 110

Asn Ala Ala Val Ile Pro Ala Leu Leu Ala Ala Val Pro Gly Ser Ala
        115                 120                 125

-continued

Val Phe Thr Asp Arg Leu Ile His Ala Ser Met His Ala Gly Leu Ala
    130                 135                 140

Ile Ser Gly Thr Arg Gln His Arg Phe Arg His Asn Asp Leu Asp His
145                 150                 155                 160

Leu Glu Glu Leu Leu Ala Ser Lys Gly Ala Glu Ala Ser Ala Arg Leu
                165                 170                 175

Ile Leu Thr Glu Ser Val Phe Ser Met Asp Gly Asp Arg Ala Asp Ile
            180                 185                 190

Ala Arg Leu Ala Glu Ile Ala Ala Arg His Asp Ala Phe Leu Phe Val
        195                 200                 205

Asp Glu Ala His Ala Thr Gly Val Leu Gly Pro Gly Ala Gly Leu
    210                 215                 220

Ser Ala Glu Val Pro Gly Gly Ile Asp Leu Val Met Gly Thr Phe Ser
225                 230                 235                 240

Lys Ala Leu Gly Gly Phe Gly Ala Tyr Val Ala Gly Ser Gln Val Met
                245                 250                 255

Ile Asp Tyr Leu Val Asn Ala Ala Ser Gly Phe Ile Phe Thr Thr Ala
            260                 265                 270

Pro Pro Pro Ala Val Leu Gly Ala Ile Asp Ala Ala Leu Asp Leu Val
        275                 280                 285

Pro Gly Met Asp Ala Glu Arg Ala His Leu Ala Ala Leu Gly Gln Gln
    290                 295                 300

Leu Arg Ser Gly Leu Ala Ala Leu Gly Ile Asp His Gly Ala Ser Ser
305                 310                 315                 320

Thr Gln Ile Val Pro Ala Val Ile Gly Ala Glu Val Ala Ala Leu Asp
                325                 330                 335

Leu Ser Arg Lys Leu Glu Glu Arg Gly Leu Leu Ala Ser Ala Ile Arg
            340                 345                 350

Pro Pro Thr Val Pro Pro Gly Thr Ser Arg Leu Arg Leu Ala Leu Arg
        355                 360                 365

Ala Thr His Ala Pro Ser Asp Ile Asp Ala Leu Leu Asn Ala Ile Glu
    370                 375                 380

Ala Cys Arg
385

<210> SEQ ID NO 3
<211> LENGTH: 1536
<212> TYPE: DNA
<213> ORGANISM: Sphingomonas paucimobilis
<220> FEATURE:
<223> OTHER INFORMATION: Strain = JCM7511
<221> NAME/KEY: CDS
<222> LOCATION: (427)..(1533)

<400> SEQUENCE: 3
gatcctgatc gcggtcccgg cgcatcaatg gatgtggtcg gcgcatgacg tggtgaacca      60
tcaccatcgt cggtattcga agacgacctt ggggtccgcg atcgagaagg cgggcctgaa     120
accccgcaag ctcggctatt tcaactcgct gctcttcccg ctcgccgcgg ccgcgcggat     180
cgccggacgg atcacggggc gcgacgacag cgacgactcg ccaccgcccg cgccgctcaa     240
caaaacgttc gaggcgatct tccggttgga gcggcatctg gtcggccgtg tgccgatgac     300
cccgggggtt tcgatcgtga ccttggcgga gcctgcctga cggcgggtgg agcgaagtcg     360
aaggccacgg gaatccctaa cctttccggg ttccgctctc ctgcctagct gggtagggaa     420

```
                                                    -continued gccccc atg ctg gac ttt cat cgc gcc gat ctg gcc cga ctg gcc gcg        468
       Met Leu Asp Phe His Arg Ala Asp Leu Ala Arg Leu Ala Ala
         1               5                  10 cgg gac cga ttg cgg gtg ctg gcc ccg cag cgt ggc aag gat ttc gcg        516
Arg Asp Arg Leu Arg Val Leu Ala Pro Gln Arg Gly Lys Asp Phe Ala
 15              20                  25                  30 tcc aac gat tat ctg ggc ttg gcg aac agc ccc cgc ctc gcc gcc gcc        564
Ser Asn Asp Tyr Leu Gly Leu Ala Asn Ser Pro Arg Leu Ala Ala Ala
             35                  40                  45 atc gcc gcc gcg gtc gag gag ggc gtc ccc gtt ggg tcg ggc gga tcg        612
Ile Ala Ala Ala Val Glu Glu Gly Val Pro Val Gly Ser Gly Gly Ser
         50                  55                  60 cga ttg ctg cgc ggc aat cac ccc gaa cat gag gcg ctg gag gcg gac        660
Arg Leu Leu Arg Gly Asn His Pro Glu His Glu Ala Leu Glu Ala Asp
 65                  70                  75 gcc gcc gcg ttc ttc ggg gcg gag gcg agc ctg tat ttc tcc tcg ggc        708
Ala Ala Ala Phe Phe Gly Ala Glu Ala Ser Leu Tyr Phe Ser Ser Gly
         80                  85                  90 tac ggt gcc aat gtc gcg atc ctg gcg acg ctg cca cag cgc ggc gac        756
Tyr Gly Ala Asn Val Ala Ile Leu Ala Thr Leu Pro Gln Arg Gly Asp
 95                 100                 105                 110 ctg atc gtc cac gac tcg ctc gtc cat gcc agc atg cgc ctc gtc cac        804
Leu Ile Val His Asp Ser Leu Val His Ala Ser Met Arg Leu Val His
                115                 120                 125 cac cag cat cgc atc gtg ccg atc ggc ggc cgc ctg gag atc ggc gag        852
His Gln His Arg Ile Val Pro Ile Gly Gly Arg Leu Glu Ile Gly Glu
            130                 135                 140 cgg cgc ggt gtc gcc gtc cat gct gta aag gct ttc gac cgc gat cca        900
Arg Arg Gly Val Ala Val His Ala Val Lys Ala Phe Asp Arg Asp Pro
145                 150                 155 cac ggt gcc ctt gcc gcc ctg gtc gcg cca tgc ccg gat cgc atc ctc        948
His Gly Ala Leu Ala Ala Leu Val Ala Pro Cys Pro Asp Arg Ile Leu
    160                 165                 170 gaa ggc cga tgc atc gtt atg cgc cgc cgc cac ggc ctc ggc acg cga        996
Glu Gly Arg Cys Ile Val Met Arg Arg Arg His Gly Leu Gly Thr Arg
175                 180                 185                 190 cag gcg cat ccc ctc atg cat gcc acc ggc gtc ttc ggc gag cgg gga       1044
Gln Ala His Pro Leu Met His Ala Thr Gly Val Phe Gly Glu Arg Gly
                195                 200                 205 cag ggg ctg agc atc gca ggc gag cgg gtg gtg acg ctc cac acc tgt       1092
Gln Gly Leu Ser Ile Ala Gly Glu Arg Val Val Thr Leu His Thr Cys
            210                 215                 220 ggc aag gcg atg ggc tgc gag ggt gcg ctg gtc gcc ggg ccg acg atc       1140
Gly Lys Ala Met Gly Cys Glu Gly Ala Leu Val Ala Gly Pro Thr Ile
        225                 230                 235 gtg cgc gac tat ctg gtc aat cgc ggg agg ggc ttc atc ttc tcg acc       1188
Val Arg Asp Tyr Leu Val Asn Arg Gly Arg Gly Phe Ile Phe Ser Thr
240                 245                 250 gcg ccc tcg ccg ctg atg gca cgc ggg gtg cgc gag gcg ctt cgc atc       1236
Ala Pro Ser Pro Leu Met Ala Arg Gly Val Arg Glu Ala Leu Arg Ile
255                 260                 265                 270 ctg gcc gac gag ccc gag cgg cgc acc gcg ctg cac gac cgg atc gcg       1284
Leu Ala Asp Glu Pro Glu Arg Arg Thr Ala Leu His Asp Arg Ile Ala
                275                 280                 285 ctg gcg ggc gcg cgg ctg ggc cgc cgc ggt gcg ctg gcg cag ggc acg       1332
Leu Ala Gly Ala Arg Leu Gly Arg Arg Gly Ala Leu Ala Gln Gly Thr
            290                 295                 300 ccg atc ctg ccg ctg atc ctg cac gac aat ggc cgc acc atg cgc gcc       1380
Pro Ile Leu Pro Leu Ile Leu His Asp Asn Gly Arg Thr Met Arg Ala
        305                 310                 315
```

-continued

```
gct gag gcg ctg cag gcg ctt ggc tat gac ata cgc ggc atc cgc ccg    1428
Ala Glu Ala Leu Gln Ala Leu Gly Tyr Asp Ile Arg Gly Ile Arg Pro
    320                 325                 330 ccg acc gtg ccc gtg ggc tcg gcg cgg ctg cgg ctg tcg atc act ttg    1476
Pro Thr Val Pro Val Gly Ser Ala Arg Leu Arg Leu Ser Ile Thr Leu
335                 340                 345                 350 aat gtc gag gcg gcg gac atc ctc gcc ctc gac caa gca ttg caa gag    1524
Asn Val Glu Ala Ala Asp Ile Leu Ala Leu Asp Gln Ala Leu Gln Glu
                355                 360                 365 gtt ctg gca tga                                                     1536
Val Leu Ala
```

<210> SEQ ID NO 4
<211> LENGTH: 369
<212> TYPE: PRT
<213> ORGANISM: Sphingomonas paucimobilis

<400> SEQUENCE: 4

```
Met Leu Asp Phe His Arg Ala Asp Leu Ala Arg Leu Ala Ala Arg Asp
  1               5                  10                  15

Arg Leu Arg Val Leu Ala Pro Gln Arg Gly Lys Asp Phe Ala Ser Asn
                 20                  25                  30

Asp Tyr Leu Gly Leu Ala Asn Ser Pro Arg Leu Ala Ala Ala Ile Ala
             35                  40                  45

Ala Ala Val Glu Glu Gly Val Pro Val Gly Ser Gly Ser Arg Leu
         50                  55                  60

Leu Arg Gly Asn His Pro Glu His Glu Ala Leu Glu Ala Asp Ala Ala
 65                  70                  75                  80

Ala Phe Phe Gly Ala Glu Ala Ser Leu Tyr Phe Ser Ser Gly Tyr Gly
                 85                  90                  95

Ala Asn Val Ala Ile Leu Ala Thr Leu Pro Gln Arg Gly Asp Leu Ile
            100                 105                 110

Val His Asp Ser Leu Val His Ala Ser Met Arg Leu Val His His Gln
        115                 120                 125

His Arg Ile Val Pro Ile Gly Gly Arg Leu Glu Ile Gly Glu Arg Arg
    130                 135                 140

Gly Val Ala Val His Ala Val Lys Ala Phe Asp Arg Asp Pro His Gly
145                 150                 155                 160

Ala Leu Ala Ala Leu Val Ala Pro Cys Pro Asp Arg Ile Leu Glu Gly
                165                 170                 175

Arg Cys Ile Val Met Arg Arg His Gly Leu Gly Thr Arg Gln Ala
            180                 185                 190

His Pro Leu Met His Ala Thr Gly Val Phe Gly Glu Arg Gly Gln Gly
        195                 200                 205

Leu Ser Ile Ala Gly Glu Arg Val Val Thr Leu His Thr Cys Gly Lys
    210                 215                 220

Ala Met Gly Cys Glu Gly Ala Leu Val Ala Gly Pro Thr Ile Val Arg
225                 230                 235                 240

Asp Tyr Leu Val Asn Arg Gly Arg Gly Phe Ile Phe Ser Thr Ala Pro
                245                 250                 255

Ser Pro Leu Met Ala Arg Gly Val Arg Glu Ala Leu Arg Ile Leu Ala
            260                 265                 270

Asp Glu Pro Glu Arg Arg Thr Ala Leu His Asp Arg Ile Ala Leu Ala
        275                 280                 285

Gly Ala Arg Leu Gly Arg Arg Gly Ala Leu Ala Gln Gly Thr Pro Ile
    290                 295                 300
```

```
Leu Pro Leu Ile Leu His Asp Asn Gly Arg Thr Met Arg Ala Ala Glu
305                 310                 315                 320

Ala Leu Gln Ala Leu Gly Tyr Asp Ile Arg Gly Ile Arg Pro Pro Thr
            325                 330                 335

Val Pro Val Gly Ser Ala Arg Leu Arg Leu Ser Ile Thr Leu Asn Val
            340                 345                 350

Glu Ala Ala Asp Ile Leu Ala Leu Asp Gln Ala Leu Gln Glu Val Leu
            355                 360                 365

Ala

<210> SEQ ID NO 5
<211> LENGTH: 1408
<212> TYPE: DNA
<213> ORGANISM: Sphingomonas sp.
<220> FEATURE:
<223> OTHER INFORMATION: Strain = SC42405
<221> NAME/KEY: CDS
<222> LOCATION: (202)..(1362)

<400> SEQUENCE: 5
accggaatga caggcggaca gcagcaatag ggcggcaaga gagagcggca gggatcgcat      60
cagacgggca tccttcggtt tttcctttgc cgttccaacg cgcgaggaag gcggcggctt     120
cacgtcccgc cgcgaaatcg atgccctcc cggccagcca agcattgtgc cggacgcccg     180
cttgccatac cggcaggggc g atg agc agg ctc gat tcc ttc ttc gca gcg      231
                         Met Ser Arg Leu Asp Ser Phe Phe Ala Ala
                           1               5                  10 gcg ctc gac cgg atc gac cgc gcc gga caa cgc cgc acc ttg cgc ccc      279
Ala Leu Asp Arg Ile Asp Arg Ala Gly Gln Arg Arg Thr Leu Arg Pro
                15                  20                  25 gcc gca ctc gaa aag ggt ggc cgc gtc cac cgc gac ggg cac gaa ctg      327
Ala Ala Leu Glu Lys Gly Gly Arg Val His Arg Asp Gly His Glu Leu
            30                  35                  40 ata gat ttc tcc agc aac gac tat ctc ggc ctc gcc cgc cac ccg ctg      375
Ile Asp Phe Ser Ser Asn Asp Tyr Leu Gly Leu Ala Arg His Pro Leu
        45                  50                  55 ctg atc gag cgc gcc cgc gcc tgg acg gaa gcc cac ggc acc ggc tcc      423
Leu Ile Glu Arg Ala Arg Ala Trp Thr Glu Ala His Gly Thr Gly Ser
60                  65                  70 ggc gcc tcg cga ctg gtg acg gga acc agc gcc acc cat ctc gcg atc      471
Gly Ala Ser Arg Leu Val Thr Gly Thr Ser Ala Thr His Leu Ala Ile
75                  80                  85                  90 gag gcc cgc atc gcc cgg ttc aag cat gcc gaa gcc gcg ctg gtc ttc      519
Glu Ala Arg Ile Ala Arg Phe Lys His Ala Glu Ala Ala Leu Val Phe
                95                 100                 105 gcc agc ggc tgg cag gcc aat gcc gcg gtg atc ccc gcc ctg ctc gcc      567
Ala Ser Gly Trp Gln Ala Asn Ala Ala Val Ile Pro Ala Leu Leu Ala
            110                 115                 120 gcc gta ccc ggt tca gca gtc ttc acc gac cgg ctg atc cat gcc tcg      615
Ala Val Pro Gly Ser Ala Val Phe Thr Asp Arg Leu Ile His Ala Ser
        125                 130                 135 atg cac gcg ggc ctc gcg atc tcg ggc acc cgc cag cac cgc ttc cgc      663
Met His Ala Gly Leu Ala Ile Ser Gly Thr Arg Gln His Arg Phe Arg
    140                 145                 150 cat aac gac ctc gat cat ctg gag gaa ctg ctg gcg agc aag ggc gcc      711
His Asn Asp Leu Asp His Leu Glu Glu Leu Leu Ala Ser Lys Gly Ala
155                 160                 165                 170 gaa gcc tcc gcc cgc ctg atc ctc acc gag agc gtg ttc tcg atg gac      759
Glu Ala Ser Ala Arg Leu Ile Leu Thr Glu Ser Val Phe Ser Met Asp
                175                 180                 185
```

-continued

```
ggc gac cgc gcc gac att gcc cgc ctg gcc gag atc gcc gcc cgc cac        807
Gly Asp Arg Ala Asp Ile Ala Arg Leu Ala Glu Ile Ala Ala Arg His
            190                 195                 200 gac gca ttc ctg ttc gtg gac gaa gcc cat gcc acc ggc gtg ctc ggc        855
Asp Ala Phe Leu Phe Val Asp Glu Ala His Ala Thr Gly Val Leu Gly
        205                 210                 215 ccc ggc ggc gcg ggc ctc tcg gcg gaa gtg ccc ggc ggg atc gac ctc        903
Pro Gly Gly Ala Gly Leu Ser Ala Glu Val Pro Gly Gly Ile Asp Leu
    220                 225                 230 gtc atg ggc acc ttc agc aag gcg ctc ggc ggt ttc ggc gcc tat gtc        951
Val Met Gly Thr Phe Ser Lys Ala Leu Gly Gly Phe Gly Ala Tyr Val
235                 240                 245                 250 gcc ggg tca caa gtg atg atc gac tac ctc gtc aac gcg gcg agc ggc        999
Ala Gly Ser Gln Val Met Ile Asp Tyr Leu Val Asn Ala Ala Ser Gly
                255                 260                 265 ttc atc ttc acc acc gcc ccg ccg cct gcc gtg ctg ggc gcc atc gac       1047
Phe Ile Phe Thr Thr Ala Pro Pro Pro Ala Val Leu Gly Ala Ile Asp
            270                 275                 280 gcc gcg ctc gac ctc gtg ccg ggc atg gat gcc gag cgc gcc cat ctt       1095
Ala Ala Leu Asp Leu Val Pro Gly Met Asp Ala Glu Arg Ala His Leu
        285                 290                 295 gcc gcg ctg ggt cag cag ctg cgc tcc ggc ctc gcc gcg ctc ggc atc       1143
Ala Ala Leu Gly Gln Gln Leu Arg Ser Gly Leu Ala Ala Leu Gly Ile
    300                 305                 310 gat cac ggc gca tcg agc acg cag atc gtc ccc gcc gtg atc ggc gcg       1191
Asp His Gly Ala Ser Ser Thr Gln Ile Val Pro Ala Val Ile Gly Ala
315                 320                 325                 330 gag gtc gcc gcg ctc gac ctc tcc cgc aag ctg gaa gag cgc gga ctg       1239
Glu Val Ala Ala Leu Asp Leu Ser Arg Lys Leu Glu Glu Arg Gly Leu
                335                 340                 345 ctc gct tcc gcg atc cgc ccg ccc acg gtg ccg ccc ggc acc agc cgc       1287
Leu Ala Ser Ala Ile Arg Pro Pro Thr Val Pro Pro Gly Thr Ser Arg
            350                 355                 360 ctg cgc ctg gcg ctg cgc gcg acc cat gcg cca agc gat atc gat gcc       1335
Leu Arg Leu Ala Leu Arg Ala Thr His Ala Pro Ser Asp Ile Asp Ala
        365                 370                 375 ctg ctg aac gcg atc gag gcc tgc cgg tgaagctgct tttcgcccat            1382
Leu Leu Asn Ala Ile Glu Ala Cys Arg
    380                 385 ggctggggct tcgaccacac gttctg                                          1408
```

<210> SEQ ID NO 6
<211> LENGTH: 387
<212> TYPE: PRT
<213> ORGANISM: Sphingomonas sp.

<400> SEQUENCE: 6

Met Ser Arg Leu Asp Ser Phe Phe Ala Ala Leu Asp Arg Ile Asp
1               5                   10                  15

Arg Ala Gly Gln Arg Arg Thr Leu Arg Pro Ala Ala Leu Glu Lys Gly
            20                  25                  30

Gly Arg Val His Arg Asp Gly His Glu Leu Ile Asp Phe Ser Ser Asn
        35                  40                  45

Asp Tyr Leu Gly Leu Ala Arg His Pro Leu Leu Ile Glu Arg Ala Arg
    50                  55                  60

Ala Trp Thr Glu Ala His Gly Thr Gly Ser Gly Ala Ser Arg Leu Val
65                  70                  75                  80

Thr Gly Thr Ser Ala Thr His Leu Ala Ile Glu Ala Arg Ile Ala Arg
                85                  90                  95

-continued

```
Phe Lys His Ala Glu Ala Ala Leu Val Phe Ala Ser Gly Trp Gln Ala
             100                 105                 110
Asn Ala Ala Val Ile Pro Ala Leu Leu Ala Ala Val Pro Gly Ser Ala
        115                 120                 125
Val Phe Thr Asp Arg Leu Ile His Ala Ser Met His Ala Gly Leu Ala
130                 135                 140
Ile Ser Gly Thr Arg Gln His Arg Phe Arg His Asn Asp Leu Asp His
145                 150                 155                 160
Leu Glu Glu Leu Leu Ala Ser Lys Gly Ala Glu Ala Ser Ala Arg Leu
                165                 170                 175
Ile Leu Thr Glu Ser Val Phe Ser Met Asp Gly Asp Arg Ala Asp Ile
            180                 185                 190
Ala Arg Leu Ala Glu Ile Ala Ala Arg His Asp Ala Phe Leu Phe Val
        195                 200                 205
Asp Glu Ala His Ala Thr Gly Val Leu Gly Pro Gly Ala Gly Leu
210                 215                 220
Ser Ala Glu Val Pro Gly Gly Ile Asp Leu Val Met Gly Thr Phe Ser
225                 230                 235                 240
Lys Ala Leu Gly Gly Phe Gly Ala Tyr Val Ala Gly Ser Gln Val Met
                245                 250                 255
Ile Asp Tyr Leu Val Asn Ala Ala Ser Gly Phe Ile Phe Thr Thr Ala
            260                 265                 270
Pro Pro Pro Ala Val Leu Gly Ala Ile Asp Ala Ala Leu Asp Leu Val
        275                 280                 285
Pro Gly Met Asp Ala Glu Arg Ala His Leu Ala Ala Leu Gly Gln Gln
290                 295                 300
Leu Arg Ser Gly Leu Ala Ala Leu Gly Ile Asp His Gly Ala Ser Ser
305                 310                 315                 320
Thr Gln Ile Val Pro Ala Val Ile Gly Ala Glu Val Ala Ala Leu Asp
                325                 330                 335
Leu Ser Arg Lys Leu Glu Glu Arg Gly Leu Leu Ala Ser Ala Ile Arg
            340                 345                 350
Pro Pro Thr Val Pro Pro Gly Thr Ser Arg Leu Arg Leu Ala Leu Arg
        355                 360                 365
Ala Thr His Ala Pro Ser Asp Ile Asp Ala Leu Leu Asn Ala Ile Glu
    370                 375                 380
Ala Cys Arg
385

<210> SEQ ID NO 7
<211> LENGTH: 1408
<212> TYPE: DNA
<213> ORGANISM: Sphingomonas sp.
<220> FEATURE:
<223> OTHER INFORMATION: Strain = SC42405
<221> NAME/KEY: CDS
<222> LOCATION: (202)..(1362)

<400> SEQUENCE: 7
accggaatga caggcggaca gcagcaatag ggcggcaaga gagagcggca gggatcgcat    60
cagacgggca tccttcggtt tttcctttgc cgttccaacg cgcgaggaag gcggcggctt   120
cacgtcccgc cgcgaaatcg atgccctcc cggccagcca agcattgtgc cggacgcccg    180
cttgccatac gggcaggggc g atg agc agg ctc gat tcc ttc ttc gca gcg    231
                        Met Ser Arg Leu Asp Ser Phe Phe Ala Ala
                         1               5                  10
```

-continued

```
gcg ctc gac cgg atc gac cgc gcc gga caa cgc cgc acc ttg cgc ccc      279
Ala Leu Asp Arg Ile Asp Arg Ala Gly Gln Arg Arg Thr Leu Arg Pro
             15                  20                  25 gcc gca ctc gaa aag ggt ggc cgc gtc cac cgc gac ggg cac gaa ctg      327
Ala Ala Leu Glu Lys Gly Gly Arg Val His Arg Asp Gly His Glu Leu
         30                  35                  40 ata gat ttc tcc agc aac gac tat ctc ggc ctc gcc cgc cac ccg ctg      375
Ile Asp Phe Ser Ser Asn Asp Tyr Leu Gly Leu Ala Arg His Pro Leu
             45                  50                  55 ctg atc gag cgc gcc cgc gcc tgg acg gaa gcc cac ggc acc ggc tcc      423
Leu Ile Glu Arg Ala Arg Ala Trp Thr Glu Ala His Gly Thr Gly Ser
 60                  65                  70 ggc gcc tcg cga ctg gtg acg gga acc agc gcc acc cat ctc gcg atc      471
Gly Ala Ser Arg Leu Val Thr Gly Thr Ser Ala Thr His Leu Ala Ile
 75                  80                  85                  90 gag gcc cgc atc gcc cgg ttc aag cat gcc gaa gcc gcg ctg gtc ttc      519
Glu Ala Arg Ile Ala Arg Phe Lys His Ala Glu Ala Ala Leu Val Phe
                 95                 100                 105 gcc agc ggc tgg cag gcc aat gcc gcg gtg atc ccc gcc ctg ctc gcc      567
Ala Ser Gly Trp Gln Ala Asn Ala Ala Val Ile Pro Ala Leu Leu Ala
             110                 115                 120 gcc gta ccc ggt tca gca gtc ttc acc gac cgg ctg atc cat gcc tcg      615
Ala Val Pro Gly Ser Ala Val Phe Thr Asp Arg Leu Ile His Ala Ser
             125                 130                 135 atg cac gcg ggc ctc gcg atc tcg ggc acc cgc cag cac cgc ttc cgc      663
Met His Ala Gly Leu Ala Ile Ser Gly Thr Arg Gln His Arg Phe Arg
 140                 145                 150 cat aac gac ctc gat cat ctg gag gaa ctg ctg gcg agc aag ggc gcc      711
His Asn Asp Leu Asp His Leu Glu Glu Leu Leu Ala Ser Lys Gly Ala
155                 160                 165                 170 gaa gcc tcc gcc cgc ctg atc ctc acc gag agc gtg ttc tcg atg gac      759
Glu Ala Ser Ala Arg Leu Ile Leu Thr Glu Ser Val Phe Ser Met Asp
             175                 180                 185 ggc gac cgc gcc gac att gcc cgc ctg gcc gag atc gcc gcc cgc cac      807
Gly Asp Arg Ala Asp Ile Ala Arg Leu Ala Glu Ile Ala Ala Arg His
             190                 195                 200 gac gca ttc ctg ttc gtg gac gaa gcc cat gcc acc ggc gtg ctc ggc      855
Asp Ala Phe Leu Phe Val Asp Glu Ala His Ala Thr Gly Val Leu Gly
             205                 210                 215 ccc ggc ggc gcg ggc ctc tcg gcg gaa gtg ccc ggc ggg atc gac ctc      903
Pro Gly Gly Ala Gly Leu Ser Ala Glu Val Pro Gly Gly Ile Asp Leu
 220                 225                 230 gtc atg ggc acc ttc agc aag gcg ctc ggc ggt ttc ggc gcc tat gtc      951
Val Met Gly Thr Phe Ser Lys Ala Leu Gly Gly Phe Gly Ala Tyr Val
235                 240                 245                 250 gcc ggg tca caa gtg atg atc gac tac ctc gtc aac gcg gcg agc ggc      999
Ala Gly Ser Gln Val Met Ile Asp Tyr Leu Val Asn Ala Ala Ser Gly
             255                 260                 265 ttc atc ttc acc acc gcc ccg ccg cct gcc gtg ctg ggc gcc atc gac     1047
Phe Ile Phe Thr Thr Ala Pro Pro Pro Ala Val Leu Gly Ala Ile Asp
             270                 275                 280 gcc gcg ctc gac ctc gtg ccg ggc atg gat gcc gag cgc gcc cat ctt     1095
Ala Ala Leu Asp Leu Val Pro Gly Met Asp Ala Glu Arg Ala His Leu
         285                 290                 295 gcc gcg ctg ggt cag cag ctg cgc tcc ggc ctc gcc gcg ctc ggc atc     1143
Ala Ala Leu Gly Gln Gln Leu Arg Ser Gly Leu Ala Ala Leu Gly Ile
         300                 305                 310 gat cac ggc gca tcg agc acg cag atc gtc ccc gcc gtg atc ggc gcg     1191
Asp His Gly Ala Ser Ser Thr Gln Ile Val Pro Ala Val Ile Gly Ala
315                 320                 325                 330
```

```
gag gtc gcc gcg ctc gac ctc tcc cgc aag ctg gaa gag cgc gga ctg    1239
Glu Val Ala Ala Leu Asp Leu Ser Arg Lys Leu Glu Glu Arg Gly Leu
                335                 340                 345 ctc gct tcc gcg atc cgc ccg ccc acg gtg ccg ccc ggc acc agc cgc    1287
Leu Ala Ser Ala Ile Arg Pro Pro Thr Val Pro Pro Gly Thr Ser Arg
            350                 355                 360 ctg cgc ctg gcg ctg cgc gcg acc cat gcg cca agc gat atc gat gcc    1335
Leu Arg Leu Ala Leu Arg Ala Thr His Ala Pro Ser Asp Ile Asp Ala
        365                 370                 375 ctg ctg aac gcg atc gag gcc tgc cgg tgaagctgct tttcgcccat          1382
Leu Leu Asn Ala Ile Glu Ala Cys Arg
    380                 385 ggctggggct cgaccacac gttctg                                        1408
```

<210> SEQ ID NO 8
<211> LENGTH: 387
<212> TYPE: PRT
<213> ORGANISM: Sphingomonas sp.

<400> SEQUENCE: 8

```
Met Ser Arg Leu Asp Ser Phe Phe Ala Ala Leu Asp Arg Ile Asp
 1               5                  10                  15

Arg Ala Gly Gln Arg Arg Thr Leu Arg Pro Ala Ala Leu Glu Lys Gly
                 20                  25                  30

Gly Arg Val His Arg Asp Gly His Glu Leu Ile Asp Phe Ser Ser Asn
             35                  40                  45

Asp Tyr Leu Gly Leu Ala Arg His Pro Leu Leu Ile Glu Arg Ala Arg
         50                  55                  60

Ala Trp Thr Glu Ala His Gly Thr Gly Ser Gly Ala Ser Arg Leu Val
 65                  70                  75                  80

Thr Gly Thr Ser Ala Thr His Leu Ala Ile Glu Ala Arg Ile Ala Arg
                 85                  90                  95

Phe Lys His Ala Glu Ala Ala Leu Val Phe Ala Ser Gly Trp Gln Ala
            100                 105                 110

Asn Ala Ala Val Ile Pro Ala Leu Leu Ala Ala Val Pro Gly Ser Ala
        115                 120                 125

Val Phe Thr Asp Arg Leu Ile His Ala Ser Met His Ala Gly Leu Ala
    130                 135                 140

Ile Ser Gly Thr Arg Gln His Arg Phe Arg His Asn Asp Leu Asp His
145                 150                 155                 160

Leu Glu Glu Leu Leu Ala Ser Lys Gly Ala Glu Ala Ser Ala Arg Leu
                165                 170                 175

Ile Leu Thr Glu Ser Val Phe Ser Met Asp Gly Asp Arg Ala Asp Ile
            180                 185                 190

Ala Arg Leu Ala Glu Ile Ala Ala Arg His Asp Ala Phe Leu Phe Val
        195                 200                 205

Asp Glu Ala His Ala Thr Gly Val Leu Gly Pro Gly Ala Gly Leu
    210                 215                 220

Ser Ala Glu Val Pro Gly Gly Ile Asp Leu Val Met Gly Thr Phe Ser
225                 230                 235                 240

Lys Ala Leu Gly Gly Phe Gly Ala Tyr Val Ala Gly Ser Gln Val Met
                245                 250                 255

Ile Asp Tyr Leu Val Asn Ala Ala Ser Gly Phe Ile Phe Thr Thr Ala
            260                 265                 270

Pro Pro Pro Ala Val Leu Gly Ala Ile Asp Ala Ala Leu Asp Leu Val
        275                 280                 285
```

-continued

```
Pro Gly Met Asp Ala Glu Arg Ala His Leu Ala Ala Leu Gly Gln Gln
    290                 295                 300

Leu Arg Ser Gly Leu Ala Ala Leu Gly Ile Asp His Gly Ala Ser Ser
305                 310                 315                 320

Thr Gln Ile Val Pro Ala Val Ile Gly Ala Glu Val Ala Ala Leu Asp
                325                 330                 335

Leu Ser Arg Lys Leu Glu Arg Gly Leu Leu Ala Ser Ala Ile Arg
                340                 345                 350

Pro Pro Thr Val Pro Pro Gly Thr Ser Arg Leu Arg Leu Ala Leu Arg
            355                 360                 365

Ala Thr His Ala Pro Ser Asp Ile Asp Ala Leu Leu Asn Ala Ile Glu
        370                 375                 380

Ala Cys Arg
385

<210> SEQ ID NO 9
<211> LENGTH: 415
<212> TYPE: PRT
<213> ORGANISM: Sphingomonas paucimobilis
<220> FEATURE:
<223> OTHER INFORMATION: Strain = JCM7511

<400> SEQUENCE: 9

Met Thr Ser Pro Val Trp His Pro Phe Thr Gln His Gly Leu Gly Glu
  1               5                  10                  15

Pro Ile Pro Lys Val Ala Ser Ala Ser Gly Ala Val Leu Thr Thr Val
            20                  25                  30

Asp Gly Arg Glu Val Ile Asp Ala Ile Ser Ser Trp Trp Val Thr Thr
        35                  40                  45

His Gly His Asn His Pro Arg Ile Ser Ala Ala Ile Ala Glu Gln Ala
    50                  55                  60

Gly Lys Leu Asp Gln Ile Ile Phe Ala Gly Trp Thr His Glu Pro Ala
65                  70                  75                  80

Glu Glu Val Ala Ala Glu Leu Val Arg Ile Thr Pro Pro Lys Leu Thr
                85                  90                  95

Arg Val Phe Phe Ser Asp Ser Gly Ser Thr Ala Val Glu Val Ala Leu
            100                 105                 110

Lys Met Ala Leu Gly Tyr Trp Leu His Arg Gly Glu Pro Arg His Arg
        115                 120                 125

Ile Leu Val Leu Glu His Ser Tyr His Gly Asp Thr Ile Gly Ala Met
    130                 135                 140

Ser Val Gly Ala Arg Gly Val Tyr Asn Gln Ala Tyr Ala Pro Leu Leu
145                 150                 155                 160

Phe Asp Val Gly Thr Ile Pro Tyr Pro Thr Asp Ile Gln Ala Thr Leu
                165                 170                 175

Asp Thr Leu Glu Ala Glu Cys Arg Ala Gly Ala Ala Ala Phe Ile Val
            180                 185                 190

Glu Pro Leu Val Leu Gly Ala Gly Met Leu Phe Tyr Ala Ala Glu
        195                 200                 205

Thr Leu Ala Ala Met Arg Glu Ile Cys Ala Ala His Gly Val Leu Phe
    210                 215                 220

Ile Ala Asp Glu Val Met Thr Gly Trp Gly Arg Thr Gly Thr Ile Phe
225                 230                 235                 240

Ala Cys Asp Gln Ala Gly Val Val Pro Asp Ile Leu Cys Leu Ser Lys
                245                 250                 255
```

```
Gly Leu Thr Gly Gly Ala Val Pro Leu Ala Val Thr Leu Ala Thr Glu
            260                 265                 270

Ala Ile Phe Gln Ala His Trp Ser Glu Thr Asp Arg Ser Lys Gln Phe
            275                 280                 285

Phe His Ser Ser Ser Tyr Thr Ala Asn Pro Ile Ala Cys Ala Ala Ala
            290                 295                 300

Ala Ala Asn Leu Ala Ile Trp Arg Glu Pro Val Gln Ala Arg Ile
305                 310                 315                 320

Asp Ala Leu Ala Glu Arg Gln Arg Ala His Leu Ala Thr Ile Ala Gly
                325                 330                 335

Arg Asp Ala Val Arg Asn Pro Arg Ala Leu Gly Thr Ile Ala Ala Phe
            340                 345                 350

Glu Leu Gly Ala Gly Gln Asp Tyr Leu Ser Asp Leu Gly Pro Arg Leu
            355                 360                 365

Leu Ala His Phe Arg Glu Arg Asp Leu Leu Val Arg Pro Met Gly Asn
            370                 375                 380

Ser Ile Tyr Val Met Pro Pro Tyr Ser Ile Thr Pro Glu Gln Leu Ala
385                 390                 395                 400

Arg Ile Trp Gly Gly Ile Asp Glu Ala Ile Ala Arg Phe Gly Ser
                405                 410                 415

<210> SEQ ID NO 10
<211> LENGTH: 417
<212> TYPE: PRT
<213> ORGANISM: Sphingomonas sp.
<220> FEATURE:
<223> OTHER INFORMATION: Strain = SC42405

<400> SEQUENCE: 10

Met Thr Ser Ser Val Trp His Pro Phe Thr Gln His Gly Leu Gln Glu
 1               5                  10                  15

Pro Val Pro Leu Val Thr His Ala Glu Gly Ala Leu Leu His Thr Ala
                20                  25                  30

Asp Gly Lys Ala Val Val Asp Ala Val Ser Ser Trp Trp Val Thr Thr
            35                  40                  45

His Gly His Ser His Pro Arg Ile Lys Ala Ala Ile Ala Glu Gln Ala
        50                  55                  60

Gln Lys Leu Asp Gln Ile Ile Phe Ala Gly Trp Thr His Glu Pro Ala
65                  70                  75                  80

Glu Gln Val Ala Ala Gly Leu Arg Ala Ile Met Pro Glu Ser Leu Thr
                85                  90                  95

Arg Val Phe Phe Ser Asp Ser Gly Ser Thr Ser Val Glu Val Ala Leu
            100                 105                 110

Lys Met Ala Leu Gly Tyr Trp His Trp Arg Gly Glu Asn Arg His Arg
        115                 120                 125

Ile Val Val Met Glu Asn Ser Tyr His Gly Asp Thr Ile Gly Ala Met
130                 135                 140

Ser Val Gly Glu Arg Gly Val Phe Asn Gln Pro Tyr Glu Pro Leu Leu
145                 150                 155                 160

Phe Asp Val Gly Arg Ile Pro Phe Pro Ala Ala Gly Ala Glu Gln Ala
                165                 170                 175

Thr Leu Asp Ala Leu Glu Ala Ile Cys Arg Gln Pro Asp Thr Ala Ala
            180                 185                 190

Leu Ile Val Glu Pro Leu Ile Leu Gly Ala Gly Gly Met Leu Val Tyr
        195                 200                 205
```

```
Ser Ser Glu Thr Leu Ala Ala Met Gln Ala Ile Cys Ala Arg His Gly
    210                 215                 220

Val Leu Phe Ile Ala Asp Glu Val Met Thr Ala Trp Gly Arg Thr Gly
225                 230                 235                 240

Thr Leu Leu Ala Cys Glu Gln Ala Ser Val Val Pro Asp Ile Leu Cys
                245                 250                 255

Leu Ser Lys Gly Leu Thr Gly Gly Ala Val Pro Leu Ala Val Thr Met
                260                 265                 270

Ala Ser Glu Ala Ile Phe Glu Ala His Tyr Ser Thr Asp Arg Ala Arg
            275                 280                 285

Met Phe Phe His Ser Ser Ser Tyr Thr Ala Asn Pro Ile Ala Cys Ala
            290                 295                 300

Ala Ala Ala Ala Asn Leu Ala Ile Trp Arg Glu Pro Val Leu Glu
305                 310                 315                 320

Arg Ile Ala Ala Leu Ala Gly Lys Gln Ala Thr Trp Ile Glu Lys Leu
                325                 330                 335

Gly Gln Phe Cys His Phe Asp Asn Pro Arg Thr Ile Gly Thr Ile Ala
                340                 345                 350

Ala Leu Asp Leu Arg Thr Ser Gly Thr Ser Gly Tyr Met Ser Asp Leu
            355                 360                 365

Ala Pro Arg Leu Met Ala Phe Phe Arg Glu Arg Asp Val Leu Leu Arg
370                 375                 380

Pro Leu Gly Asn Thr Val Tyr Val Met Pro Pro Tyr Cys Ile Ser Asp
385                 390                 395                 400

Asn Gln Leu Gly Gln Val Trp Glu Ala Val Gly Glu Ala Val Ile Ser
                405                 410                 415

Phe
```

<210> SEQ ID NO 11
<211> LENGTH: 1448
<212> TYPE: DNA
<213> ORGANISM: Sphingomonas paucimobilis
<220> FEATURE:
<223> OTHER INFORMATION: Strain = JCM7511
<221> NAME/KEY: CDS
<222> LOCATION: (1)..(1245)

<400> SEQUENCE: 11

```
atg acc tcg ccg gtc tgg cat ccc ttc acc cag cat ggt ctg ggc gag     48
Met Thr Ser Pro Val Trp His Pro Phe Thr Gln His Gly Leu Gly Glu
1               5                   10                  15 ccg att cct aag gtg gct tcc gcc tct ggc gcg gtg ctg acc acc gtc     96
Pro Ile Pro Lys Val Ala Ser Ala Ser Gly Ala Val Leu Thr Thr Val
            20                  25                  30 gat ggc cgc gag gtg atc gat gcc atc tct agc tgg tgg gtg acc acg    144
Asp Gly Arg Glu Val Ile Asp Ala Ile Ser Ser Trp Trp Val Thr Thr
        35                  40                  45 cac ggg cac aac cat ccc cgc atc agc gcc gcc atc gcc gag cag gca    192
His Gly His Asn His Pro Arg Ile Ser Ala Ala Ile Ala Glu Gln Ala
    50                  55                  60 ggc aag ctc gac cag atc atc ttc gcc ggc tgg acc cat gag ccg gcc    240
Gly Lys Leu Asp Gln Ile Ile Phe Ala Gly Trp Thr His Glu Pro Ala
65                  70                  75                  80 gag gag gtt gcc gcc gag ctg gta cgg atc acg ccg ccc aag ctg acg    288
Glu Glu Val Ala Ala Glu Leu Val Arg Ile Thr Pro Pro Lys Leu Thr
                85                  90                  95
```

-continued

| | |
|---|---|
| cgg gtg ttc ttt tcc gat tct ggt tcg acg gcg gtc gag gtc gcg ctg<br>Arg Val Phe Phe Ser Asp Ser Gly Ser Thr Ala Val Glu Val Ala Leu<br>100                       105                    110 | 336 |
| aag atg gcg ctg ggc tac tgg ctc cac cgg ggc gag ccg cgc cac cgc<br>Lys Met Ala Leu Gly Tyr Trp Leu His Arg Gly Glu Pro Arg His Arg<br>115                      120                    125 | 384 |
| atc ctc gtc ctc gaa cac agc tat cat ggc gac acg atc ggc gcg atg<br>Ile Leu Val Leu Glu His Ser Tyr His Gly Asp Thr Ile Gly Ala Met<br>130                       135                    140 | 432 |
| tcg gtc ggc gcg cgg ggg gta tac aac cag gct tat gcg ccg ttg ctg<br>Ser Val Gly Ala Arg Gly Val Tyr Asn Gln Ala Tyr Ala Pro Leu Leu<br>145                     150                    155                    160 | 480 |
| ttc gat gtc ggc acc atc ccc tat ccg acc gac ata cag gcg acg ctc<br>Phe Asp Val Gly Thr Ile Pro Tyr Pro Thr Asp Ile Gln Ala Thr Leu<br>                    165                    170                    175 | 528 |
| gac acg ctg gag gcg gag tgc cgg gcg ggc gcg gcg ttc atc gtc<br>Asp Thr Leu Glu Ala Glu Cys Arg Ala Gly Ala Ala Ala Phe Ile Val<br>180                       185                    190 | 576 |
| gag ccg ctg gtg ctg ggg gcg ggg ggc atg ctc ttc tac gcc gcc gaa<br>Glu Pro Leu Val Leu Gly Ala Gly Gly Met Leu Phe Tyr Ala Ala Glu<br>195                      200                    205 | 624 |
| acg ctg gcc gcg atg cgt gag ata tgc gcg gcg cat ggc gtg ctg ttc<br>Thr Leu Ala Ala Met Arg Glu Ile Cys Ala Ala His Gly Val Leu Phe<br>210                       215                    220 | 672 |
| atc gct gat gag gtg atg acc gga tgg ggg cgc acc ggc acg atc ttc<br>Ile Ala Asp Glu Val Met Thr Gly Trp Gly Arg Thr Gly Thr Ile Phe<br>225                     230                    235                    240 | 720 |
| gcc tgt gac cag gcg ggc gtg gtc ccc gat atc ctc tgc ctg tcc aag<br>Ala Cys Asp Gln Ala Gly Val Val Pro Asp Ile Leu Cys Leu Ser Lys<br>                    245                    250                    255 | 768 |
| ggg ctg acc ggc ggt gcg gta ccg ctg gcg gtg aca ctg gcg acc gag<br>Gly Leu Thr Gly Gly Ala Val Pro Leu Ala Val Thr Leu Ala Thr Glu<br>260                       265                    270 | 816 |
| gcg atc ttc cag gcg cac tgg tcg gaa acc gat cgg tcg aag cag ttc<br>Ala Ile Phe Gln Ala His Trp Ser Glu Thr Asp Arg Ser Lys Gln Phe<br>275                       280                    285 | 864 |
| ttc cac tcg tcc agc tac acc gcc aac ccg atc gcc tgc gcg gcg gcg<br>Phe His Ser Ser Ser Tyr Thr Ala Asn Pro Ile Ala Cys Ala Ala Ala<br>290                       295                    300 | 912 |
| gcc gcc aat ctg gcg atc tgg cgc gag gag ccg gtg cag gcg cgg atc<br>Ala Ala Asn Leu Ala Ile Trp Arg Glu Glu Pro Val Gln Ala Arg Ile<br>305                     310                    315                    320 | 960 |
| gac gcg ctc gcc gag cgg cag cgg gcg cat ctg gcg acg atc gcg ggg<br>Asp Ala Leu Ala Glu Arg Gln Arg Ala His Leu Ala Thr Ile Ala Gly<br>                    325                    330                    335 | 1008 |
| cgg gat gcg gtg cga aac ccg cgc gcg ctc ggc acc atc gcg gcg ttc<br>Arg Asp Ala Val Arg Asn Pro Arg Ala Leu Gly Thr Ile Ala Ala Phe<br>340                       345                    350 | 1056 |
| gaa ctg ggg gcg ggg cag gat tat ctc tcc gat ctg gga ccc cgg ttg<br>Glu Leu Gly Ala Gly Gln Asp Tyr Leu Ser Asp Leu Gly Pro Arg Leu<br>355                      360                    365 | 1104 |
| ctg gcc cat ttc cgg gag cgc gat ctg ctc gtc cgg ccg atg ggc aat<br>Leu Ala His Phe Arg Glu Arg Asp Leu Leu Val Arg Pro Met Gly Asn<br>370                       375                    380 | 1152 |
| agc atc tat gtc atg ccg ccc tat tcc att acg ccc gag caa ctg gcg<br>Ser Ile Tyr Val Met Pro Pro Tyr Ser Ile Thr Pro Glu Gln Leu Ala<br>385                     390                    395                    400 | 1200 |
| cgc att tgg ggc ggc atc gat gag gcg att gcc cgc ttc ggg agt<br>Arg Ile Trp Gly Gly Ile Asp Glu Ala Ile Ala Arg Phe Gly Ser<br>                    405                    410                    415 | 1245 |

-continued

```
tgagacgggc cggggccttt gactttacgg catttcattt gctttatccg gcgacgatcg    1305
aaaagggagc gggcatgggc gtggcgaaga ctggggcgat gggggctctg gcatcggtga    1365
cggcgctgat gtggggcctg ccgccaccg cgcagacgac cccgcccgcc gccaacccgg     1425
ccaccccgcc gctgggcccg atc                                            1448
```

<210> SEQ ID NO 12
<211> LENGTH: 415
<212> TYPE: PRT
<213> ORGANISM: Sphingomonas paucimobilis

<400> SEQUENCE: 12

```
Met Thr Ser Pro Val Trp His Pro Phe Thr Gln His Gly Leu Gly Glu
 1               5                  10                  15

Pro Ile Pro Lys Val Ala Ser Ala Ser Gly Ala Val Leu Thr Thr Val
                20                  25                  30

Asp Gly Arg Glu Val Ile Asp Ala Ile Ser Ser Trp Trp Val Thr Thr
            35                  40                  45

His Gly His Asn His Pro Arg Ile Ser Ala Ala Ile Ala Glu Gln Ala
        50                  55                  60

Gly Lys Leu Asp Gln Ile Ile Phe Ala Gly Trp Thr His Glu Pro Ala
 65                  70                  75                  80

Glu Val Ala Ala Glu Leu Val Arg Ile Thr Pro Pro Lys Leu Thr
                85                  90                  95

Arg Val Phe Phe Ser Asp Ser Gly Ser Thr Ala Val Glu Val Ala Leu
            100                 105                 110

Lys Met Ala Leu Gly Tyr Trp Leu His Arg Gly Glu Pro Arg His Arg
        115                 120                 125

Ile Leu Val Leu Glu His Ser Tyr His Gly Asp Thr Ile Gly Ala Met
    130                 135                 140

Ser Val Gly Ala Arg Gly Val Tyr Asn Gln Ala Tyr Ala Pro Leu Leu
145                 150                 155                 160

Phe Asp Val Gly Thr Ile Pro Tyr Pro Thr Asp Ile Gln Ala Thr Leu
                165                 170                 175

Asp Thr Leu Glu Ala Glu Cys Arg Ala Gly Ala Ala Phe Ile Val
            180                 185                 190

Glu Pro Leu Val Leu Gly Ala Gly Met Leu Phe Tyr Ala Ala Glu
        195                 200                 205

Thr Leu Ala Ala Met Arg Glu Ile Cys Ala Ala His Gly Val Leu Phe
    210                 215                 220

Ile Ala Asp Glu Val Met Thr Gly Trp Gly Arg Thr Gly Thr Ile Phe
225                 230                 235                 240

Ala Cys Asp Gln Ala Gly Val Val Pro Asp Ile Leu Cys Leu Ser Lys
                245                 250                 255

Gly Leu Thr Gly Gly Ala Val Pro Leu Ala Val Thr Leu Ala Thr Glu
            260                 265                 270

Ala Ile Phe Gln Ala His Trp Ser Glu Thr Asp Arg Ser Lys Gln Phe
        275                 280                 285

Phe His Ser Ser Tyr Thr Ala Asn Pro Ile Ala Cys Ala Ala Ala
    290                 295                 300

Ala Ala Asn Leu Ala Ile Trp Arg Glu Pro Val Gln Ala Arg Ile
305                 310                 315                 320

Asp Ala Leu Ala Glu Arg Gln Arg Ala His Leu Ala Thr Ile Ala Gly
                325                 330                 335
```

```
Arg Asp Ala Val Arg Asn Pro Arg Ala Leu Gly Thr Ile Ala Ala Phe
         340                 345                 350

Glu Leu Gly Ala Gly Gln Asp Tyr Leu Ser Asp Leu Gly Pro Arg Leu
             355                 360                 365

Leu Ala His Phe Arg Glu Arg Asp Leu Leu Val Arg Pro Met Gly Asn
         370                 375                 380

Ser Ile Tyr Val Met Pro Pro Tyr Ser Ile Thr Pro Glu Gln Leu Ala
385                 390                 395                 400

Arg Ile Trp Gly Gly Ile Asp Glu Ala Ile Ala Arg Phe Gly Ser
                 405                 410                 415

<210> SEQ ID NO 13
<211> LENGTH: 1459
<212> TYPE: DNA
<213> ORGANISM: Sphingomonas sp.
<220> FEATURE:
<223> OTHER INFORMATION: Strain = SC42405
<221> NAME/KEY: CDS
<222> LOCATION: (1)..(1251)

<400> SEQUENCE: 13 atg acg tca tcg gtc tgg cac ccc ttc acc cag cac ggc ctg caa gag      48
Met Thr Ser Ser Val Trp His Pro Phe Thr Gln His Gly Leu Gln Glu
  1               5                  10                  15 ccg gtc ccg ctg gtc acc cat gcc gag ggc gcg ctg ctc cac acg gct      96
Pro Val Pro Leu Val Thr His Ala Glu Gly Ala Leu Leu His Thr Ala
             20                  25                  30 gac ggc aag gca gtg gtg gac gcg gtg tcc tcg tgg tgg gtg acg acc     144
Asp Gly Lys Ala Val Val Asp Ala Val Ser Ser Trp Trp Val Thr Thr
         35                  40                  45 cac ggc cac tcc cat ccg cgc atc aag gcc gcc atc gcg gag cag gcg     192
His Gly His Ser His Pro Arg Ile Lys Ala Ala Ile Ala Glu Gln Ala
     50                  55                  60 cag aag ctc gac cag atc atc ttc gcc gga tgg acc cac gaa ccc gcc     240
Gln Lys Leu Asp Gln Ile Ile Phe Ala Gly Trp Thr His Glu Pro Ala
 65                  70                  75                  80 gag caa gtc gca gca ggc ctg cgc gcg atc atg ccg gaa agc ctg acg     288
Glu Gln Val Ala Ala Gly Leu Arg Ala Ile Met Pro Glu Ser Leu Thr
                 85                  90                  95 cgg gtg ttc ttc tcc gat tcg ggt tcg acc agc gtg gaa gtc gcg ctg     336
Arg Val Phe Phe Ser Asp Ser Gly Ser Thr Ser Val Glu Val Ala Leu
            100                 105                 110 aag atg gcg ctc ggc tac tgg cac tgg cgc ggc gag aac cgc cac cgc     384
Lys Met Ala Leu Gly Tyr Trp His Trp Arg Gly Glu Asn Arg His Arg
        115                 120                 125 atc gtc gtg atg gaa aac tcc tac cac ggc gac acc atc ggc gcg atg     432
Ile Val Val Met Glu Asn Ser Tyr His Gly Asp Thr Ile Gly Ala Met
    130                 135                 140 tcg gtg ggc gag cgc ggc gtg ttc aac cag ccc tac gaa ccg ctg ctg     480
Ser Val Gly Glu Arg Gly Val Phe Asn Gln Pro Tyr Glu Pro Leu Leu
145                 150                 155                 160 ttc gac gtg ggc cgc att ccc ttc ccc gcc gcc ggg gcc gag cag gca     528
Phe Asp Val Gly Arg Ile Pro Phe Pro Ala Ala Gly Ala Glu Gln Ala
                165                 170                 175 acg ctg gac gca ctc gaa gcg atc tgc cgc cag ccg gac acc gcc gcg     576
Thr Leu Asp Ala Leu Glu Ala Ile Cys Arg Gln Pro Asp Thr Ala Ala
            180                 185                 190 ctg atc gtc gag ccg ctg atc ctc ggc gcc ggc ggc atg ctg gtc tat     624
Leu Ile Val Glu Pro Leu Ile Leu Gly Ala Gly Gly Met Leu Val Tyr
        195                 200                 205
```

-continued

```
tcg tcc gag acg ctc gcc gcg atg cag gcg atc tgc gcc cgc cac ggc    672
Ser Ser Glu Thr Leu Ala Ala Met Gln Ala Ile Cys Ala Arg His Gly
    210                 215                 220 gtg ctc ttc atc gcc gac gaa gtg atg acc gcc tgg ggc cgc acc ggc    720
Val Leu Phe Ile Ala Asp Glu Val Met Thr Ala Trp Gly Arg Thr Gly
225                 230                 235                 240 acc ctc ctc gcc tgc gaa cag gca agc gtg gtc ccg gac atc ctc tgc    768
Thr Leu Leu Ala Cys Glu Gln Ala Ser Val Val Pro Asp Ile Leu Cys
                245                 250                 255 ctc tcc aag ggc ctg acc ggc ggt gcc gtc ccg ctc gct gtc acg atg    816
Leu Ser Lys Gly Leu Thr Gly Gly Ala Val Pro Leu Ala Val Thr Met
            260                 265                 270 gcc agc gaa gcg atc ttc gag gcg cac tac tcc acc gac cgc gcg cgg    864
Ala Ser Glu Ala Ile Phe Glu Ala His Tyr Ser Thr Asp Arg Ala Arg
        275                 280                 285 atg ttc ttc cac tcc tcc agc tac acc gcg aac ccg atc gcc tgc gcc    912
Met Phe Phe His Ser Ser Ser Tyr Thr Ala Asn Pro Ile Ala Cys Ala
    290                 295                 300 gcc gcc gcc gcc aac ctg gct atc tgg cgc gag gaa ccg gtg ctg gaa    960
Ala Ala Ala Ala Asn Leu Ala Ile Trp Arg Glu Glu Pro Val Leu Glu
305                 310                 315                 320 cgc atc gcc gcg ctg gcc ggg aaa cag gcg acg tgg atc gag aag ctc   1008
Arg Ile Ala Ala Leu Ala Gly Lys Gln Ala Thr Trp Ile Glu Lys Leu
                325                 330                 335 ggc cag ttc tgc cac ttc gac aat ccc cgc acg atc ggc acc atc gcc   1056
Gly Gln Phe Cys His Phe Asp Asn Pro Arg Thr Ile Gly Thr Ile Ala
            340                 345                 350 gcg ctc gac ctc agg acc tca ggc acc agc ggc tac atg agc gac ctc   1104
Ala Leu Asp Leu Arg Thr Ser Gly Thr Ser Gly Tyr Met Ser Asp Leu
        355                 360                 365 gcc ccg cgc ctg atg gcg ttc ttc cgc gag cgg gac gtg ctg ttg cgg   1152
Ala Pro Arg Leu Met Ala Phe Phe Arg Glu Arg Asp Val Leu Leu Arg
    370                 375                 380 ccg ctg ggg aac acc gtc tac gtc atg ccg cct tac tgc att tcc gat   1200
Pro Leu Gly Asn Thr Val Tyr Val Met Pro Pro Tyr Cys Ile Ser Asp
385                 390                 395                 400 aat cag ctt ggg cag gtt tgg gag gct gtc ggg gaa gcg gtg att tcg   1248
Asn Gln Leu Gly Gln Val Trp Glu Ala Val Gly Glu Ala Val Ile Ser
                405                 410                 415 ttt taagaacgat tttaagatga aggatgaaga gcaggggtca aaacccctgc         1301
Phe acccccattac tgtcgaggtc aggtacgacc tatccgtctt gcgcccatgg cagcgtcggg  1361
aggcatattg gctgcgccgc aaggagcgca ctacgcatag ggcgcgcgcg acgtcgacat  1421
tccgagggtc tggggatca tccccagga cttctccc                            1459
```

<210> SEQ ID NO 14
<211> LENGTH: 417
<212> TYPE: PRT
<213> ORGANISM: Sphingomonas sp.

<400> SEQUENCE: 14

```
Met Thr Ser Ser Val Trp His Pro Phe Thr Gln His Gly Leu Gln Glu
  1               5                  10                  15

Pro Val Pro Leu Val Thr His Ala Glu Gly Ala Leu Leu His Thr Ala
             20                  25                  30

Asp Gly Lys Ala Val Val Asp Ala Val Ser Ser Trp Trp Val Thr Thr
         35                  40                  45
```

-continued

```
His Gly His Ser His Pro Arg Ile Lys Ala Ala Ile Ala Glu Gln Ala
         50                  55                  60
Gln Lys Leu Asp Gln Ile Ile Phe Ala Gly Trp Thr His Glu Pro Ala
 65                  70                  75                  80
Glu Gln Val Ala Ala Gly Leu Arg Ala Ile Met Pro Glu Ser Leu Thr
                 85                  90                  95
Arg Val Phe Phe Ser Asp Ser Gly Ser Thr Ser Val Glu Val Ala Leu
                100                 105                 110
Lys Met Ala Leu Gly Tyr Trp His Trp Arg Gly Glu Asn Arg His Arg
                115                 120                 125
Ile Val Val Met Glu Asn Ser Tyr His Gly Asp Thr Ile Gly Ala Met
            130                 135                 140
Ser Val Gly Glu Arg Gly Val Phe Asn Gln Pro Tyr Glu Pro Leu Leu
145                 150                 155                 160
Phe Asp Val Gly Arg Ile Pro Phe Pro Ala Ala Gly Ala Glu Gln Ala
                165                 170                 175
Thr Leu Asp Ala Leu Glu Ala Ile Cys Arg Gln Pro Asp Thr Ala Ala
                180                 185                 190
Leu Ile Val Glu Pro Leu Ile Leu Gly Ala Gly Gly Met Leu Val Tyr
            195                 200                 205
Ser Ser Glu Thr Leu Ala Ala Met Gln Ala Ile Cys Ala Arg His Gly
210                 215                 220
Val Leu Phe Ile Ala Asp Glu Val Met Thr Ala Trp Gly Arg Thr Gly
225                 230                 235                 240
Thr Leu Leu Ala Cys Glu Gln Ala Ser Val Val Pro Asp Ile Leu Cys
                245                 250                 255
Leu Ser Lys Gly Leu Thr Gly Gly Ala Val Pro Leu Ala Val Thr Met
                260                 265                 270
Ala Ser Glu Ala Ile Phe Glu Ala His Tyr Ser Thr Asp Arg Ala Arg
            275                 280                 285
Met Phe Phe His Ser Ser Tyr Thr Ala Asn Pro Ile Ala Cys Ala
290                 295                 300
Ala Ala Ala Ala Asn Leu Ala Ile Trp Arg Glu Glu Pro Val Leu Glu
305                 310                 315                 320
Arg Ile Ala Ala Leu Ala Gly Lys Gln Ala Thr Trp Ile Glu Lys Leu
                325                 330                 335
Gly Gln Phe Cys His Phe Asp Asn Pro Arg Thr Ile Gly Thr Ile Ala
                340                 345                 350
Ala Leu Asp Leu Arg Thr Ser Gly Thr Ser Gly Tyr Met Ser Asp Leu
            355                 360                 365
Ala Pro Arg Leu Met Ala Phe Phe Arg Glu Arg Asp Val Leu Leu Arg
370                 375                 380
Pro Leu Gly Asn Thr Val Tyr Val Met Pro Pro Tyr Cys Ile Ser Asp
385                 390                 395                 400
Asn Gln Leu Gly Gln Val Trp Glu Ala Val Gly Glu Ala Val Ile Ser
                405                 410                 415
Phe
```

<210> SEQ ID NO 15
<211> LENGTH: 206
<212> TYPE: PRT
<213> ORGANISM: Sphingomonas paucimobilis
<220> FEATURE:
<223> OTHER INFORMATION: Strain = JCM7511

```
<400> SEQUENCE: 15

Met Ser Ala Ile Ile Val Thr Gly Thr Asp Thr Glu Ile Gly Lys Thr
 1               5                  10                  15

Val Phe Ser Ala Ala Leu Thr Gly Ala Leu Gly Ala Ser Tyr Trp Lys
             20                  25                  30

Pro Val Gln Ala Gly Thr Asp Glu Glu Gly His Gly Asp Ala Glu Thr
         35                  40                  45

Val Ser Ala Leu Ser Gly Arg Pro Val Leu Pro Ser Ala Tyr Arg Leu
     50                  55                  60

Lys Thr Pro Cys Ser Pro His Leu Ala Ala Glu Ile Asp Gly Val Thr
 65                  70                  75                  80

Ile Glu Ile Asp Arg Leu Val Leu Pro Gln Val Asp Gly Pro Leu Val
                 85                  90                  95

Ala Glu Gly Ala Gly Gly Val Leu Val Pro Val Thr Arg Gln Leu Leu
            100                 105                 110

Phe Ala Asp Leu Phe Ala Arg Trp Gly Arg Pro Val Val Leu Val Ala
        115                 120                 125

Arg Thr Gly Leu Gly Thr Ile Asn His Ser Leu Leu Ser Ile Glu Ala
    130                 135                 140

Leu Arg Ala Arg Gly Val Asp Val Leu Gly Val Ala Phe Val Gly Asp
145                 150                 155                 160

Ala Val Glu Asp Ser Glu Ala Thr Ile Ala Ala Ile Gly Gly Val Lys
                165                 170                 175

Arg Leu Gly Arg Leu Pro Arg Leu Ala Thr Leu Asn Arg Glu Thr Leu
            180                 185                 190

Thr Glu Ala Phe Ala Ala His Phe Arg Ser Glu Asp Phe Arg
        195                 200                 205

<210> SEQ ID NO 16
<211> LENGTH: 209
<212> TYPE: PRT
<213> ORGANISM: Sphingomonas sp.
<220> FEATURE:
<223> OTHER INFORMATION: Strain = SC42405

<400> SEQUENCE: 16

Met Arg Pro Leu Ile Val Thr Gly Thr Asp Thr Glu Ile Gly Lys Thr
 1               5                  10                  15

Val Phe Ala Ala Ala Leu Ala Gly Ala Leu Gly Ser His Tyr Trp Lys
             20                  25                  30

Pro Val Gln Ala Gly Leu Glu Glu Asp Gly Gly Asp Gly Asp Arg Val
         35                  40                  45

Ala Arg Leu Ser Gly Leu Pro Ala Ser His Ile Leu Pro Glu Ala Tyr
     50                  55                  60

Arg Leu Ala Thr Pro Cys Ser Pro His Leu Ala Ala Glu Ile Asp Gly
 65                  70                  75                  80

Val Glu Ile Asp Pro Glu Arg Leu Ala Leu Pro Gln Val Asp Gly Pro
                 85                  90                  95

Leu Val Val Glu Gly Ala Gly Gly Val Met Val Pro Leu Thr Arg Thr
            100                 105                 110

Thr Thr Tyr Ala Asp Gln Phe Ala Arg Trp Asn Ala Pro Val Val Leu
        115                 120                 125

Val Ala Arg Thr Met Leu Gly Thr Ile Asn His Ser Leu Leu Ser Ile
    130                 135                 140
```

```
Glu Ala Leu Arg Ala Arg Gly Val Glu Val Leu Gly Val Ala Phe Val
145                 150                 155                 160

Gly Asp Pro Met Glu Asp Ser Glu Ala Thr Ile Cys Ala Met Ala Asn
                165                 170                 175

Val Arg Arg Leu Gly Arg Leu Pro Arg Leu Ala Ser Leu Thr Pro Glu
            180                 185                 190

Asn Leu Ala Lys Ala Phe Ala Glu Asn Phe His Ile Gly Asp Phe Thr
            195                 200                 205

Gln

<210> SEQ ID NO 17
<211> LENGTH: 621
<212> TYPE: DNA
<213> ORGANISM: Sphingomonas paucimobilis
<220> FEATURE:
<223> OTHER INFORMATION: Strain = JCM7511
<221> NAME/KEY: CDS
<222> LOCATION: (1)..(618)

<400> SEQUENCE: 17 atg agc gcc atc atc gtc acc ggc act gat acc gag atc ggc aag acc    48
Met Ser Ala Ile Ile Val Thr Gly Thr Asp Thr Glu Ile Gly Lys Thr
 1               5                  10                  15 gtc ttc tcc gcc gcg ctg acc ggc gcg ttg ggg gcg agc tat tgg aag    96
Val Phe Ser Ala Ala Leu Thr Gly Ala Leu Gly Ala Ser Tyr Trp Lys
            20                  25                  30 ccg gtc cag gcg gga acc gac gag gaa ggg cat ggc gat gcc gag acg   144
Pro Val Gln Ala Gly Thr Asp Glu Glu Gly His Gly Asp Ala Glu Thr
        35                  40                  45 gtg tcg gcc ctg agc gga cgt ccg gtc ctg ccc tcc gcc tat cgg ttg   192
Val Ser Ala Leu Ser Gly Arg Pro Val Leu Pro Ser Ala Tyr Arg Leu
    50                  55                  60 aag acg ccc tgc tcg ccg cat ctg gcc gcc gag atc gac ggg gtg acg   240
Lys Thr Pro Cys Ser Pro His Leu Ala Ala Glu Ile Asp Gly Val Thr
65                  70                  75                  80 atc gag atc gat cgg ctg gtg ctg ccg cag gtg gac ggg ccg ctg gtc   288
Ile Glu Ile Asp Arg Leu Val Leu Pro Gln Val Asp Gly Pro Leu Val
                85                  90                  95 gcc gag ggg gcg ggc ggc gtg ctg gtg ccg gtg acg cgg cag ttg ctg   336
Ala Glu Gly Ala Gly Gly Val Leu Val Pro Val Thr Arg Gln Leu Leu
            100                 105                 110 ttc gcc gat ctc ttc gcc cgc tgg ggc cgg ccg gtg gtg ctg gtc gcg   384
Phe Ala Asp Leu Phe Ala Arg Trp Gly Arg Pro Val Val Leu Val Ala
        115                 120                 125 cgg acc ggg ctg ggg acg atc aac cac agc ctg ttg tcg atc gag gcg   432
Arg Thr Gly Leu Gly Thr Ile Asn His Ser Leu Leu Ser Ile Glu Ala
    130                 135                 140 ttg cgc gcg cgc ggc gtg gac gtg ctg ggg gtc gcg ttc gtc ggt gac   480
Leu Arg Ala Arg Gly Val Asp Val Leu Gly Val Ala Phe Val Gly Asp
145                 150                 155                 160 gca gtc gag gat agc gag gcc acc atc gcc gcg atc ggc ggg gtg aag   528
Ala Val Glu Asp Ser Glu Ala Thr Ile Ala Ala Ile Gly Gly Val Lys
                165                 170                 175 cga ctc ggc cgc ctg ccg cgt ctg gcc acg cta aat cgc gag aca ctg   576
Arg Leu Gly Arg Leu Pro Arg Leu Ala Thr Leu Asn Arg Glu Thr Leu
            180                 185                 190 acc gag gcg ttc gcg gcg cat ttc cgg agc gag gat ttc cga tga       621
Thr Glu Ala Phe Ala Ala His Phe Arg Ser Glu Asp Phe Arg
        195                 200                 205
```

<210> SEQ ID NO 18
<211> LENGTH: 206
<212> TYPE: PRT
<213> ORGANISM: Sphingomonas paucimobilis

<400> SEQUENCE: 18

```
Met Ser Ala Ile Ile Val Thr Gly Thr Asp Thr Glu Ile Gly Lys Thr
  1               5                  10                  15

Val Phe Ser Ala Ala Leu Thr Gly Ala Leu Gly Ala Ser Tyr Trp Lys
                 20                  25                  30

Pro Val Gln Ala Gly Thr Asp Glu Gly His Gly Asp Ala Glu Thr
             35                  40                  45

Val Ser Ala Leu Ser Gly Arg Pro Val Leu Pro Ser Ala Tyr Arg Leu
         50                  55                  60

Lys Thr Pro Cys Ser Pro His Leu Ala Ala Glu Ile Asp Gly Val Thr
 65                  70                  75                  80

Ile Glu Ile Asp Arg Leu Val Leu Pro Gln Val Asp Gly Pro Leu Val
                 85                  90                  95

Ala Glu Gly Ala Gly Gly Val Leu Val Pro Val Thr Arg Gln Leu Leu
             100                 105                 110

Phe Ala Asp Leu Phe Ala Arg Trp Gly Arg Pro Val Val Leu Val Ala
         115                 120                 125

Arg Thr Gly Leu Gly Thr Ile Asn His Ser Leu Leu Ser Ile Glu Ala
 130                 135                 140

Leu Arg Ala Arg Gly Val Asp Val Leu Gly Val Ala Phe Val Gly Asp
145                 150                 155                 160

Ala Val Glu Asp Ser Glu Ala Thr Ile Ala Ala Ile Gly Gly Val Lys
                 165                 170                 175

Arg Leu Gly Arg Leu Pro Arg Leu Ala Thr Leu Asn Arg Glu Thr Leu
             180                 185                 190

Thr Glu Ala Phe Ala Ala His Phe Arg Ser Glu Asp Phe Arg
         195                 200                 205
```

<210> SEQ ID NO 19
<211> LENGTH: 627
<212> TYPE: DNA
<213> ORGANISM: Sphingomonas sp.
<220> FEATURE:
<223> OTHER INFORMATION: Strain = SC42405
<221> NAME/KEY: CDS
<222> LOCATION: (1)..(624)

<400> SEQUENCE: 19

```
atg aga ccg ctt atc gtc acc gga acc gat acc gag atc ggc aag acc      48
Met Arg Pro Leu Ile Val Thr Gly Thr Asp Thr Glu Ile Gly Lys Thr
  1               5                  10                  15 gtc ttc gcc gcc gcg ctc gcg ggc gcc ctc ggc tca cat tac tgg aag      96
Val Phe Ala Ala Ala Leu Ala Gly Ala Leu Gly Ser His Tyr Trp Lys
                 20                  25                  30 ccg gtg cag gca ggc ctc gaa gaa gac ggc ggc gac ggc gac cgc gtg     144
Pro Val Gln Ala Gly Leu Glu Glu Asp Gly Gly Asp Gly Asp Arg Val
             35                  40                  45 gcg cgc ctc tcc ggc ctg cct gcc agc cat att ctg ccc gaa gcc tat     192
Ala Arg Leu Ser Gly Leu Pro Ala Ser His Ile Leu Pro Glu Ala Tyr
         50                  55                  60 cgc ctc gcc acc ccc tgc tcg ccg cac ctc gcc gcc gag atc gac ggg     240
Arg Leu Ala Thr Pro Cys Ser Pro His Leu Ala Ala Glu Ile Asp Gly
 65                  70                  75                  80
```

```
gtg gaa atc gat ccc gag cgc ctc gcc ttg ccg caa gtg gac ggt ccg      288
Val Glu Ile Asp Pro Glu Arg Leu Ala Leu Pro Gln Val Asp Gly Pro
            85                  90                  95 ctg gtg gtc gaa ggc gca ggc ggc gtc atg gtc ccg ctc acc cgg acc      336
Leu Val Val Glu Gly Ala Gly Gly Val Met Val Pro Leu Thr Arg Thr
100                 105                 110 acg act tat gcc gac cag ttc gcg cgg tgg aac gcc ccg gtc gtg ctg      384
Thr Thr Tyr Ala Asp Gln Phe Ala Arg Trp Asn Ala Pro Val Val Leu
            115                 120                 125 gtg gcg cgc acg atg ctc ggc acg atc aac cat tcg ctg ctc tcc atc      432
Val Ala Arg Thr Met Leu Gly Thr Ile Asn His Ser Leu Leu Ser Ile
130                 135                 140 gag gcc ctg cgc gcg cgc ggc gtc gaa gtg ctg ggc gtg gcc ttc gtc      480
Glu Ala Leu Arg Ala Arg Gly Val Glu Val Leu Gly Val Ala Phe Val
145                 150                 155                 160 ggc gat ccg atg gaa gac agc gag gcg acg atc tgc gcc atg gcc aat      528
Gly Asp Pro Met Glu Asp Ser Glu Ala Thr Ile Cys Ala Met Ala Asn
            165                 170                 175 gtc cgc cgc ctc ggc cgc ctg ccc cgc ctc gcc tcg ctg acc ccg gag      576
Val Arg Arg Leu Gly Arg Leu Pro Arg Leu Ala Ser Leu Thr Pro Glu
            180                 185                 190 aac ctc gcc aag gcc ttc gcc gaa aac ttc cat atc gga gat ttc acg      624
Asn Leu Ala Lys Ala Phe Ala Glu Asn Phe His Ile Gly Asp Phe Thr
            195                 200                 205 caa                                                                   627
```

<210> SEQ ID NO 20
<211> LENGTH: 208
<212> TYPE: PRT
<213> ORGANISM: Sphingomonas sp.

<400> SEQUENCE: 20

```
Met Arg Pro Leu Ile Val Thr Gly Thr Asp Thr Glu Ile Gly Lys Thr
  1               5                  10                  15

Val Phe Ala Ala Ala Leu Ala Gly Ala Leu Gly Ser His Tyr Trp Lys
                 20                  25                  30

Pro Val Gln Ala Gly Leu Glu Glu Asp Gly Gly Asp Gly Asp Arg Val
             35                  40                  45

Ala Arg Leu Ser Gly Leu Pro Ala Ser His Ile Leu Pro Glu Ala Tyr
         50                  55                  60

Arg Leu Ala Thr Pro Cys Ser Pro His Leu Ala Ala Glu Ile Asp Gly
 65                  70                  75                  80

Val Glu Ile Asp Pro Glu Arg Leu Ala Leu Pro Gln Val Asp Gly Pro
                 85                  90                  95

Leu Val Val Glu Gly Ala Gly Gly Val Met Val Pro Leu Thr Arg Thr
            100                 105                 110

Thr Thr Tyr Ala Asp Gln Phe Ala Arg Trp Asn Ala Pro Val Val Leu
        115                 120                 125

Val Ala Arg Thr Met Leu Gly Thr Ile Asn His Ser Leu Leu Ser Ile
130                 135                 140

Glu Ala Leu Arg Ala Arg Gly Val Glu Val Leu Gly Val Ala Phe Val
145                 150                 155                 160

Gly Asp Pro Met Glu Asp Ser Glu Ala Thr Ile Cys Ala Met Ala Asn
                165                 170                 175

Val Arg Arg Leu Gly Arg Leu Pro Arg Leu Ala Ser Leu Thr Pro Glu
            180                 185                 190
```

Asn Leu Ala Lys Ala Phe Ala Glu Asn Phe His Ile Gly Asp Phe Thr
            195                 200                 205

<210> SEQ ID NO 21
<211> LENGTH: 341
<212> TYPE: PRT
<213> ORGANISM: Sphingomonas paucimobilis
<220> FEATURE:
<223> OTHER INFORMATION: Strain = JCM7511

<400> SEQUENCE: 21

Met Thr Thr Thr Pro Ala Leu Ser Ser Glu Ala Thr Pro Arg Thr Asp
  1               5                  10                  15

Trp Thr Arg Ala Glu Ile Ala Ala Leu Phe Asp Leu Pro Phe Thr Glu
             20                  25                  30

Leu Leu Phe Arg Ala Ala Glu Val His Arg Ala His His Ala Ala Asp
         35                  40                  45

Gln Val Gln Leu Ser Thr Leu Leu Ser Ile Lys Thr Gly Gly Cys Pro
     50                  55                  60

Glu Asp Cys Gly Tyr Cys Ser Gln Ser Thr His Ala Asp Thr Gly Leu
 65                  70                  75                  80

Lys Ala Thr Lys Leu Met Asp Pro Arg Ala Val Leu Gln Ala Ala Ala
                 85                  90                  95

Gln Ala Lys Asp His Gly Ser Thr Arg Phe Cys Met Gly Ala Ala Trp
            100                 105                 110

Arg Asn Pro Lys Asp Arg Asp Met Pro Ala Ile Val Glu Met Val Lys
        115                 120                 125

Gly Val Arg Ala Met Gly Met Glu Thr Cys Met Thr Leu Gly Met Leu
    130                 135                 140

Thr Asp Ala Gln Ala Gln Thr Leu Ala Glu Ala Gly Leu Asp Tyr Tyr
145                 150                 155                 160

Asn His Asn Ile Asp Thr Ser Pro Glu Arg Tyr Gly Asp Val Ile Thr
                165                 170                 175

Thr Arg Ser Phe Gly Glu Arg Leu Glu Thr Leu Glu His Val Arg Asp
            180                 185                 190

Ala Gly Ile Asn Val Cys Cys Gly Gly Ile Val Gly Met Gly Glu Thr
        195                 200                 205

Arg Gly Asp Arg Val Gly Phe Ile His Ala Leu Ala Thr Leu Pro Val
    210                 215                 220

His Pro Gly Ser Val Pro Val Asn Ala Leu Val Pro Val Lys Gly Thr
225                 230                 235                 240

Val Leu Gly Asp Met Leu Ala Asp Thr Pro Leu Ala Lys Ile Asp Asp
                245                 250                 255

Ile Glu Phe Val Arg Thr Val Ala Val Ala Arg Ile Thr Met Pro His
            260                 265                 270

Ser Met Val Arg Leu Ser Ala Gly Arg Glu Ser Met Ser Asp Ala Thr
        275                 280                 285

Gln Ala Leu Cys Phe Leu Ala Gly Ala Asn Ser Ile Phe Thr Gly Asp
    290                 295                 300

Lys Leu Leu Thr Ala Gly Asn Ala Gly Asp Asp Lys Asp Ala Ala Leu
305                 310                 315                 320

Phe Ala Arg Leu Gly Leu Thr Pro Met Ala Ala Glu Cys Lys Val Glu
                325                 330                 335

Leu Glu Ala Ala Glu
            340

```
<210> SEQ ID NO 22
<211> LENGTH: 352
<212> TYPE: PRT
<213> ORGANISM: Sphingomonas sp.
<220> FEATURE:
<223> OTHER INFORMATION: Strain = SC42405

<400> SEQUENCE: 22
```

Met Thr Met Thr Asp Thr Pro Ala Ile Thr Ala Arg Thr Asp Trp Thr
 1               5                  10                  15

Arg Glu Glu Ile Ala Ala Leu Phe Asp Leu Pro Phe Thr Glu Leu Val
                20                  25                  30

Phe Arg Ala Ala Glu Val His Arg Ala Ser His Pro His Asn Glu Val
            35                  40                  45

Gln Leu Ser Thr Leu Leu Ser Ile Lys Thr Gly Gly Cys Val Glu Asp
     50                  55                  60

Cys Gly Tyr Cys Ser Gln Ser Val Ser Ala Asn Ser Gly Val Lys Ala
 65                  70                  75                  80

Thr Lys Leu Met Glu Val Gln Gln Val Leu Gln Arg Ala Ala Gln Ala
                85                  90                  95

Ala Asp Gln Gly Ser Thr Arg Phe Cys Met Gly Ala Ala Trp Arg Asn
            100                 105                 110

Pro Lys Asp Arg Asp Met Pro Ala Ile Ile Glu Met Val Lys Gly Val
        115                 120                 125

Arg Ala Met Gly Met Glu Thr Cys Met Thr Arg Gly Met Leu Thr Pro
130                 135                 140

Asp Gln Ala Asp Met Leu Ser Glu Ala Gly Leu Asp Tyr Tyr Asn His
145                 150                 155                 160

Asn Ile Asp Thr Ser Pro Glu Arg Tyr Asp Gln Val Ile Thr Thr Arg
                165                 170                 175

Thr Met Asp Asp Arg Leu Asp Thr Leu Ser Asn Val Arg Met Ala Gly
            180                 185                 190

Ile Asn Val Cys Ser Gly Gly Ile Val Gly Met Gly Glu Thr Arg Ala
        195                 200                 205

Asp Arg Val Gly Phe Val His Thr Leu Ala Thr Leu Pro Asp His Pro
    210                 215                 220

Gln Ser Val Pro Val Asn Ala Leu Val Pro Val Lys Gly Thr Val Leu
225                 230                 235                 240

Gly Asp Met Leu Ala Asp Thr Pro Leu Ala Lys Ile Asp Asp Val Glu
                245                 250                 255

Phe Val Arg Thr Val Ala Val Ala Arg Ile Thr Met Pro Leu Ser Met
            260                 265                 270

Val Arg Leu Ser Ala Gly Arg Glu Ser Met Ser Glu Met Thr Gln Ala
        275                 280                 285

Met Cys Phe Met Ala Gly Ala Asn Ser Ile Phe Thr Gly Asp Lys Leu
    290                 295                 300

Leu Thr Ala Pro Asn Ser Gly Asp Asp Asn Asp Ala Ala Met Phe Ala
305                 310                 315                 320

Arg Leu Gly Ile Lys Pro Met Ala Ile Glu Leu Thr Pro Ala Gln Val
                325                 330                 335

Glu Ala Gln Arg Met Pro Lys Gly Cys Ala Lys Leu Glu Ala Ala Glu
            340                 345                 350

```
<210> SEQ ID NO 23
<211> LENGTH: 1420
<212> TYPE: DNA
```

-continued

```
<213> ORGANISM: Sphingomonas paucimobilis
<220> FEATURE:
<223> OTHER INFORMATION: Strain = JCM7511
<221> NAME/KEY: CDS
<222> LOCATION: (223)..(1245)

<400> SEQUENCE: 23
gatccccgag ctgatcggcc atctgcgcga ggcgggccgc gcggatatca aggtcatcgc      60
gggtggcgtt attcccgcac aggactatca ggcactctac gatgccgggg tacaggcgat    120
tttcggtccc ggcaccaatc ttgtgaaagc ggccgaggat gtgctgaggc tgctgggaca    180
taatatgccg cccgaggcgg gcgaatgaca ggacgacacg tg atg acg acg aca       234
                                               Met Thr Thr Thr
                                                 1 ccc gcg ctg agc tcc gag gcg acc ccg cgc acc gac tgg acc cgc gcc      282
Pro Ala Leu Ser Ser Glu Ala Thr Pro Arg Thr Asp Trp Thr Arg Ala
  5                  10                  15                  20 gag atc gcc gcg ctg ttc gac ctg ccc ttc acc gag ctg ttg ttc cgc      330
Glu Ile Ala Ala Leu Phe Asp Leu Pro Phe Thr Glu Leu Leu Phe Arg
                 25                  30                  35 gcg gcc gag gtg cac cgc gcg cat cac gcc gcc gat cag gtt cag ctg      378
Ala Ala Glu Val His Arg Ala His His Ala Ala Asp Gln Val Gln Leu
             40                  45                  50 tcg acg ctg ttg tcg atc aag acg ggc ggc tgc ccc gag gat tgc ggc      426
Ser Thr Leu Leu Ser Ile Lys Thr Gly Gly Cys Pro Glu Asp Cys Gly
         55                  60                  65 tat tgc agc cag tcg acc cat gcc gat acc ggg ctg aag gcg acc aag      474
Tyr Cys Ser Gln Ser Thr His Ala Asp Thr Gly Leu Lys Ala Thr Lys
     70                  75                  80 ctg atg gac ccg cgc gcc gtg ctg cag gcg gcg gcg cag gcc aag gat      522
Leu Met Asp Pro Arg Ala Val Leu Gln Ala Ala Ala Gln Ala Lys Asp
 85                  90                  95                 100 cac ggc tcg acg cgc ttc tgc atg ggc gcg gcc tgg cgc aac ccc aag      570
His Gly Ser Thr Arg Phe Cys Met Gly Ala Ala Trp Arg Asn Pro Lys
                105                 110                 115 gat cgc gac atg ccc gcc atc gtg gag atg gtg aag ggc gtg cgc gcc      618
Asp Arg Asp Met Pro Ala Ile Val Glu Met Val Lys Gly Val Arg Ala
            120                 125                 130 atg ggc atg gaa acc tgc atg acg ctg ggc atg ctg acc gat gca cag      666
Met Gly Met Glu Thr Cys Met Thr Leu Gly Met Leu Thr Asp Ala Gln
        135                 140                 145 gcg cag acg ctc gcc gag gcg ggg ctg gac tat tac aat cac aat atc      714
Ala Gln Thr Leu Ala Glu Ala Gly Leu Asp Tyr Tyr Asn His Asn Ile
    150                 155                 160 gac acg tcg ccc gag cgt tat ggc gac gtc atc acc acg cgc agc ttc      762
Asp Thr Ser Pro Glu Arg Tyr Gly Asp Val Ile Thr Thr Arg Ser Phe
165                 170                 175                 180 ggc gag cgg ttg gag acg ttg gag cat gtc cgc gat gcc ggc atc aat      810
Gly Glu Arg Leu Glu Thr Leu Glu His Val Arg Asp Ala Gly Ile Asn
                185                 190                 195 gta tgc tgt ggc ggt att gtc ggc atg ggt gag acg cgc ggc gac cgg      858
Val Cys Cys Gly Gly Ile Val Gly Met Gly Glu Thr Arg Gly Asp Arg
            200                 205                 210 gtc ggc ttc atc cat gcg ctt gcc acc ctg ccg gtc cat ccg ggc agc      906
Val Gly Phe Ile His Ala Leu Ala Thr Leu Pro Val His Pro Gly Ser
        215                 220                 225 gtg ccg gtg aac gcg ctg gtg ccg gtc aag ggc acg gta ttg ggc gat      954
Val Pro Val Asn Ala Leu Val Pro Val Lys Gly Thr Val Leu Gly Asp
    230                 235                 240
```

```
atg ttg gcc gac acg ccg ctg gcc aag atc gac gat atc gaa ttc gtc    1002
Met Leu Ala Asp Thr Pro Leu Ala Lys Ile Asp Asp Ile Glu Phe Val
245                 250                 255                 260 cgc acc gtc gcg gtt gcg cgc atc acc atg ccg cat tcg atg gtc cgc    1050
Arg Thr Val Ala Val Ala Arg Ile Thr Met Pro His Ser Met Val Arg
                265                 270                 275 ctg tcg gcg ggg cgc gag agc atg tcg gat gcc acc cag gct ttg tgc    1098
Leu Ser Ala Gly Arg Glu Ser Met Ser Asp Ala Thr Gln Ala Leu Cys
            280                 285                 290 ttc ctg gcg ggc gcg aac tcg atc ttc acc ggc gac aag ctg ctg act    1146
Phe Leu Ala Gly Ala Asn Ser Ile Phe Thr Gly Asp Lys Leu Leu Thr
        295                 300                 305 gcg ggc aat gcg ggc gac gac aag gac gca gcg ctc ttc gcc cgg ctg    1194
Ala Gly Asn Ala Gly Asp Asp Lys Asp Ala Ala Leu Phe Ala Arg Leu
    310                 315                 320 ggg ctc acg ccc atg gcg gcg gag tgc aag gtg gaa ttg gaa gcg gcg    1242
Gly Leu Thr Pro Met Ala Ala Glu Cys Lys Val Glu Leu Glu Ala Ala
325                 330                 335                 340 gag taaacaggct tcgccggttg tccccggcga agccggagc ccagttgcgg           1295
Glu tgaagtaggg gtggtgcgcc acccgaatgg cattcgacac ggaccaacga cataatagga   1355
gaggtatccc cgtgttccag aaaatcctga tcgccaatcg cggggaaatc gcgtgccggg   1415
tgatc                                                              1420

<210> SEQ ID NO 24
<211> LENGTH: 341
<212> TYPE: PRT
<213> ORGANISM: Sphingomonas paucimobilis

<400> SEQUENCE: 24

Met Thr Thr Thr Pro Ala Leu Ser Ser Glu Ala Thr Pro Arg Thr Asp
  1               5                  10                  15

Trp Thr Arg Ala Glu Ile Ala Ala Leu Phe Asp Leu Pro Phe Thr Glu
                 20                  25                  30

Leu Leu Phe Arg Ala Ala Glu Val His Arg Ala His Ala Ala Ala Asp
             35                  40                  45

Gln Val Gln Leu Ser Thr Leu Leu Ser Ile Lys Thr Gly Gly Cys Pro
         50                  55                  60

Glu Asp Cys Gly Tyr Cys Ser Gln Ser Thr His Ala Asp Thr Gly Leu
 65                  70                  75                  80

Lys Ala Thr Lys Leu Met Asp Pro Arg Ala Val Leu Gln Ala Ala Ala
                 85                  90                  95

Gln Ala Lys Asp His Gly Ser Thr Arg Phe Cys Met Gly Ala Ala Trp
            100                 105                 110

Arg Asn Pro Lys Asp Arg Asp Met Pro Ala Ile Val Glu Met Val Lys
        115                 120                 125

Gly Val Arg Ala Met Gly Met Glu Thr Cys Met Thr Leu Gly Met Leu
    130                 135                 140

Thr Asp Ala Gln Ala Gln Thr Leu Ala Glu Ala Gly Leu Asp Tyr Tyr
145                 150                 155                 160

Asn His Asn Ile Asp Thr Ser Pro Glu Arg Tyr Gly Asp Val Ile Thr
                165                 170                 175

Thr Arg Ser Phe Gly Glu Arg Leu Glu Thr Leu Glu His Val Arg Asp
            180                 185                 190

Ala Gly Ile Asn Val Cys Cys Gly Gly Ile Val Gly Met Gly Glu Thr
        195                 200                 205
```

```
Arg Gly Asp Arg Val Gly Phe Ile His Ala Leu Ala Thr Leu Pro Val
    210                 215                 220

His Pro Gly Ser Val Pro Val Asn Ala Leu Val Pro Val Lys Gly Thr
225                 230                 235                 240

Val Leu Gly Asp Met Leu Ala Asp Thr Pro Leu Ala Lys Ile Asp Asp
                245                 250                 255

Ile Glu Phe Val Arg Thr Val Ala Val Ala Arg Ile Thr Met Pro His
            260                 265                 270

Ser Met Val Arg Leu Ser Ala Gly Arg Glu Ser Met Ser Asp Ala Thr
            275                 280                 285

Gln Ala Leu Cys Phe Leu Ala Gly Ala Asn Ser Ile Phe Thr Gly Asp
    290                 295                 300

Lys Leu Leu Thr Ala Gly Asn Ala Gly Asp Lys Asp Ala Ala Leu
305                 310                 315                 320

Phe Ala Arg Leu Gly Leu Thr Pro Met Ala Ala Glu Cys Lys Val Glu
                325                 330                 335

Leu Glu Ala Ala Glu
            340

<210> SEQ ID NO 25
<211> LENGTH: 1358
<212> TYPE: DNA
<213> ORGANISM: Sphingomonas sp.
<220> FEATURE:
<223> OTHER INFORMATION: Strain = SC42405
<221> NAME/KEY: CDS
<222> LOCATION: (152)..(1207)

<400> SEQUENCE: 25
```

| | |
|---|---|
| tgctgcgcct gctcggccac aacatgccgc cgctcggttc ttcgctggaa gcggcggaat | 60 |
| aaggatggcc acgctggatc gacgccgcgc ttgcccctat gaccgggggtt tggccgcgcg | 120 |
| tcatcccgcg cgcagaccgg ccgcctgagg a atg act atg act gac acc ccc<br>                                                     Met Thr Met Thr Asp Thr Pro<br>                                                      1                 5 | 172 |
| gcc atc act gca cgt acc gac tgg acc cgt gag gaa atc gcg gcg ctg<br>Ala Ile Thr Ala Arg Thr Asp Trp Thr Arg Glu Glu Ile Ala Ala Leu<br>          10                   15                  20 | 220 |
| ttc gac ctg ccg ttc acc gaa ctg gtg ttc cgc gca gcc gaa gtc cat<br>Phe Asp Leu Pro Phe Thr Glu Leu Val Phe Arg Ala Ala Glu Val His<br> 25                    30                   35 | 268 |
| cgc gcc agc cat ccg cac aac gaa gtg cag ctt tcc acg ctg ctt tcg<br>Arg Ala Ser His Pro His Asn Glu Val Gln Leu Ser Thr Leu Leu Ser<br> 40                    45                   50                  55 | 316 |
| atc aag acc ggc ggc tgc gtg gaa gac tgc ggc tat tgc tca cag tcg<br>Ile Lys Thr Gly Gly Cys Val Glu Asp Cys Gly Tyr Cys Ser Gln Ser<br>                 60                   65                   70 | 364 |
| gtt tcg gcc aac agc ggc gtc aag gcg acc aag ctg atg gaa gtg cag<br>Val Ser Ala Asn Ser Gly Val Lys Ala Thr Lys Leu Met Glu Val Gln<br>          75                   80                   85 | 412 |
| cag gtg ctg cag cgc gcg gcg cag gcg gcg gat cag ggc tct acc cgc<br>Gln Val Leu Gln Arg Ala Ala Gln Ala Ala Asp Gln Gly Ser Thr Arg<br>               90                   95                  100 | 460 |
| ttc tgc atg ggc gcc gcc tgg cgc aac ccc aag gac cgc gac atg ccc<br>Phe Cys Met Gly Ala Ala Trp Arg Asn Pro Lys Asp Arg Asp Met Pro<br>          105                  110                115 | 508 |
| gcc atc atc gag atg gtg aag ggc gtg cgc gcc atg ggc atg gaa acc<br>Ala Ile Ile Glu Met Val Lys Gly Val Arg Ala Met Gly Met Glu Thr<br>120                   125                130              135 | 556 |

-continued

```
tgc atg acg cgg ggc atg ctg acg ccc gat cag gcg gac atg ctc tcc    604
Cys Met Thr Arg Gly Met Leu Thr Pro Asp Gln Ala Asp Met Leu Ser
            140                 145                 150 gaa gcg ggt ctc gat tac tac aac cac aac atc gac acc tcg ccc gag    652
Glu Ala Gly Leu Asp Tyr Tyr Asn His Asn Ile Asp Thr Ser Pro Glu
        155                 160                 165 cgt tac gat cag gtg atc acc acg cgc acg atg gat gac cgc ctc gat    700
Arg Tyr Asp Gln Val Ile Thr Thr Arg Thr Met Asp Asp Arg Leu Asp
        170                 175                 180 acg ctg tcg aac gtg cgt atg gcg ggc atc aac gtc tgc tcc ggc ggc    748
Thr Leu Ser Asn Val Arg Met Ala Gly Ile Asn Val Cys Ser Gly Gly
    185                 190                 195 atc gtc ggc atg ggt gag acg cgc gcc gac cgc gtg ggc ttc gtt cac    796
Ile Val Gly Met Gly Glu Thr Arg Ala Asp Arg Val Gly Phe Val His
200                 205                 210                 215 acg ctg gcg acg ctg ccc gat cac ccg cag tcg gtg ccg gtc aac gcg    844
Thr Leu Ala Thr Leu Pro Asp His Pro Gln Ser Val Pro Val Asn Ala
                220                 225                 230 ctg gtt cct gtg aag ggc acc gtg ctg ggc gac atg ctg gcc gat acc    892
Leu Val Pro Val Lys Gly Thr Val Leu Gly Asp Met Leu Ala Asp Thr
            235                 240                 245 ccg ctt gcc aag atc gac gat gtg gaa ttc gtg cgc acc gtc gcg gtg    940
Pro Leu Ala Lys Ile Asp Asp Val Glu Phe Val Arg Thr Val Ala Val
        250                 255                 260 gcg cgc atc acc atg ccg ctg tcg atg gtg cgc ctc tcg gcc ggc cgc    988
Ala Arg Ile Thr Met Pro Leu Ser Met Val Arg Leu Ser Ala Gly Arg
    265                 270                 275 gaa tcg atg tcc gaa atg acg cag gcg atg tgc ttc atg gcc ggc gcg   1036
Glu Ser Met Ser Glu Met Thr Gln Ala Met Cys Phe Met Ala Gly Ala
280                 285                 290                 295 aac tcg atc ttc acc ggc gac aag ctg ctg acc gca ccg aac tcc ggc   1084
Asn Ser Ile Phe Thr Gly Asp Lys Leu Leu Thr Ala Pro Asn Ser Gly
                300                 305                 310 gac gac aac gac gcg gcg atg ttc gcc cgt ctc ggc atc aag ccg atg   1132
Asp Asp Asn Asp Ala Ala Met Phe Ala Arg Leu Gly Ile Lys Pro Met
            315                 320                 325 gcc atc gaa ctg acc ccg gcg caa gtc gaa gcc cag cgc atg ccc aag   1180
Ala Ile Glu Leu Thr Pro Ala Gln Val Glu Ala Gln Arg Met Pro Lys
        330                 335                 340 ggc tgc gcc aag ctg gaa gct gcg gaa taacgaatgg ggcaccgcgc         1227
Gly Cys Ala Lys Leu Glu Ala Ala Glu
    345                 350 acccttccat ccccgtcatg ctgaacttgt ttcagcatcc atttcgccgt tcggaccgat 1287 ggcctgtgcg gcgcgatgga ccctgagccg tcaggccagc ggagctaaac aagttcaggg 1347 ggacgatgag g                                                     1358

<210> SEQ ID NO 26
<211> LENGTH: 352
<212> TYPE: PRT
<213> ORGANISM: Sphingomonas sp.

<400> SEQUENCE: 26

Met Thr Met Thr Asp Thr Pro Ala Ile Thr Ala Arg Thr Asp Trp Thr
1               5                   10                  15

Arg Glu Glu Ile Ala Ala Leu Phe Asp Leu Pro Phe Thr Glu Leu Val
            20                  25                  30

Phe Arg Ala Ala Glu Val His Arg Ala Ser His Pro His Asn Glu Val
        35                  40                  45
```

```
Gln Leu Ser Thr Leu Ser Ile Lys Thr Gly Gly Cys Val Glu Asp
 50                  55                  60

Cys Gly Tyr Cys Ser Gln Ser Val Ser Ala Asn Ser Gly Val Lys Ala
 65                  70                  75                  80

Thr Lys Leu Met Glu Val Gln Val Leu Gln Arg Ala Ala Gln Ala
                 85                  90                  95

Ala Asp Gln Gly Ser Thr Arg Phe Cys Met Gly Ala Ala Trp Arg Asn
            100                 105                 110

Pro Lys Asp Arg Asp Met Pro Ala Ile Ile Glu Met Val Lys Gly Val
        115                 120                 125

Arg Ala Met Gly Met Glu Thr Cys Met Thr Arg Gly Met Leu Thr Pro
    130                 135                 140

Asp Gln Ala Asp Met Leu Ser Glu Ala Gly Leu Asp Tyr Tyr Asn His
145                 150                 155                 160

Asn Ile Asp Thr Ser Pro Glu Arg Tyr Asp Gln Val Ile Thr Thr Arg
                165                 170                 175

Thr Met Asp Asp Arg Leu Asp Thr Leu Ser Asn Val Arg Met Ala Gly
            180                 185                 190

Ile Asn Val Cys Ser Gly Gly Ile Val Gly Met Gly Glu Thr Arg Ala
        195                 200                 205

Asp Arg Val Gly Phe Val His Thr Leu Ala Thr Leu Pro Asp His Pro
    210                 215                 220

Gln Ser Val Pro Val Asn Ala Leu Val Pro Val Lys Gly Thr Val Leu
225                 230                 235                 240

Gly Asp Met Leu Ala Asp Thr Pro Leu Ala Lys Ile Asp Asp Val Glu
                245                 250                 255

Phe Val Arg Thr Val Ala Val Ala Arg Ile Thr Met Pro Leu Ser Met
            260                 265                 270

Val Arg Leu Ser Ala Gly Arg Glu Ser Met Ser Glu Met Thr Gln Ala
        275                 280                 285

Met Cys Phe Met Ala Gly Ala Asn Ser Ile Phe Thr Gly Asp Lys Leu
    290                 295                 300

Leu Thr Ala Pro Asn Ser Gly Asp Asp Asn Asp Ala Ala Met Phe Ala
305                 310                 315                 320

Arg Leu Gly Ile Lys Pro Met Ala Ile Glu Leu Thr Pro Ala Gln Val
                325                 330                 335

Glu Ala Gln Arg Met Pro Lys Gly Cys Ala Lys Leu Glu Ala Ala Glu
            340                 345                 350

<210> SEQ ID NO 27
<211> LENGTH: 341
<212> TYPE: PRT
<213> ORGANISM: Sphingomonas paucimobilis
<220> FEATURE:
<223> OTHER INFORMATION: Strain = JCM7511

<400> SEQUENCE: 27

Met Thr Thr Thr Pro Ala Leu Ser Ser Glu Ala Thr Pro Arg Thr Asp
 1               5                  10                  15

Trp Thr Arg Ala Glu Ile Ala Ala Leu Phe Asp Leu Pro Phe Thr Glu
                 20                  25                  30

Leu Leu Phe Arg Ala Ala Glu Val His Arg Ala His His Ala Ala Asp
             35                  40                  45

Gln Val Gln Leu Ser Thr Leu Leu Ser Ile Lys Thr Gly Gly Cys Pro
 50                  55                  60
```

```
Glu Asp Cys Gly Tyr Cys Ser Gln Ser Thr His Ala Asp Thr Gly Leu
 65                  70                  75                  80

Lys Ala Thr Lys Leu Met Asp Pro Arg Ala Val Leu Gln Ala Ala Ala
                 85                  90                  95

Gln Ala Lys Asp His Gly Ser Thr Arg Phe Cys Met Gly Ala Ala Trp
            100                 105                 110

Arg Asn Pro Lys Asp Arg Asp Met Pro Ala Ile Val Glu Met Val Lys
        115                 120                 125

Gly Val Arg Ala Met Gly Met Glu Thr Cys Met Thr Leu Gly Met Leu
130                 135                 140

Thr Asp Ala Gln Ala Gln Thr Leu Ala Glu Ala Gly Leu Asp Tyr Tyr
145                 150                 155                 160

Asn His Asn Ile Asp Thr Ser Pro Glu Arg Tyr Gly Asp Val Ile Thr
                165                 170                 175

Thr Arg Ser Phe Gly Glu Arg Leu Glu Thr Leu Glu His Val Arg Asp
            180                 185                 190

Ala Gly Ile Asn Val Cys Cys Gly Gly Ile Val Gly Met Gly Glu Thr
        195                 200                 205

Arg Gly Asp Arg Val Gly Phe Ile His Ala Leu Ala Thr Leu Pro Val
210                 215                 220

His Pro Gly Ser Val Pro Val Asn Ala Leu Val Leu Val Lys Gly Thr
225                 230                 235                 240

Val Leu Gly Asp Met Leu Ala Asp Thr Pro Leu Ala Lys Ile Asp Asp
                245                 250                 255

Ile Glu Phe Val Arg Thr Val Ala Val Ala Arg Ile Thr Met Pro His
            260                 265                 270

Ser Met Val Arg Leu Ser Ala Gly Arg Glu Ser Met Ser Asp Ala Thr
        275                 280                 285

Gln Ala Leu Cys Phe Leu Ala Gly Ala Asn Ser Ile Phe Thr Gly Asp
290                 295                 300

Lys Leu Leu Thr Ala Gly Asn Ala Gly Asp Asp Lys Asp Ala Ala Leu
305                 310                 315                 320

Phe Ala Arg Leu Gly Leu Thr Pro Met Ala Ala Glu Cys Lys Val Glu
                325                 330                 335

Leu Glu Ala Ala Glu
            340

<210> SEQ ID NO 28
<211> LENGTH: 1336
<212> TYPE: DNA
<213> ORGANISM: Sphingomonas paucimobilis
<220> FEATURE:
<223> OTHER INFORMATION: Strain = JCM7511
<221> NAME/KEY: CDS
<222> LOCATION: (151)..(1173)

<400> SEQUENCE: 28
tctagaacag gactatcagg cactctacga tgccggggta caggcgattt tcggtcccgg    60
caccaatctt gtgaaagcgg ccgaggatgt gctaaggctg ctgggacata atatgccgcc   120
cgaggcgggc gaatgacagg acgacacgtg atg acg acg aca ccc gcg ctg agc   174
                                 Met Thr Thr Thr Pro Ala Leu Ser
                                  1               5 tcc gag gcg acc ccg cgc acc gac tgg acc cgc gcc gag atc gcc gcg   222
Ser Glu Ala Thr Pro Arg Thr Asp Trp Thr Arg Ala Glu Ile Ala Ala
         10                  15                  20
```

```
                                                -continued ctg ttc gac ctg ccc ttc acc gag ctg ttg ttc cgc gcg gcc gag gtg      270
Leu Phe Asp Leu Pro Phe Thr Glu Leu Leu Phe Arg Ala Ala Glu Val
 25              30                  35                  40 cac cgc gcg cat cac gcc gcc gat cag gtt cag ctg tcg acg ctg ttg      318
His Arg Ala His His Ala Ala Asp Gln Val Gln Leu Ser Thr Leu Leu
                 45                  50                  55 tcg atc aag acg ggc ggc tgc ccc gag gat tgc ggc tat tgc agc cag      366
Ser Ile Lys Thr Gly Gly Cys Pro Glu Asp Cys Gly Tyr Cys Ser Gln
             60                  65                  70 tcg acc cat gcc gat acc ggg ctg aag gcg acc aag ctg atg gac ccg      414
Ser Thr His Ala Asp Thr Gly Leu Lys Ala Thr Lys Leu Met Asp Pro
         75                  80                  85 cgc gcc gtg ctg cag gcg gcg gcg cag gcc aag gat cac ggc tcg acg      462
Arg Ala Val Leu Gln Ala Ala Ala Gln Ala Lys Asp His Gly Ser Thr
     90                  95                 100 cgc ttc tgc atg ggc gcg gcc tgg cgc aac ccc aag gat cgc gac atg      510
Arg Phe Cys Met Gly Ala Ala Trp Arg Asn Pro Lys Asp Arg Asp Met
105                 110                 115                 120 ccc gcc atc gtg gag atg gtg aag ggc gtg cgc gcc atg ggc atg gaa      558
Pro Ala Ile Val Glu Met Val Lys Gly Val Arg Ala Met Gly Met Glu
                125                 130                 135 acc tgc atg acg ctg ggc atg ctg acc gat gca cag gcg cag acg ctc      606
Thr Cys Met Thr Leu Gly Met Leu Thr Asp Ala Gln Ala Gln Thr Leu
            140                 145                 150 gcc gag gcg ggg ctg gac tat tac aat cac aat atc gac acg tcg ccc      654
Ala Glu Ala Gly Leu Asp Tyr Tyr Asn His Asn Ile Asp Thr Ser Pro
        155                 160                 165 gag cgt tat ggc gac gtc atc acc acg cgc agc ttc ggc gag cgg ttg      702
Glu Arg Tyr Gly Asp Val Ile Thr Thr Arg Ser Phe Gly Glu Arg Leu
    170                 175                 180 gag acg ttg gag cat gtc cgc gat gcc ggc atc aat gta tgc tgt ggc      750
Glu Thr Leu Glu His Val Arg Asp Ala Gly Ile Asn Val Cys Cys Gly
185                 190                 195                 200 ggt att gtc ggc atg ggt gag acg cgc ggc gac cgg gtc ggc ttc atc      798
Gly Ile Val Gly Met Gly Glu Thr Arg Gly Asp Arg Val Gly Phe Ile
                205                 210                 215 cat gcg ctt gcc acc ctg ccg gtc cat ccg ggc agc gtg ccg gtg aac      846
His Ala Leu Ala Thr Leu Pro Val His Pro Gly Ser Val Pro Val Asn
            220                 225                 230 gcg ctg gtg ctg gtc aag ggc acg gta ttg ggc gat atg ttg gcc gac      894
Ala Leu Val Leu Val Lys Gly Thr Val Leu Gly Asp Met Leu Ala Asp
        235                 240                 245 acg ccg ctg gcc aag atc gac gat atc gaa ttc gtc cgc acc gtc gcg      942
Thr Pro Leu Ala Lys Ile Asp Asp Ile Glu Phe Val Arg Thr Val Ala
    250                 255                 260 gtt gcg cgc atc acc atg ccg cat tcg atg gtc cgc ctg tcg gcg ggg      990
Val Ala Arg Ile Thr Met Pro His Ser Met Val Arg Leu Ser Ala Gly
265                 270                 275                 280 cgc gag agc atg tcg gat gcc acc cag gct ttg tgc ttc ctg gcg ggc     1038
Arg Glu Ser Met Ser Asp Ala Thr Gln Ala Leu Cys Phe Leu Ala Gly
                285                 290                 295 gcg aac tcg atc ttc acc ggc gac aag ctg ctg act gcg ggc aat gcg     1086
Ala Asn Ser Ile Phe Thr Gly Asp Lys Leu Leu Thr Ala Gly Asn Ala
            300                 305                 310 ggc gac gac aag gac gca gcg ctc ttc gcc cgg ctg ggg ctc acg ccc     1134
Gly Asp Asp Lys Asp Ala Ala Leu Phe Ala Arg Leu Gly Leu Thr Pro
        315                 320                 325 atg gcg gcg gag tgc aag gtg gaa ttg gaa gcg gcg gag taaacaggct     1183
Met Ala Ala Glu Cys Lys Val Glu Leu Glu Ala Ala Glu
    330                 335                 340
```

-continued

```
tcgccggttg tccccggcga aagccggagc ccagttgcgg tgaagtaggg gtggtgcgcc   1243
acccgaatgg cattcgacac ggaccaacga cataatagga gaggtatccc cgtgttccag   1303
aaaatcctga tcgccaatcg cggggaatct aga                               1336
```

<210> SEQ ID NO 29
<211> LENGTH: 341
<212> TYPE: PRT
<213> ORGANISM: Sphingomonas paucimobilis

<400> SEQUENCE: 29

```
Met Thr Thr Thr Pro Ala Leu Ser Ser Glu Ala Thr Pro Arg Thr Asp
 1               5                  10                  15

Trp Thr Arg Ala Glu Ile Ala Ala Leu Phe Asp Leu Pro Phe Thr Glu
             20                  25                  30

Leu Leu Phe Arg Ala Ala Glu Val His Arg Ala His His Ala Ala Asp
         35                  40                  45

Gln Val Gln Leu Ser Thr Leu Leu Ser Ile Lys Thr Gly Gly Cys Pro
     50                  55                  60

Glu Asp Cys Gly Tyr Cys Ser Gln Ser Thr His Ala Asp Thr Gly Leu
 65                  70                  75                  80

Lys Ala Thr Lys Leu Met Asp Pro Arg Ala Val Leu Gln Ala Ala Ala
                 85                  90                  95

Gln Ala Lys Asp His Gly Ser Thr Arg Phe Cys Met Gly Ala Ala Trp
            100                 105                 110

Arg Asn Pro Lys Asp Arg Asp Met Pro Ala Ile Val Glu Met Val Lys
        115                 120                 125

Gly Val Arg Ala Met Gly Met Glu Thr Cys Met Thr Leu Gly Met Leu
    130                 135                 140

Thr Asp Ala Gln Ala Gln Thr Leu Ala Glu Ala Gly Leu Asp Tyr Tyr
145                 150                 155                 160

Asn His Asn Ile Asp Thr Ser Pro Glu Arg Tyr Gly Asp Val Ile Thr
                165                 170                 175

Thr Arg Ser Phe Gly Glu Arg Leu Glu Thr Leu Glu His Val Arg Asp
            180                 185                 190

Ala Gly Ile Asn Val Cys Cys Gly Gly Ile Val Gly Met Gly Glu Thr
        195                 200                 205

Arg Gly Asp Arg Val Gly Phe Ile His Ala Leu Ala Thr Leu Pro Val
    210                 215                 220

His Pro Gly Ser Val Pro Val Asn Ala Leu Val Leu Val Lys Gly Thr
225                 230                 235                 240

Val Leu Gly Asp Met Leu Ala Asp Thr Pro Leu Ala Lys Ile Asp Asp
                245                 250                 255

Ile Glu Phe Val Arg Thr Val Ala Val Ala Arg Ile Thr Met Pro His
            260                 265                 270

Ser Met Val Arg Leu Ser Ala Gly Arg Glu Ser Met Ser Asp Ala Thr
        275                 280                 285

Gln Ala Leu Cys Phe Leu Ala Gly Ala Asn Ser Ile Phe Thr Gly Asp
    290                 295                 300

Lys Leu Leu Thr Ala Gly Asn Ala Gly Asp Asp Lys Asp Ala Ala Leu
305                 310                 315                 320

Phe Ala Arg Leu Gly Leu Thr Pro Met Ala Ala Glu Cys Lys Val Glu
                325                 330                 335

Leu Glu Ala Ala Glu
            340
```

```
<210> SEQ ID NO 30
<211> LENGTH: 283
<212> TYPE: PRT
<213> ORGANISM: Sphingomonas paucimobilis
<220> FEATURE:
<223> OTHER INFORMATION: Strain = JCM7511

<400> SEQUENCE: 30
```

Met Ala Glu Asp Ser Pro Ser Arg Ala Arg Ile Ala Gln Ala Phe Asp
 1               5                  10                  15

Ala Ala Ala Ala Tyr Asp Ala Tyr Ala Val Val Gln Arg Gln Val Ala
                20                  25                  30

Ala Trp Leu Ala Glu Arg Ile Val Ala Val Pro Pro Arg Pro Arg
            35                  40                  45

Val Leu Glu Val Gly Cys Gly Thr Gly Phe Leu Thr Gln Ala Ala Trp
    50                  55                  60

Pro Arg Leu Asp Arg Pro Glu Trp Leu Met Thr Asp Ile Ala Pro Glu
65                  70                  75                  80

Met Leu Ala Arg Gly Arg Ala Gln Met Pro Asp Leu Cys Ala Arg Val
                85                  90                  95

Met Asp Gly Glu Arg Pro Asp Leu Ala Gly Glu Ala Pro Phe Asp Leu
            100                 105                 110

Ile Val Ser Ser Leu Ala Val Gln Trp Phe Ser Asp Leu Glu Gly Gly
        115                 120                 125

Leu Gln Arg Leu Ala Ala Leu Leu Ala Pro Gly Gly Arg Met Leu Val
    130                 135                 140

Thr Thr Leu Ala Gln Gly Thr Phe Ala Gly Trp His Ala Ala His Arg
145                 150                 155                 160

Ala Glu Gly Tyr Glu Ala Gly Ser His Ala Tyr Pro Thr Val Glu Ala
                165                 170                 175

Leu Ala Ala Met Ala Leu Pro Gly Leu Gly Val Ala Thr Arg Arg Phe
            180                 185                 190

Glu Gln Arg His Glu Thr Ala Ala Asp Phe Met Arg Ala Leu Arg Ala
        195                 200                 205

Ile Gly Ala Gly Thr Pro Arg Val Gly His Arg Pro Ile Pro Pro Gly
    210                 215                 220

Ala Met Arg Arg Ile Ala Lys Arg Phe Glu Val Gly Gly Ala Val Ala
225                 230                 235                 240

Thr Tyr Glu Val Ala Leu Met Asp Ile Pro Asn Pro Val Gln Pro Glu
                245                 250                 255

Arg Ser Arg Arg Pro Arg Ala Thr Arg Glu Ala Gly Arg Val Leu Arg
            260                 265                 270

Phe Arg Ser Ala Arg Thr Glu Val Gly Gly Lys
        275                 280

```
<210> SEQ ID NO 31
<211> LENGTH: 254
<212> TYPE: PRT
<213> ORGANISM: Sphingomonas sp.
<220> FEATURE:
<223> OTHER INFORMATION: Strain = SC42405

<400> SEQUENCE: 31
```

Met Asn Ala Pro Arg Glu Arg Val Ser Arg Ala Phe Ala Ala Pro
 1               5                  10                  15

Asp Tyr Asp Gly His Ala Arg Ile Gln Arg Glu Val Ala Gln Thr Leu
                20                  25                  30

```
Ala Ala Arg Ile Ala Ala Leu Asp Leu Pro Pro Asn Pro Arg Val Leu
         35                  40                  45

Glu Ile Gly Cys Gly Thr Gly Phe Leu Thr Gln Ala Leu Ala Gly Leu
     50                  55                  60

Asp Gly Asp Trp Leu Val Thr Asp Leu Ala Pro Glu Met Leu Glu Arg
 65                  70                  75                  80

Cys Arg Ser Arg Leu Gly Glu Ser Ala Arg His Arg Phe Ala Val Leu
                 85                  90                  95

Asp Gly Glu Tyr Gly Ala Pro Asp Gly Ala Pro Phe Asp Leu Ile Cys
            100                 105                 110

Ser Ser Leu Ala Val Gln Trp Phe Asp Asp Thr Pro Ala Ala Leu Ala
        115                 120                 125

Arg Met Ala Gly Trp Leu Ala Pro Gly Gly His Leu Met Val Thr Thr
    130                 135                 140

Leu Gly Pro Gly Ser Phe Ala Glu Trp Arg Ala Ala His Glu Ala Glu
145                 150                 155                 160

Gly Leu Glu Pro Gly Thr Pro His Phe Ala Asp Ile Ala Ala Phe Gly
                165                 170                 175

Asp Leu Val His Ala Val Glu His Pro Val Glu His His Ala Asp Pro
            180                 185                 190

Leu Ala Phe Leu His Ala Leu Lys Ala Ile Gly Ala Gln Thr Ala Glu
        195                 200                 205

Ala Gly His Arg Pro Leu Ser Pro Gly Gln Leu Arg Arg Val Met Ala
    210                 215                 220

Arg Phe Ala Gln Ser Gly Cys Pro Gln Asn Gly Cys Lys Val Thr Tyr
225                 230                 235                 240

Glu Val Val Thr Cys His Leu His Arg Glu Ser Ser Leu Ser
                245                 250
```

<210> SEQ ID NO 32
<211> LENGTH: 1582
<212> TYPE: DNA
<213> ORGANISM: Sphingomonas paucimobilis
<220> FEATURE:
<223> OTHER INFORMATION: Strain = JCM7511
<221> NAME/KEY: CDS
<222> LOCATION: (489)..(1337)

<400> SEQUENCE: 32

```
gatctgggtc gcggcgctgt tggcggcgtt gttgccggtc gatcggctgg tcgcgcccga      60
ttgcgagtcg ggctggttcg atcaggtcgt ggtgcgcggg gtgtcgctgc cgtcgtcat     120 gctgttgcgg atcgtcgcgc attggctggc ctttgcgccg ccgctgatgc tggcggcgat     180
ggtcgcaggc ggtttgttcg ggctggatgg cgccgcgttg gtgagggtcg agaccggatt     240
gctgctcggt acgccgggc tcgccgcgct ggcggtggcg acggggcgc tgacggcggg     300 cttgcgcggt gcgggagcgg tggcggggtt gctgctgtta ccgctcgccc tgccgctgct     360
gatcgatctt cggggctagc gatgacggca tgggcggggc caagctgctc gccgccgtgt     420
cgctgttgct ggtcgcgggt gcgccctggc tggcggcggc ggcgatccgg tcggtgcgcg     480 actgagcc atg gcc gaa gac agt cca tcg cgc gcg cgg atc gcg cag gcc      530
         Met Ala Glu Asp Ser Pro Ser Arg Ala Arg Ile Ala Gln Ala
          1               5                  10 ttt gac gcg gcg gcg gcc tat gac gcc tat gcg gtg gtg cag cgc caa      578
Phe Asp Ala Ala Ala Ala Tyr Asp Ala Tyr Ala Val Val Gln Arg Gln
 15                  20                  25                  30
```

| | | |
|---|---|---|
| gtg gcc gcg tgg cta gcc gaa cga atc gtc gcg gtc gcc ccg ccg agg<br>Val Ala Ala Trp Leu Ala Glu Arg Ile Val Ala Val Ala Pro Pro Arg<br>35 40 45 | | 626 |
| ccc cgc gtg ctg gag gtc ggg tgc ggc aca ggc ttc ctg aca cag gcg<br>Pro Arg Val Leu Glu Val Gly Cys Gly Thr Gly Phe Leu Thr Gln Ala<br>50 55 60 | | 674 |
| gca tgg ccc cgg ctt gat cgc ccc gaa tgg ttg atg acc gat atc gca<br>Ala Trp Pro Arg Leu Asp Arg Pro Glu Trp Leu Met Thr Asp Ile Ala<br>65 70 75 | | 722 |
| ccc gag atg ctg gcc cgg ggc agg gcg cag atg ccg gat ctg tgt gcg<br>Pro Glu Met Leu Ala Arg Gly Arg Ala Gln Met Pro Asp Leu Cys Ala<br>80 85 90 | | 770 |
| cgg gtg atg gat ggc gag cgc ccc gat ctg gcg ggc gaa gcg ccg ttc<br>Arg Val Met Asp Gly Glu Arg Pro Asp Leu Ala Gly Glu Ala Pro Phe<br>95 100 105 110 | | 818 |
| gac ctg atc gtc agc agc ctg gcg gtg cag tgg ttt tcc gat ctg gag<br>Asp Leu Ile Val Ser Ser Leu Ala Val Gln Trp Phe Ser Asp Leu Glu<br>115 120 125 | | 866 |
| ggc ggc ctg cag cgg ctg gcg gcg ctc ctc gcc cct ggc ggg cgg atg<br>Gly Gly Leu Gln Arg Leu Ala Ala Leu Leu Ala Pro Gly Gly Arg Met<br>130 135 140 | | 914 |
| ctg gtg acg act ctg gcg caa ggg aca ttc gcc ggc tgg cat gcc gcg<br>Leu Val Thr Thr Leu Ala Gln Gly Thr Phe Ala Gly Trp His Ala Ala<br>145 150 155 | | 962 |
| cat cgg gcg gag gga tat gag gcg ggg agt cac gcc tat cca acg gtc<br>His Arg Ala Glu Gly Tyr Glu Ala Gly Ser His Ala Tyr Pro Thr Val<br>160 165 170 | | 1010 |
| gag gcg ctc gcg gcc atg gcg ttg ccg ggg ctt ggg gtc gcc acg cga<br>Glu Ala Leu Ala Ala Met Ala Leu Pro Gly Leu Gly Val Ala Thr Arg<br>175 180 185 190 | | 1058 |
| cgc ttc gag cag cgg cac gag acg gcg gcg gac ttc atg cgc gca cta<br>Arg Phe Glu Gln Arg His Glu Thr Ala Ala Asp Phe Met Arg Ala Leu<br>195 200 205 | | 1106 |
| cgg gcg atc ggg gcg ggg aca ccg cgt gtt ggg cac cgc ccg atc ccg<br>Arg Ala Ile Gly Ala Gly Thr Pro Arg Val Gly His Arg Pro Ile Pro<br>210 215 220 | | 1154 |
| ccg ggc gcg atg cgg cgg atc gcg aag cgc ttt gag gta ggc ggg gcg<br>Pro Gly Ala Met Arg Arg Ile Ala Lys Arg Phe Glu Val Gly Gly Ala<br>225 230 235 | | 1202 |
| gtg gcg acc tat gag gtc gcg ttg atg gac att ccc aac ccc gtt cag<br>Val Ala Thr Tyr Glu Val Ala Leu Met Asp Ile Pro Asn Pro Val Gln<br>240 245 250 | | 1250 |
| cct gag cga agt cga agg cca cgc gcg acg cga gag gcg ggg cgt gtg<br>Pro Glu Arg Ser Arg Arg Pro Arg Ala Thr Arg Glu Ala Gly Arg Val<br>255 260 265 270 | | 1298 |
| ctt cga ttt cgc tca gca cga acg gag gtt gga ggt aag taggcttggg<br>Leu Arg Phe Arg Ser Ala Arg Thr Glu Val Gly Gly Lys<br>275 280 | | 1347 |
| ttggcgttta tcggctccac cgcgcccaga tggccgtggg caggatcagc ccgcgtgctt | | 1407 |
| cctcgcgcac accgagttcg ccgcattcga ccttgcccgg caggtcgccc atcacttggc | | 1467 |
| ggagcatctc gccgatcgcc agcgccgaca tgcgcaccgc atagacggtc aggaacagga | | 1527 |
| agcgcgaatt cgcgtcgagc agcttgcggc aatcggcgat caggccgggc agatc | | 1582 |

<210> SEQ ID NO 33
<211> LENGTH: 283
<212> TYPE: PRT
<213> ORGANISM: Sphingomonas paucimobilis

<400> SEQUENCE: 33

| | | | | | | | | | | | | | | | |
|---|---|---|---|---|---|---|---|---|---|---|---|---|---|---|---|
|Met|Ala|Glu|Asp|Ser|Pro|Ser|Arg|Ala|Arg|Ile|Ala|Gln|Ala|Phe|Asp|
|1| | |  |5| | | |10| | | | |15| | |
|Ala|Ala|Ala|Ala|Tyr|Asp|Ala|Tyr|Ala|Val|Val|Gln|Arg|Gln|Val|Ala|
| | | | |20| | | |25| | | | |30| | |
|Ala|Trp|Leu|Ala|Glu|Arg|Ile|Val|Ala|Val|Ala|Pro|Pro|Arg|Pro|Arg|
| | |35| | | | |40| | | | |45| | | |
|Val|Leu|Glu|Val|Gly|Cys|Gly|Thr|Gly|Phe|Leu|Thr|Gln|Ala|Ala|Trp|
| |50| | | | |55| | | | |60| | | | |
|Pro|Arg|Leu|Asp|Arg|Pro|Glu|Trp|Leu|Met|Thr|Asp|Ile|Ala|Pro|Glu|
|65| | | | |70| | | | |75| | | | |80|
|Met|Leu|Ala|Arg|Gly|Arg|Ala|Gln|Met|Pro|Asp|Leu|Cys|Ala|Arg|Val|
| | | | |85| | | | |90| | | | |95| |
|Met|Asp|Gly|Glu|Arg|Pro|Asp|Leu|Ala|Gly|Glu|Ala|Pro|Phe|Asp|Leu|
| | | |100| | | | |105| | | | |110| | |
|Ile|Val|Ser|Ser|Leu|Ala|Val|Gln|Trp|Phe|Ser|Asp|Leu|Glu|Gly|Gly|
| | |115| | | | |120| | | | |125| | | |
|Leu|Gln|Arg|Leu|Ala|Ala|Leu|Leu|Ala|Pro|Gly|Gly|Arg|Met|Leu|Val|
| |130| | | | |135| | | | |140| | | | |
|Thr|Thr|Leu|Ala|Gln|Gly|Thr|Phe|Ala|Gly|Trp|His|Ala|Ala|His|Arg|
|145| | | | |150| | | | |155| | | | |160|
|Ala|Glu|Gly|Tyr|Glu|Ala|Gly|Ser|His|Ala|Tyr|Pro|Thr|Val|Glu|Ala|
| | | | |165| | | | |170| | | | |175| |
|Leu|Ala|Ala|Met|Ala|Leu|Pro|Gly|Leu|Gly|Val|Ala|Thr|Arg|Arg|Phe|
| | | |180| | | | |185| | | | |190| | |
|Glu|Gln|Arg|His|Glu|Thr|Ala|Ala|Asp|Phe|Met|Arg|Ala|Leu|Arg|Ala|
| | |195| | | | |200| | | | |205| | | |
|Ile|Gly|Ala|Gly|Thr|Pro|Arg|Val|Gly|His|Arg|Pro|Ile|Pro|Pro|Gly|
| |210| | | | |215| | | | |220| | | | |
|Ala|Met|Arg|Arg|Ile|Ala|Lys|Arg|Phe|Glu|Val|Gly|Gly|Ala|Val|Ala|
|225| | | | |230| | | | |235| | | | |240|
|Thr|Tyr|Glu|Val|Ala|Leu|Met|Asp|Ile|Pro|Asn|Pro|Val|Gln|Pro|Glu|
| | | | |245| | | | |250| | | | |255| |
|Arg|Ser|Arg|Arg|Pro|Arg|Ala|Thr|Arg|Glu|Ala|Gly|Arg|Val|Leu|Arg|
| | | |260| | | | |265| | | | |270| | |
|Phe|Arg|Ser|Ala|Arg|Thr|Glu|Val|Gly|Gly|Lys| | | | | |
| | |275| | | | |280| | | | | | | | |

<210> SEQ ID NO 34
<211> LENGTH: 971
<212> TYPE: DNA
<213> ORGANISM: Sphingomonas sp.
<220> FEATURE:
<223> OTHER INFORMATION: Strain = SC42405
<221> NAME/KEY: CDS
<222> LOCATION: (210)..(968)

<400> SEQUENCE: 34

```
ttgcgcgatg aggaggccac cttgcccgcc gtccccatca tctcgcttca aggcgcgcgc      60
gacccgcttc tgcccgaagc gatgcgcgca catgtcttcc ggaacgccgc cgtgcgccgg     120
atcgaatgcg agaccggagg gcacctcctc ccgctcgaag tgccggaatt ctgcgcgcaa     180
gccgtgcgcg acatgatcga gacgctggc atg aac gcc ccc cgc gag cgc gtc      233
                                 Met Asn Ala Pro Arg Glu Arg Val
                                  1               5
```

```
agc cgc gcc ttt gcc gcc gcg ccc gac tac gac ggc cat gcc cgc atc       281
Ser Arg Ala Phe Ala Ala Ala Pro Asp Tyr Asp Gly His Ala Arg Ile
    10                  15                  20 cag cgt gag gtc gca caa aca ctc gcc gcc cgg atc gcc gcg ctc gac       329
Gln Arg Glu Val Ala Gln Thr Leu Ala Ala Arg Ile Ala Ala Leu Asp
25                  30                  35                  40 ctg cct cca aac ccg cgc gtg ctg gag atc ggc tgc ggc acc ggt ttt       377
Leu Pro Pro Asn Pro Arg Val Leu Glu Ile Gly Cys Gly Thr Gly Phe
                45                  50                  55 ctc acg cag gcg ctg gcc ggg ctg gat ggc gac tgg ctc gtc acc gat       425
Leu Thr Gln Ala Leu Ala Gly Leu Asp Gly Asp Trp Leu Val Thr Asp
            60                  65                  70 ctt gcg ccc gaa atg ctg gag cgc tgt cgc agc cgc ctg ggc gaa agc       473
Leu Ala Pro Glu Met Leu Glu Arg Cys Arg Ser Arg Leu Gly Glu Ser
        75                  80                  85 gcc cgg cac cgc ttt gcc gtg ctc gat ggc gaa tat ggc gca ccg gac       521
Ala Arg His Arg Phe Ala Val Leu Asp Gly Glu Tyr Gly Ala Pro Asp
    90                  95                  100 ggc gca ccg ttc gac ctg atc tgc tcc agc ctc gcc gtg caa tgg ttc       569
Gly Ala Pro Phe Asp Leu Ile Cys Ser Ser Leu Ala Val Gln Trp Phe
105                 110                 115                 120 gac gat acc ccg gcc gcc ctc gcc cgc atg gca ggc tgg ctg gca ccg       617
Asp Asp Thr Pro Ala Ala Leu Ala Arg Met Ala Gly Trp Leu Ala Pro
                125                 130                 135 ggc ggg cac ctc atg gtg acg aca ctc ggc ccc ggc agc ttc gcc gaa       665
Gly Gly His Leu Met Val Thr Thr Leu Gly Pro Gly Ser Phe Ala Glu
            140                 145                 150 tgg cgc gcc gcg cat gaa gcg gag ggg ctg gaa ccc ggc acg ccc cac       713
Trp Arg Ala Ala His Glu Ala Glu Gly Leu Glu Pro Gly Thr Pro His
        155                 160                 165 ttc gcg gac atc gcc gcc ttc ggc gac ctc gtc cac gcg gtc gag cac       761
Phe Ala Asp Ile Ala Ala Phe Gly Asp Leu Val His Ala Val Glu His
    170                 175                 180 ccc gtc gag cat cac gcc gat ccg ctg gcc ttc ctc cac gcc ctc aag       809
Pro Val Glu His His Ala Asp Pro Leu Ala Phe Leu His Ala Leu Lys
185                 190                 195                 200 gcc atc ggc gcg cag acc gcc gaa gcc gga cac cgc ccc ctt tcc ccc       857
Ala Ile Gly Ala Gln Thr Ala Glu Ala Gly His Arg Pro Leu Ser Pro
                205                 210                 215 ggc cag ctt cgc cgc gtc atg gca cgt ttc gcc caa agc gga tgc ccc       905
Gly Gln Leu Arg Arg Val Met Ala Arg Phe Ala Gln Ser Gly Cys Pro
            220                 225                 230 caa aac gga tgc aaa gtg act tac gaa gtc gtg acc tgc cac cta cac       953
Gln Asn Gly Cys Lys Val Thr Tyr Glu Val Val Thr Cys His Leu His
        235                 240                 245 cga gaa tcg agc ctt tca                                                971
Arg Glu Ser Ser Leu
        250

<210> SEQ ID NO 35
<211> LENGTH: 253
<212> TYPE: PRT
<213> ORGANISM: Sphingomonas sp.

<400> SEQUENCE: 35

Met Asn Ala Pro Arg Glu Arg Val Ser Arg Ala Phe Ala Ala Ala Pro
1               5                   10                  15

Asp Tyr Asp Gly His Ala Arg Ile Gln Arg Glu Val Ala Gln Thr Leu
            20                  25                  30
```

```
Ala Ala Arg Ile Ala Ala Leu Asp Leu Pro Pro Asn Pro Arg Val Leu
        35                  40                  45
Glu Ile Gly Cys Gly Thr Gly Phe Leu Thr Gln Ala Leu Ala Gly Leu
 50                  55                  60
Asp Gly Asp Trp Leu Val Thr Asp Leu Ala Pro Glu Met Leu Glu Arg
 65                  70                  75                  80
Cys Arg Ser Arg Leu Gly Glu Ser Ala Arg His Arg Phe Ala Val Leu
                85                  90                  95
Asp Gly Glu Tyr Gly Ala Pro Asp Gly Ala Pro Phe Asp Leu Ile Cys
                100                 105                 110
Ser Ser Leu Ala Val Gln Trp Phe Asp Asp Thr Pro Ala Ala Leu Ala
        115                 120                 125
Arg Met Ala Gly Trp Leu Ala Pro Gly Gly His Leu Met Val Thr Thr
130                 135                 140
Leu Gly Pro Gly Ser Phe Ala Glu Trp Arg Ala Ala His Glu Ala Glu
145                 150                 155                 160
Gly Leu Glu Pro Gly Thr Pro His Phe Ala Asp Ile Ala Ala Phe Gly
                165                 170                 175
Asp Leu Val His Ala Val Glu His Pro Val Glu His His Ala Asp Pro
                180                 185                 190
Leu Ala Phe Leu His Ala Leu Lys Ala Ile Gly Ala Gln Thr Ala Glu
        195                 200                 205
Ala Gly His Arg Pro Leu Ser Pro Gly Gln Leu Arg Arg Val Met Ala
210                 215                 220
Arg Phe Ala Gln Ser Gly Cys Pro Gln Asn Gly Cys Lys Val Thr Tyr
225                 230                 235                 240
Glu Val Val Thr Cys His Leu His Arg Glu Ser Ser Leu
                245                 250

<210> SEQ ID NO 36
<211> LENGTH: 150
<212> TYPE: DNA
<213> ORGANISM: Sphingomonas paucimobilis
<220> FEATURE:
<223> OTHER INFORMATION: Strain = JCM7511

<400> SEQUENCE: 36
tctagaacag gactatcagg cactctacga tgccgggta caggcgattt tcggtcccgg      60
caccaatctt gtgaaagcgg ccgaggatgt gctaaggctg ctgggacata atatgccgcc    120
cgaggcgggc gaatgacagg acgacacgtg                                     150

<210> SEQ ID NO 37
<211> LENGTH: 201
<212> TYPE: DNA
<213> ORGANISM: Sphingomonas sp.
<220> FEATURE:
<223> OTHER INFORMATION: Strain = SC42405

<400> SEQUENCE: 37
accggaatga caggcggaca gcagcaatag ggcggcaaga gagagcggca gggatcgcat      60
cagacgggca tccttcggtt tttcctttgc cgttccaacg cgcgaggaag gcggcggctt    120
cacgtcccgc cgcgaaatcg atgcccctcc cggccagcca agcattgtgc cggacgcccg    180
cttgccatac gggcagggc g                                               201

<210> SEQ ID NO 38
<211> LENGTH: 28
```

```
<212> TYPE: DNA
<213> ORGANISM: Artificial Sequence
<220> FEATURE:
<223> OTHER INFORMATION: Description of Artificial Sequence:Primer BF

<400> SEQUENCE: 38
attctagaac aggactatca ggcactct                                         28

<210> SEQ ID NO 39
<211> LENGTH: 28
<212> TYPE: DNA
<213> ORGANISM: Artificial Sequence
<220> FEATURE:
<223> OTHER INFORMATION: Description of Artificial Sequence:Primer BR

<400> SEQUENCE: 39
tttctagatt ccccgcgatt ggcgatca                                         28

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence:Primer BF1

<400> SEQUENCE: 40
agcggccgag gatgtgctta ggctgct                                          27

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence:Primer BR1

<400> SEQUENCE: 41
ccgtgccctt gaccgacacc agcgcgt                                          27

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence:Primer C1

<400> SEQUENCE: 42
gcaagctttg tcgctgccgc tcgtcatgct gt                                    32

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence:Primer C6

<400> SEQUENCE: 43
cgctcgagat tcgcgcttcc tgttcctgac                                       30

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence:Primer BF4
```

<400> SEQUENCE: 44
cgtgatgctg cgcctgctcg gccacaacat                              30

<210> SEQ ID NO 45
<211> LENGTH: 32
<212> TYPE: DNA
<213> ORGANISM: Artificial Sequence
<220> FEATURE:
<223> OTHER INFORMATION: Description of Artificial Sequence:Primer BR4

<400> SEQUENCE: 45
gctctagacc tcatcgtccc cctgaacttg tt                           32

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence:Primer F2

<400> SEQUENCE: 46
ggactagtac cggaatgaca ggcggaca                                28

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence:Primer F3

<400> SEQUENCE: 47
gcctgcagca gaacgtgtgg tcgaagcc                                28

<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence:Primer CDA1

<400> SEQUENCE: 48
atctgcagtt gcgcgatgag gaggccacct tgc                          33

<210> SEQ ID NO 49
<211> LENGTH: 33
<212> TYPE: DNA
<213> ORGANISM: Artificial Sequence
<220> FEATURE:
<223> OTHER INFORMATION: Description of Artificial Sequence:Primer CDA6

<400> SEQUENCE: 49
gcaagcttat gacgccgcct gcgccttcga cca                          33

<210> SEQ ID NO 50
<211> LENGTH: 33
<212> TYPE: DNA
<213> ORGANISM: Artificial Sequence
<220> FEATURE:
<223> OTHER INFORMATION: Description of Artificial Sequence:Primer CDA3

<400> SEQUENCE: 50
ctaagcttcg agatcgacgg ggtggaaatc gat                          33

<210> SEQ ID NO 51
<211> LENGTH: 33

-continued

```
<212> TYPE: DNA
<213> ORGANISM: Artificial Sequence
<220> FEATURE:
<223> OTHER INFORMATION: Description of Artificial Sequence:Primer CDA7

<400> SEQUENCE: 51
cgctcgaggg gagaagtcct gggggatgat ccc                                    33

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence:Primer R1

<400> SEQUENCE: 52
ccctgcccgt atggcaagcg                                                   20
```

DNA FRAGMENTS CONTAINING BIOTIN BIOSYNTHETASE GENE AND USE OF THE SAME

This application is the national phase under 35 U.S.C. §371 of prior PCT International Application No. PCT/JP98/00858 which has an International filing date of Mar. 2, 1998 which designated the United States of America, the entire contents of which are hereby incorporated by reference.

TECHNICAL FIELD

The present invention relates to a DNA fragment containing at least one gene concerned in biotin biosynthesis and utilization thereof.

BACKGROUND ART

Biotin is an essential vitamin for human beings, animals, plants and some microorganisms and is useful as a food additive for human beings or animals. As a process for producing biotin by using a microorganism, there have been known a process using a streptomyces or a micromonospore (JP-B-41-21756), a process using a sporobolomyces (JP-B-42-3074), a process using a bacillus, a chromobacterium or a pseudomonas (JP-A-56-160998), a process using a sphingomonas (JP-A-6-133790), etc. There have been also proposed processes for breeding a microorganism in which a gene concerned in biotin biosynthesis and isolated from a microorganism capable of producing biotin is introduced into another microorganism by a genetic engineering technique to promote the expression of the gene concerned in biotin biosynthesis, whereby the activity of an enzyme capable of catalyzing biotin biosynthesis reaction is increased to improve the biotin productivity (JP-A-61-202686, JP-A-2-27980, JP-A-7-231789, etc.).

As genes concerned in biotin biosynthesis in microorganism cells, there are known bio A, bio B, bio F, bio D, bio C and bio H genes derived from *Escherichia coli* (Journal of Biological Chemistry, voL. 263, 19577–19585(1988)). The bio A gene codes for an enzyme having 7,8-diaminopelargonate aminotransferase activity. The bio B gene codes for an enzyme having biotin synthase activity. The bio F gene codes for an enzyme having 7-keto-8-aminopelargonate synthetase activity. The bio D gene codes for an enzyme having desthiobiotin synthetase activity. The bio C gene participates in a biosynthesis stage upstream to pimelyl Co-A in the biotin biosynthetic pathway. The action of the bio H gene is not clear. In the biosynthetic pathway in *Escherichia coli*, intracellular pimelyl Co-A is converted to 7-keto-8-aminopelargonic acid by 7-keto-8-aminopelargonate synthetase, this 7-keto-8-aminopelargonic acid is converted to diaminopelargonic acid by 7,8-diaminopelargonate aminotransferase, this diaminopelargonic acid is converted to desthiobiotin by desthiobiotin synthetase, this desthiobiotin is converted to biotin by biotin synthase, whereby biotin is synthesized. When the bio C gene is deleted, the amount of biotin produced is decreased. Therefore, it is considered that the bio C gene codes for an enzyme having activity to catalyze a reaction in a biosynthesis stage upstream to pimelyl Co-A ("Fermentation and Industry", 46, 102–111(1988)). The base sequences of the bio A, bio B, bio F, bio D, bio C and bio H genes derived from *Escherichia coli* have already been specified. It is known that the bio A, bio B, bio F, bio D and bio C genes form an operon the transcription of which is controlled by an operator.

As genes concerned in biotin biosynthesis and derived from microorganisms belonging to genera other than the genus Escherichia, there have been reported genes derived from *Serratia marcescens* (GenBank database, accession No. D17468) and genes derived from *Bacillus subtilis* (JP-A-7-231789). The base sequence of each of these genes has been specified. It is known that although the base sequences of these genes are different from those of the genes of *Escherichia coli*, the functions of gene products and the biosynthetic pathway of biotin in the case of the former genes are substantially the same as in the case of the latter genes (*Escherichia coli*). On the other hand, genes concerned in biotin biosynthesis and derived from *Bacillus sphaericus* have been reported (Ohsawa et al., Gene 80, 39–48(1989), Gloeckler et al., Gene 87, 63–70(1990)). The genes of *Bacillus sphaericus* are different from those of *Escherichia coli* in the following respects: genes concerned in a biosynthesis stage upstream to pimelyl Co-A, the order and cluster formation of bio genes, etc. (Gloeckler et al., Gene 87, 63–70(1990)).

However, as to genes concerned in biotin biosynthesis and derived from a microorganism belonging to the genus Sphingomonas, their base sequences and either the functions or the structure of gene products have not been known at all. Therefore, there have been no technique for utilizing a gene concerned in biotin biosynthesis and derived from a microorganism belonging to the genus Sphingomonas, for breeding of a biotin-producing microorganism by genetic engineering.

In such circumstances, the present inventors earnestly investigated and consequently found that transformants used for producing biotin or a biotin precursor can be prepared by isolating a DNA fragment containing a gene concerned in biotin biosynthesis from a microorganism belonging to the genus Sphingomonas, inserting the DNA fragment to a vector, and then introducing the vector into host cells. Thus, the present invention has been accomplished.

DISCLOSURE OF THE INVENTION

The present invention provides the following:

1) A DNA fragment containing a gene concerned in biotin biosynthesis and derived from a microorganism belonging to the genus Sphingomonas.

2) A DNA fragment according to the above item 1, wherein said gene is selected from the group consisting of a 7-keto-8-aminopelargonate synthetase gene, a 7,8-diaminopelargonate aminotransferase gene, a desthiobiotin synthetase gene, a biotin synthase gene, and a gene coding for an enzyme having activity to catalyze a reaction in a biosynthesis stage upstream to pimelyl Co-A in the biotin biosynthetic pathway.

3) A DNA fragment according to the above item 1, herein said gene is a gene coding for 7-keto-8-aminopelargonate synthetase.

4) A DNA fragment containing a gene coding for a protein having the amino acid sequence shown as SEQ ID NO: 1 or an amino acid sequence formed by deletion, substitution, modification or addition of one or more amino acids in the amino acid sequence shown as SEQ ID NO: 1, and having 7-keto-8-aminopelargonate synthetase activity.

5) A DNA fragment containing a gene coding for a protein having the amino acid sequence shown as SEQ ID NO: 2 or an amino acid sequence formed by deletion, substitution, modification or addition of one or more amino acids in the amino acid sequence shown as SEQ ID NO: 2, and having 7-keto-8-aminopelargonate synthetase activity.

6) A DNA fragment containing a gene having the base sequence shown as SEQ ID NO: 3, 5or 7.

7) A DNA fragment according to the above item 1, wherein said gene is a gene coding for 7,8-diaminopelargonate aminotransferase.

8) A DNA fragment containing a gene coding for a protein having the amino acid sequence shown as SEQ ID NO: 9 or an amino acid sequence formed by deletion, substitution, modification or addition of one or more amino acids in the amino acid sequence shown as SEQ ID NO: 9, and having 7,8-diaminopelargonate aminotransferase activity.

9) A DNA fragment containing a gene coding for a protein having the amino acid sequence shown as SEQ ID NO: 10 or an amino acid sequence formed by deletion, substitution, modification or addition of one or more amino acids in the amino acid sequence shown as SEQ ID NO: 10, and having 7,8-diaminopelargonate aminotransferase activity.

10) A DNA fragment containing a gene having the base sequence shown as SEQ ID NO: 11 or 13.

11) A DNA fragment according to the above item 1, wherein said gene is a gene coding for desthiobiotin synthetase.

12) A DNA fragment containing a gene coding for a protein having the amino acid sequence shown as SEQ ID NO: 15 or an amino acid sequence formed by deletion, substitution, modification or addition of one or more amino acids in the amino acid sequence shown as SEQ ID NO: 15, and having desthiobiotin synthetase activity.

13) A DNA fragment containing a gene coding for a protein having the amino acid sequence shown as SEQ ID NO: 16 or an amino acid sequence formed by deletion, substitution, modification or addition of one or more amino acids in the amino acid sequence shown as SEQ ID NO: 16, and having desthiobiotin synthetase activity.

14) A DNA fragment containing a gene having the base sequence shown as SEQ ID NO: 17 or 19.

15) A DNA fragment according to the above item 1, wherein said gene is a gene coding for biotin synthase.

16) A DNA fragment containing a gene coding for a protein having the amino acid sequence shown as SEQ ID NO: 21 or an amino acid sequence formed by deletion, substitution, modification or addition of one or more amino acids in the amino acid sequence shown as SEQ ID NO: 21, and having biotin synthase activity.

17) A DNA fragment containing a gene coding for a protein having the amino acid sequence shown as SEQ ID NO: 22 or an amino acid sequence formed by deletion, substitution, modification or addition of one or more amino acids in the amino acid sequence shown as SEQ ID NO: 22, and having biotin synthase activity.

18) A DNA fragment containing a gene coding for a protein having the amino acid sequence shown as SEQ ID NO: 27, and having biotin synthase activity.

19) A DNA fragment containing a gene having the base sequence shown as SEQ ID NO: 23, 25or 28.

20) A DNA fragment according to the above item 1, wherein said gene is a gene coding for an enzyme having activity to catalyze a reaction in a biosynthesis stage upstream to pimelyl Co-A in the biotin biosynthetic pathway.

21) A DNA fragment containing a gene coding for a protein having the amino acid sequence shown as SEQ ID NO: 30 or an amino acid sequence formed by deletion, substitution, modification or addition of one or more amino acids in the amino acid sequence shown as SEQ ID NO: 30, and having activity to catalyze a reaction in a biosynthesis stage upstream to pimelyl Co-A in the biotin biosynthetic pathway.

22) A DNA fragment containing a gene coding for a protein having the amino acid sequence shown as SEQ ID NO: 31 or an amino acid sequence formed by deletion, substitution, modification or addition of one or more amino acids in the amino acid sequence shown as SEQ ID NO: 31, and having activity to catalyze a reaction in a biosynthesis stage upstream to pimelyl Co-A in the biotin biosynthetic pathway.

23) A DNA fragment containing a gene having the base sequence shown as SEQ ID NO: 32 or 34.

24) A DNA fragment having a partial base sequence of a gene concerned in biotin biosynthesis and derived from a microorganism belonging to the genus Sphingomonas.

25) A DNA fragment according to the above item 24, wherein said gene is a 7-keto-8-aminopelargonate synthetase gene, a 7,8-diaminopelargonate aminotransferase gene, a desthiobiotin synthetase gene, a biotin synthase gene, or a gene coding for an enzyme having activity to catalyze a reaction in a biosynthesis stage upstream to pimelyl Co-A in the biotin biosynthetic pathway.

26) A DNA fragment comprising a region coding for a protein of a gene concerned in biotin biosynthesis and derived from a microorganism belonging to the genus Sphingomonas.

27) A DNA fragment according to the above item 26, wherein said gene is a 7-keto-8-aminopelargonate synthetase gene, a 7,8-diaminopelargonate aminotransferase gene, a desthiobiotin synthetase gene, a biotin synthase gene, or a gene coding for an enzyme having activity to catalyze a reaction in a biosynthesis stage upstream to pimelyl Co-A in the biotin biosynthetic pathway.

28) A DNA fragment comprising a gene expression regulatory region of a gene concerned in biotin biosynthesis and derived from a microorganism belonging to the genus Sphingomonas, said region being upstream to a region coding for a protein.

29) A DNA fragment according to the above item 28, wherein said gene is a 7-keto-8-aminopelargonate synthetase gene, a 7,8-diaminopelargonate aminotransferase gene, a desthiobiotin synthetase gene, a biotin synthase gene, or a gene coding for an enzyme having activity to catalyze a reaction in a biosynthesis stage upstream to pimelyl Co-A in the biotin biosynthetic pathway.

30) A DNA fragment having the base sequence shown as SEQ ID NO: 36 or 37.

31) A DNA fragment according to any one of the above items 1, 2, 3, 7, 11, 15, 20, 24, 25, 26, 27, 28 and 29, wherein the microorganism belonging to the genus Sphingomonas is *Sphingomonas paucimobilis* JCM7511 or Sphingomonas sp. SC42405.

32) A vector containing a DNA fragment according to any one of the above items 1 to 31.

33) A method for preparing a vector which comprises inserting a DNA fragment according to any one of the above items 1 to 31 to a vector replicable in host cells.

34) A vector according to the above item 32, wherein a gene expression regulatory region is linked upstream to a region coding for a protein.

35) A transformant having at least one DNA fragment according to any one of the above items 1 to 31 or at least one vector according to the above item 32 or 34 introduced into a host cell.

36) A transformant according to the above item 35, wherein the host cell is a microorganism.

37) A method for preparing transformants which comprises introducing a vector according to the above item 32 or 34 into a host cell.

BEST MODE FOR CARRYING OUT THE INVENTION

Figure 1:
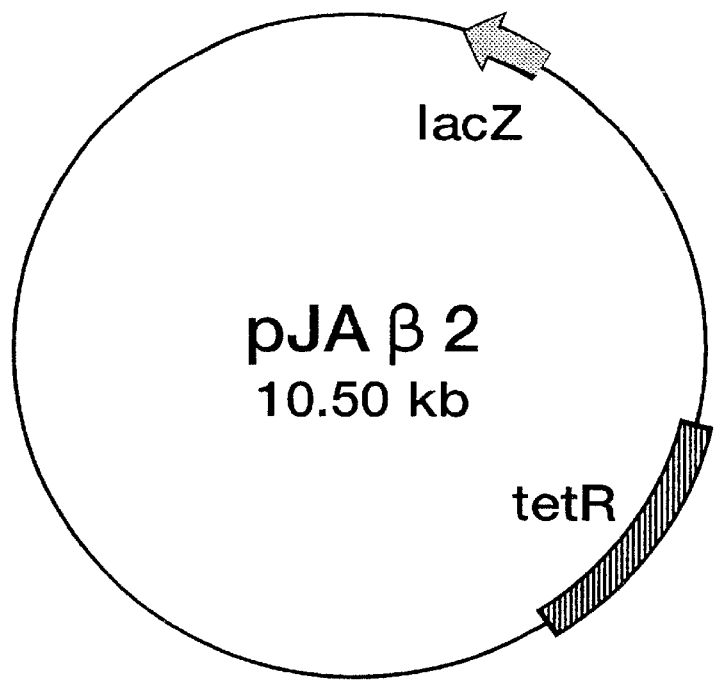
FIG. 1 shows the structure and restriction map of plasmid pJAβ2.

In the present description, the gene concerned in biotin biosynthesis and derived from a microorganism belonging to the genus Sphingomonas refers to a gene coding for an enzyme concerned in biotin biosynthesis in cells of the microorganism belonging to the genus Sphingomonas. Said gene includes, for example, a 7-keto-8-aminopelargonate synthetase gene (hereinafter referred to as "the present invention bio F gene"), a 7,8-diaminopelargonate aminotransferase gene (hereinafter referred to as "the present invention bio A gene"), a desthiobiotin synthetase gene (hereinafter referred to as "the present invention bio D gene"), a biotin synthase gene (hereinafter referred to as "the present invention bio B gene"), and a gene coding for an enzyme having activity to catalyze a reaction in a biosynthesis stage upstream to pimelyl Co-A in the biotin biosynthetic pathway (hereinafter referred to as "the present invention bio C gene").

The present invention bio F gene includes, for example, genes containing a region of approximately 1.1–1.2 kbp coding for 7-keto-8-aminopelargonate synthetase which are derived from microorganisms belonging to the genus Sphingomonas. More specific examples thereof are genes coding for a protein having the amino acid sequence shown as SEQ ID NO: 1 or 2 or an amino acid sequence formed by deletion, substitution, modification or addition of one or more amino acids in the amino acid sequence shown as SEQ ID NO: 1 or 2, and having 7-keto-8-aminopelargonate synthetase activity; and 7-keto-8-aminopelargonate synthetase genes having the base sequence shown as SEQ ID NO: 3, 5 or 7.

The present invention bio A gene includes, for example, genes containing a region of approximately 1.2–1.3 kbp coding for 7,8-diaminopelargonate aminotransferase which are derived from microorganisms belonging to the genus Sphingomonas. More specific examples thereof are genes coding for a protein having the amino acid sequence shown as SEQ ID NO: 9 or 10 or an amino acid sequence formed by deletion, substitution, modification or addition of one or more amino acids in the amino acid sequence shown as SEQ ID NO: 9 or 10, and having 7,8-diaminopelargonate aminotransferase activity; and 7,8-diaminopelargonate aminotransferase genes having the base sequence shown as SEQ ID NO: 11 or 13.

The present invention bio D gene includes, for example, genes containing a region of about 0.6 kbp coding for desthiobiotin synthetase which are derived from microorganisms belonging to the genus Sphingomonas. More specific examples thereof are genes coding for a protein having the amino acid sequence shown as SEQ ID NO: 15 or 16 or an amino acid sequence formed by deletion, substitution, modification or addition of one or more amino acids in the amino acid sequence shown as SEQ ID NO: 15 or 16, and having desthiobiotin synthetase activity; and desthiobiotin synthetase genes having the base sequence shown as SEQ ID NO: 17 or 19.

The present invention bio B gene includes, for example, genes containing a region of approximately 1.0–1.1 kbp coding for biotin synthase which are derived from microorganisms belonging to the genus Sphingomonas. More specific examples thereof are genes coding for a protein having the amino acid sequence shown as SEQ ID NO: 21, 22 or 27 or an amino acid sequence formed by deletion, substitution, modification or addition of one or more amino acids in the amino acid sequence shown as SEQ ID NO: 21, 22 or 27, and having biotin synthase activity; and biotin synthase genes having the base sequence shown as SEQ ID NO: 23, 25 or 28.

The present invention bio C gene includes, for example, genes containing a region of approximately 0.8–0.9 kbp coding for an enzyme having activity to catalyze a reaction in a biosynthesis stage upstream to pimelyl Co-A in the biotin biosynthetic pathway which are derived from microorganisms belonging to the genus Sphingomonas. More specific examples thereof are genes coding for a protein having the amino acid sequence shown as SEQ ID NO: 30 or 31 or an amino acid sequence formed by deletion, substitution, modification or addition of one or more amino acids in the amino acid sequence shown as SEQ ID NO: 30 or 31, and having activity to catalyze a reaction in a biosynthesis stage upstream to pimelyl Co-A in the biotin biosynthetic pathway; and genes coding for an enzyme having activity to catalyze a reaction in a biosynthesis stage upstream to pimelyl Co-A in the biotin biosynthetic pathway which have the base sequence shown as SEQ ID NO: 32 or 34.

A microorganism used for isolating any of the present invention bio F, bio A, bio D, bio B and bio C genes therefrom may be either a strain separated from the nature or a strain obtained by introducing a mutation into said separated strain, so long as it is a biotin-producing bacterium belonging to the genus Sphingomonas, namely, it has a gene concerned in biotin biosynthesis. Said microorganism includes, for example, the *Sphingomonas paucimobilis* JCM7511 strain and Sphingomonas sp. SC42405 strain described in JP-A-133790. The *Sphingomonas paucimobilis* JCM7511 strain is stored in a distributable state in the biological line storing facilities of the Institute of Physical and Chemical Research. The Sphingomonas sp. SC42405 strain is deposited under the Budapest Treaty as FERM-BP3995 (accession number) (date of deposition: Sep. 3, 1992) in National Institute of Bioscience and Human-Technology, Agency of Industrial Science and Technology, Ministry of International Trade and Industry (1–3, Higashi-1-chome, Tsukuba-shi, Ibaraki, Japan) and has been disclosed in U.S. Pat. No. 5,432,067.

There is given below an example of method for preparing a DNA fragment containing a gene concerned in biotin biosynthesis from a biotin-producing bacterium belonging to the genus Sphingomonas.

First, the genomic DNA of a microorganism belonging to the genus Sphingomonas is isolated, for example, by the conventional extraction method of genomic DNA described in Biochemica. Biophysica. Acta., vol. 72, 619–629 (1963), etc. The isolated genomic DNA is partially cleaved with a suitable restriction enzyme such as Sau 3AI, and the DNA fragments thus obtained are inserted to a suitable vector to prepare a genomic DNA library. As the vector used in this case, any vector may be used so long as it can be proliferated and replicated in a strain into which the genomic DNA library is introduced. The vector includes, for example, plasmids, bacteriophages and cosmids.

As a method for identifying and isolating a gene concerned in biotin biosynthesis from the genomic DNA library thus prepared, there can be mentioned a method of introducing the genomic DNA library into a gene deletion mutant which lacks a gene concerned in biotin biosynthesis and has biotin requirement, and selecting a strain possessing regained biotin productivity from the transformants obtained. As the biotin-requiring mutant used in this method, any strain may be used so long as the genomic DNA fragments of the microorganism of the genus Sphingomonas introduced thereinto can be expressed in cells of the strain. Such a mutant can be prepared, for example, by the conventional method described in Proceeding of the National Academy of Sciences U.S.A., vol. 69, 2219 (1972), Journal of Bacteriology, vol. 115, 662 (1973), etc. As a method for introducing the genomic DNA library into the biotin-requiring mutant, there can be mentioned conventional methods such as a method of treating cells with calcium chloride (Molecular Cloning, 2nd ed., Cold Spring Harbor Laboratory Press(1989)), electroporation method (Current Protocols in Molecular Biology, vol. 1, John Wiley & Sons. Inc. ISBNO-471-50338-X(1987)), etc.

The obtained transformants of the biotin-requiring mutant are cultured in a suitable selective medium containing no biotin, and the grown transformants are selected. The thus selected transformants are candidates of strains retaining the vector having as an insert the DNA fragment containing a gene concerned in biotin biosynthesis and derived from the microorganism belonging to the genus Sphingomonas.

For example, when the vector is a plasmid or a cosmid, the recombinant vector is extracted from the above-mentioned transformants by a conventional method such as alkali lysis method or boiling method (Molecular Cloning, 2nd ed., Cold Spring Harbor Laboratory Press(1989)). When the vector is a bacteriophage, the recombinant vector is extracted from the transformants by a conventional method such as a method using density-gradient centrifugation or ion exchange chromatography (Current Protocols in Molecular Biology, vol. 1, John Wiley & Sons. Inc. ISBNO-471–50338-(1987)). The base sequence of the recombinant vector extracted is analyzed by Sanger dideoxy-mediated chain-termination method (Molecular Cloning, 2nd ed., Cold Spring Harbor Laboratory Press(1989)). Thus, the base sequence of the DNA fragment inserted to the vector can be determined.

When a region coding for a protein and having a highly homologous base sequence with each known gene described below is selected from open reading frames of 500 bp or more found in the determined base sequence, it can be specified as a gene concerned in biotin biosynthesis of the bacterium of the genus Sphingomonas: when the DNA fragment is that obtained by using a bio F deletion mutant, the gene is a known bio F gene; when the DNA fragment is that obtained by using a bio A deletion mutant, the gene is a known bio A gene; when the DNA fragment is that obtained by using a bio D deletion mutant, the gene is a known bio D gene; when the DNA fragment is that obtained by using a bio B deletion mutant, the gene is a known bio B gene; and when the DNA fragment is that obtained by using a bio C deletion mutant, the gene is a known bio C gene. The following is also possible. Each coding region is excised with suitable restriction enzymes and subclones including each coding region are prepared. Each subclone is introduced into a gene deletion mutant as follows: when the subclone is that of the DNA fragment obtained by using a bio F deletion mutant, it is introduced into a bio F deletion mutant; when the subclone is that of the DNA fragment obtained by using a bio A deletion mutant, it is introduced into a bio A deletion mutant; when the subclone is that of the DNA fragment obtained by using a bio D deletion mutant, it is introduced into a bio D deletion mutant; when the subclone is that of the DNA fragment obtained by using a bio B deletion mutant, it is introduced into a bio B deletion mutant; and when the subclone is that of the DNA fragment obtained by using a bio C deletion mutant, it is introduced into a bio C deletion mutant. The growth of the mutant having the gene thus introduced thereinto on a suitable selective medium containing no biotin is investigated, whereby the coding region included in the subclone retained by the mutant which has becomes growable is specified as a gene concerned in biotin biosynthesis of the bacterium of the genus Sphingomonas.

Furthermore, the desired gene thus obtained can be improved in function, for example, by the conventional mutation introduction method described in Molecular Cloning, 2nd ed., Cold Spring Harbor Laboratory Press (1989), etc. A mutation can be introduced into any gene which participates in biotin biosynthesis. In improving the biotin productivity, it is particularly effective to introduce a mutation into a bio B gene coding for biotin synthase capable of catalyzing the conversion of desthiobiotin to biotin which is often a rate-determining step in the biotin biosynthetic pathway. The mutation to be introduced may be a mutation in a region coding for a protein which enhances enzyme activity or improves protein stability, or a mutation in a gene expression regulatory region which promotes the gene expression. The gene having a mutation introduced thereinto is expressed by its introduction into a gene deletion mutant having biotin requirement, as described above, and its ability to complement gene deletion is compared with that of the wild-type gene. Thus, it is possible to select a mutant gene which can contribute to the improvement of the biotin productivity. The mutant gene which can contribute to the improvement of the biotin productivity can be selected also by expressing the gene having a mutation introduced there into, in a microorganism, and comparing the amount produced of an enzyme coded for by the gene introduced, the enzyme activity, the amount of a compound produced by a reaction catalyzed by said enzyme, or the like, with that in the case of using the wild-type gene. The activity of an enzyme having activity to catalyze a reaction in a biosynthesis stage upstream to pimelyl Co-A in the biotin biosynthetic pathway, 7-keto-8-aminopelargonate synthetase, 7,8-diaminopelargonate aminotransferase and desthiobiotin synthetase can be measured, for example, by the method described in Y. Izumi et al., Methods in Enzymolozy, vol. 62, 326–338 (1979), etc. The activity of biotin synthase can be measured, for example, by the method described in I. Sanyal et al., Archives of Biochemistry and Biophysics., vol. 326, 48–56 (1996), A. Mejean et al., Biochemical and Biophysical Research Communications, vol. 217, 1231–1237 (1995), etc.

A specific example of the above-mentioned gene having a mutation introduced thereinto is a biotin synthase gene having the base sequence shown as SEQ ID NO: 28. In this gene, when A of the initiation codon (ATG) is taken as the +1st base, the −57th base and the 706th base are substituents, as compared with a biotin synthase gene having the base sequence shown as SEQ ID NO: 23. As the gene having a mutation introduced thereinto, there can also be exemplified a 7-keto-8-aminopelargonate synthetase gene having the base sequence shown as SEQ ID NO: 7. In this gene, when A of the initiation codon (ATG) is taken as the +1st base, the −11th base is a substituent, as compared with a 7-keto-8-aminopelargonate synthetase gene having the base sequence shown as SEQ ID NO: 5.

In the present description, the term "DNA fragment containing at least one gene concerned in biotin biosynthesis and derived from a microorganism belonging to the genus Sphingomonas" means a DNA fragment containing at least one gene coding for an enzyme concerned in biotin biosynthesis in cells of a microorganism belonging to the genus Sphingomonas. Said DNA fragment may be either a DNA fragment isolated from a microorganism in the manner described above, or a DNA fragment prepared by ligating genes coding for an enzyme participating in biotin biosynthesis which are derived from any of various microorganism strains, or genes obtained by introducing a mutation into the aforesaid gene.

The present invention also provides a DNA fragment having a partial base sequence of a gene concerned in biotin biosynthesis and derived from a microorganism belonging to the genus Sphingomonas. Said DNA fragment is useful as, for example, a probe used in a hyblidization method or a primer used in a PCR method. When the DNA fragment is used as a primer used in a PCR method, the number of its bases is preferably large in general for assuring the specificity of annealing. On the other hand, with an increase of the number of the bases, the primer itself easily has a higher-order structure during PCR reactions, so that the efficiency of annealing is lowered in some cases. Therefore, troublesome operations are required for purification after synthesis. When such a disadvantage is considered, the number of the bases is preferably not too large. Usually, a gene fragment composed of a single-stranded DNA having not more than 50 and not less than 15 bases is preferable. Specific examples of such DNA fragment are DNA fragments having any of the base sequences of primers BF, BR, BF1, BR1, C1 and C6 (SEQ ID NOS:38–43, respectively) shown in Table 1, and DNA fragments having any of the base sequences of primers BF4, BR4, F2, F3, CDA1, CDA6, CDA3 and CDA7 (SEQ ID NOS:44–51, respectively) shown in Table 2.

TABLE 1

PCR primers

| Primer | Base sequence |
|---|---|
| BF | 5'-ATTCTAGAACAGGACTATCAGGCACTCT-3' |
| BR | 5'-TTTCTAGATTCCCCGCGATTGGCGATCA-3' |
| BF1 | 5'-AGCGGCCGAGGATGTGCTTAGGCTGCT-3' |
| BR1 | 5'-CCGTGCCCTTGACCGACACCAGCGCGT-3' |
| C1 | 5'-GCAAGCTTTGTCGCTGCCGCTCGTCATGCTGT-3' |
| C6 | 5'-CGCTCGAGATTCGCGCTTCCTGTTCCTGAC-3' |

TABLE 2

PCR primers

| Primer | Base sequence |
|---|---|
| BF4 | 5'-CGTGATGCTGCGCCTGCTCGGCCACAACAT-3' |
| BR4 | 5'-GCTCTAGACCTCATCGTCCCCCTGAACTTGTT-3' |
| F2 | 5'-GGACTAGTACCGGAATGACAGGCGGACA-3' |
| F3 | 5'-GCCTGCAGCAGAACGTGTGGTCGAAGCC-3' |
| CDA1 | 5'-ATCTGCAGTTGCGCGATGAGGAGGCCACCTTGC-3' |
| CDA6 | 5'-GCAAGCTTATGACGCCGCCTGCGCCTTCGACCA-3' |
| CDA3 | 5'-CTAAGCTTCGAGATCGACGGGGTGGAAATCGAT-3' |
| CDA7 | 5'-CGCTCGAGGGGAGAAGTCCTGGGGGATGATCCC-3' |

The gene concerned in biotin biosynthesis and derived from a microorganism belonging to the genus Sphingomonas contains a region coding for a protein and a gene expression regulatory region upstream or downstream thereto.

A DNA fragment composed of the region coding for a protein of the gene concerned in biotin biosynthesis and derived from a microorganism belonging to the genus Sphingomonas can be used, for example, in a step of linking the aforesaid region to a promoter capable of functioning in host cells, in the construction of a vector for expressing the gene in the host cells.

The gene expression regulatory region refers to a region of tens to hundreds base pairs which is located upstream or downstream to a region coding for a protein and has an important influence on the regulation of the gene expression for the protein. In particular, a promoter located upstream to the region coding for a protein is an important gene expression regulatory region. Specific examples of the gene expression regulatory region are a region having a base sequence from the −222th base to the −1st base in the case of taking A of the initiation codon (ATG) as the +1st base in the SEQ ID NO: 23, and a region having a base sequence from the −201th base to the −1st base in the case of taking A of the initiation codon (ATG) as the +1st base in the SEQ ID NO: 5.

The gene expression regulatory region is specified, for example, by introducing a mutation such as point mutation, deletion or insertion into base sequences before and after the region coding for a protein of the gene concerned in biotin biosynthesis and derived from a microorganism belonging to the genus Sphingomonas, expressing said gene in a microorganism, measuring the amount produced of the enzyme coded for by the gene, the enzyme activity, the amount of a compound produced by a reaction catalyzed by the enzyme, or the like, and finding a region in which the introduction of the mutation remarkably changes the measured value. It is also possible to carry out the same experiment as above except for using a gene coding for a protein which permits easy measurement of the above amount or enzyme activity, in place of the region coding for a protein of the above-mentioned gene. The gene expression regulatory region can be obtained by specifying it by the above method.

The gene expression regulatory region obtained can be modified into a gene expression regulatory region which permits a higher degree of the gene expression, by introducing a mutation such as substitution, deletion or insertion, for example, by a PCR method as described above. It is also possible to obtain a gene expression regulatory region which permits a high degree of the gene expression, by isolating a gene from a mutant capable of producing an increased amount of a desired protein or an increased enzyme activity owing to mutation or the like. As such a gene expression regulatory region, there can be mentioned gene expression regulatory regions having base sequences shown as SEQ ID NOS:36 and 37 respectively.

A DNA fragment composed of the above-mentioned gene expression regulatory region of the gene concerned in biotin biosynthesis and derived from a microorganism belonging to the genus Sphingomonas can be used, for example, for constructing a vector for expressing the gene in a microorganism belonging to the genus sphingomonas.

The thus obtained DNA fragment containing the gene concerned in biotin biosynthesis and derived from a microorganism belonging to the genus Sphingomonas or a partial base sequence of said gene is inserted to a vector replicable in host cells, whereby there can be constructed a vector for introducing said gene or a portion thereof into the host cells. Furthermore, the gene expression regulatory region is linked upstream to the region coding for a protein of the aforesaid gene, followed by insertion to a vector, whereby a vector for expressing said gene in host cells can be constructed.

As the DNA fragment used in this case, there can be mentioned DNA fragments obtained by previously cleaving a DNA fragment containing a gene concerned in biotin biosynthesis and derived from a microorganism belonging to the genus Sphingomonas which is obtained in the manner described above, to a suitable size with suitable restriction enzymes to facilitate the ligation of the DNA fragment with a vector; and DNA fragments obtained by introducing an arbitrary restriction site into each end of the gene concerned in biotin biosynthesis, by PCR, in the case where no suitable restriction site is present.

As the gene to be inserted to a vector, it is sufficient that there is used at least one gene selected from the group consisting of the above-mentioned present invention bio F, bio A, bio D, bio B and bio C genes. For example, either all or some of the above genes may be inserted to a vector. In addition, a plurality of specific genes may be inserted for increasing a specific enzyme activity. If necessary, selective marker genes such as drug-resistant genes useful for the selection of transformants described hereinafter, and genomic DNA's utilizable for homologous recombination with the genomes of host cells may be inserted to one and the same vector together with the above-mentioned gene(s).

As the gene expression regulatory region to be linked upstream to the region coding for a protein, any base sequence may be used so long as it has a function of regulating the gene expression in host cells. For example, when the host cells are cells of a microorganism belonging to the genus Sphingomonas, there can be mentioned the gene expression regulatory region of a gene concerned in biotin biosynthesis and derived from a microorganism belonging to the genus Sphingomonas, such as is described above. When the host cells are *E. coli* cells, there can be utilized commercially available promoters having gene expression regulatory activity in *E. coli*.

As the vector to which the DNA fragment is inserted, any vector may be used so long as it is replicable in host cells, for instance, microorganism cells. For example, when the host cells are cells of a microorganism belonging to the genus Sphingomonas, there can be used RK2 classified in group P of incompatible plasmids, and plasmid vectors derived from RK2 (Plasmids, vol. 13, 149–153 (1985), Journal of Bacteriology, vol. 167, 604–610 (1986)), RSF1010 classified in group Q of incompatible plasmids, and plasmid vectors derived from RSF1010 (Gene, vol. 16, 237–247 (1981)), etc. When the host cells are *E. coli* cells, there can be utilized commercially available plasmids, phages and the like, which are replicable in *E. coli*.

Transformants can be prepared by introducing the thus constructed vector containing the gene concerned in biotin biosynthesis into host cells, for example, host microorganism cells.

The host cells into which the DNA fragment containing the gene concerned in biotin biosynthesis is introduced are not particularly limited so long as the DNA fragment introduced is stably held by them and the gene is expressed in them. As the host cells, there can be mentioned cells of microorganisms belonging to the genus Sphingomonas, *E. coli*, etc.

As a method for introducing the vector into host cells, a conventional genetic engineering method can be employed. For example, as a method for introducing the vector into a host microorganism, there can be mentioned conventional methods such as a method of treating cells with calcium chloride (Molecular Cloning, 2nd ed., Cold Spring Harbor Laboratory Press(1989)), electroporation method (Current Protocols in Molecular Biology, vol. 1, John Wiley & Sons. Inc. ISBNO-471-50338-X(1987)), etc. There can also be employed a gene introduction method in which a desired DNA fragment is introduced into the genomes of host cells by utilizing homologous recombination. For example, a genomic DNA fragment derived from host cells is linked to each end of the DNA fragment containing the gene concerned in biotin biosynthesis and the linked fragments are inserted to a vector, after which the vector is introduced into host cells. When homologous recombination between the genomic DNA on the vector and the genomic DNA of the host cells takes place, the DNA fragment containing the gene concerned in biotin biosynthesis is introduced into genomes of the host cells to give transformants.

The transformed microorganism obtained by introducing the DNA fragment containing the gene concerned in biotin biosynthesis, in the manner described above, can be efficiently selected on the basis of the phenotype of a selective marker gene contained in the vector and introduced into the host cells together with the gene. For example, when the selective marker gene is an ampicillin-resistant gene, the cells are streaked on a suitable nutrient medium containing ampicillin, after the gene introduction, and the colonies developed are separated by a hooking up method, whereby transformants can be obtained. Thus, there can be obtained the transformants having as an introduced DNA fragment the DNA fragment containing the gene concerned in biotin biosynthesis. The transformants can be utilized for producing biotin, and 7-keto-8-aminopelargonic acid, 7,8-diaminopelargonic acid and desthiobiotin which are precursors for biotin biosynthesis.

The present invention is explained below in further detail with reference to examples but is not limited by the examples.

EXAMPLE 1

Isolation of a Gene Concerned in Biotin Biosynthesis (1-A) Preparation of Genomic DNA of *Sphingomonas paucimobilis* JCM7511

A loopful of *Sphingomonas paucimobilis* JCM7511 was inoculated into 200 ml of LB culture medium (1% tryptone, 0.5% yeast extract, 1% NaCl) and subjected to shaking culture at 30° C. for 15 hours, and bacterial cells were harvested at the logarithmic growth phase by centrifugation (8,000 rpm, 10 min.). The harvested cells were suspended in 20 ml of A buffer (25% sucrose, 50 mM Tris-HCl (pH 8.0)) and 2.5 ml of a lysozyme chloride solution (50 mg/ml) was added, followed by incubation at 37° C. for 30 minutes. Then, 2.5 ml of an SDS solution (10% (v/v)) and 0.25 ml of an EDTA solution (0.5 M) were added thereto, and the resulting mixture was incubated at 37° C. for 16 hours. To the incubated mixture was added an equal amount of TE saturated phenol and the resulting mixture was slowly stirred and then centrifuged (10,000 rpm, 10 min.), after which the upper layer was recovered to carry out deproteinization. The above deproteinization procedure was repeated 5 times more. Ethanol twice volume as much as the recovered upper layer was added to the recovered upper layer to precipitate DNA. The DNA was recovered by winding it round a glass rod, washed with 70% ethanol, air-dried and then dissolved in 20 ml of TE buffer, and 20 µl of RNase (10 mg/ml) was added, followed by incubation at 37° C. for 16 hours. Thus, a DNA solution containing about 21 mg of genomic DNA of Sphingomonas paucimobilis JCM7511 was obtained.

(1-B) Preparation of a Genomic DNA Library

Forty-three micrograms of the genomic DNA obtained in (1-A) was treated with 15 U of a restriction enzyme Sau 3 AI at 37° C. for 2 minutes to be partially digested. The genomic DNA fragments obtained by the partial digestion were mixed with a plasmid vector pUC19 (available from TAKARA SHUZO Co., Ltd.) cleaved by a restriction enzyme Bam HI and then dephosphorylated. Using a ligation kit (available from TAKARA SHUZO Co., Ltd.), the genomic DNA fragments obtained by the partial digestion were ligated with the plasmid vector pUC19 according to the attached operating manual to prepare recombinant plasmids containing various DNA fragments.

(1-C) Selection of Recombinant Plasmids Containing a DNA Fragment Concerned in Biotin Biosynthesis The recombinant plasmids obtained in (1-B) were introduced into strains of bio F deletion mutant *E. coli* (R874), bio A deletion mutant *E. coli* (R879), bio B deletion mutant *E. coli* (R875) and bio C deletion mutant *E. coli* (R876), respectively (Journal of Bacteriology, vol. 94, 2065–2066 (1972), Journal of Bacteriology, vol. 112, 830–839 (1972)) with a gene pulser (mfd. by Bio-Rad Laboratories Inc.) by an electroporation method (applied voltage 18 kV/cm, capacitance 25 µF, resistance 400Ω). The strains thus treated was streaked on biotin-free selective agar plate (1.48% $Na_2HPO_4\text{-}7H_2O$, 0.3% $KH_2PO_4$, 0.05 NaCl, 0.1% $NH_4Cl$, 0.005% ampicillin, 1.5% agar) and the agar plate was incubated at 37° C. for 2 days. Strains growing on the medium and forming colonies were picked up and then incubated on LB medium at 37° C. for 16 hours. Plasmids were extracted from these strains by the alkali lysis method (Molecular Cloning, 2nd ed., Cold Spring Harbor Laboratory Press(1989)), cleaved with restriction enzymes and investigated by agarose gel electrophoresis to find that the recombinant plasmid introduced into each deletion mutant contained an inserted fragment having a size shown in Table 3.

TABLE 3

Recombinant plasmids complementing defective strains for growth

| Defective strain | Plasmid obtained | Size of inserted fragment (kbp) |
|---|---|---|
| R874 | pBC01 | 1.8 |
| R879 | pBC02 | 2.8 |
| R875 | pBC03 | 1.4 |

TABLE 3-continued

Recombinant plasmids complementing defective strains for growth

| Defective strain | Plasmid obtained | Size of inserted fragment (kbp) |
|---|---|---|
| R876 | pBC04 | 1.4 |
|  | pBC05 | 3.7 |

(1-D) Analysis of the Base Sequence of a DNA Fragment Containing a Gene Concerned in Biotin Biosynthesis For the recombinant plasmids pBC01, pBC02, pBC03 pBC04 and pBC05 obtained in (1-C), deletion clones containing inserted fragments of various sizes were prepared by the use of a deletion kit for kilo sequence (available from TAKARA SHUZO Co., Ltd.) in the manner described below.

Twenty micrograms of each of the recombinant plasmids pBC01, pBC02, pBC03, pBC04 and pBC05 was cleaved with the following enzymes; pBC01: Sma I and Kpn I, pBC02: Pst I and Xba I, pBC03, pBC04 and pBC05: Xba I and Sse 8387 I. The enzymes were removed by extraction with phenol, followed by precipitation of DNA with ethanol. The obtained DNA was dissolved in 100 µl of Exo III buffer (50 mM Tris-HCl (pH 8.0), 100 mM NaCl, 5 mM $MgCl_2$, 10 mM 2-mercaptoethanol), followed by adding thereto 180 units of exonuclease III, and the resulting mixture was stirred and then incubated at 37° C. At intervals of 1 minute, 10 µl of the resulting solution was sampled and then mixed with 100 µl of ice-cooled MB nuclease buffer (40 mM Na-acetate (pH 4.5), 100 mM NaCl, 2 mM $ZnCl_2$, 10% glycerol) and the exonuclease III was inactivated by treatment at 65° C. for 5 minutes. The thus obtained solution was cooled to 37° C. and then 50 units of MB nuclease was added, followed by incubation for 60 minutes. The enzymes were removed by extraction with phenol, followed by precipitation of DNA with ethanol. The obtained DNA was dissolved in 50 µl of Klenow buffer (7 mM Tris-HCl (pH 7.5), 0.1 mM EDTA, 20 mM NaCl, 7 mM $MgCl_2$, dNTP's 0.1 mM each) and 2 units of Klenow fragment was added, followed by incubation at 37° C. for 15 minutes. To 100 µof ligation solution A were added 10 µl of the resulting solution and then 12 µl of ligation solution B, followed by incubation at 16° C. for 1 hour. Then, DNA was concentrated by precipitation with ethanol and dissolved in 5 µl of sterilized water, and the resulting solution was introduced into *E. coli* JM109. The thus treated *E. coli* JM109 was streaked on agar plate of ampicillin (0.005%)-containing LB culture medium (1% tryptone, 0.5% yeast extract, 1% NaCl, 1.5% agar) and the agar plate was incubated at 37° C. for 16 hours. Plasmids were extracted from the developed colonies and the sizes of the inserted DNA fragments were investigated. Eight clones containing inserted fragments, respectively, varying in size from 250 bp to 1.8 kbp by about 250 bp each were selected as deletion clones of pBC01. Twelve clones containing inserted fragments, respectively, varying in size from 250 bp to 2.8 kbp by about 250 bp each were selected as deletion clones of pBC02. Six clones containing inserted fragments, respectively, varying in size from 250 bp to 1.4 kbp by about 250 bp each were selected as deletion clones of pBC03. Six clones containing inserted fragments, respectively, varying in size from 250 bp to 1.4 kbp by about 250 bp each were selected as deletion clones of pBC04. Fifteen clones containing inserted fragments, respectively, varying in size from 250 bp to 3.7 kbp by about 250 bp each were selected as deletion clones of pBC05.

Each deletion clone was extracted by the alkali lysis method (Molecular Cloning, 2nd ed., Cold Spring Harbor Laboratory Press(1989)). Using 300 ng of the extract as a template and M13 primer M4 (available from TAKARA SHUZO Co., Ltd.) or M13 primer RV (available from TAKARA SHUZO Co., Ltd.) as a primer, sequence reaction was carried out by the use of an ABI prism dye terminator cycle sequencing ready reaction kit (mfd. by Perkin-Elmer Corporation), and the base sequence was analyzed by means of an automatic base sequence analyzer 373A (mfd. by Perkin-Elmer Corporation).

For specifying a gene concerned in biotin biosynthesis among the base sequences of the inserted fragments of the recombinant plasmids, regions coding for a protein which were highly homologous in base sequence with known bio F gene, bio A gene, bio D gene, bio B gene and bio C gene, respectively, were selected from open reading frames of 500 bp or more present in the fragments and specified as the genes of the bacterium of the genus Sphingomonas which correspond to the above genes, respectively. pBC01 contained bio F (SEQ ID NO: 3). pBC02 contained bio D (SEQ ID NO: 17) and bio A (SEQ ID NO: 13). pBC03 contained bio B (SEQ ID NO: 23). Each of pBC04 and pBC05 contained bio C (SEQ ID NO: 32). The base sequences of the inserted fragments of pBC01 and pBC02 which had been independently obtained were compared to find that a combination of the inserted fragments of pBC01 and pBC02 is continuous DNA on genome. Thus, it became clear that bio F, bio D and bio A form an operon.

EXAMPLE 2

Isolation of a Gene Concerned in Biotin Biosynthesis (2-A) Preparation of Genomic DNA of Sphingomonas sp. SC42405

A loopful of Sphingomonas sp. SC42405 was inoculated into 200 ml of LB culture medium (1% tryptone, 0.5% yeast extract, 1% NaCl) and subjected to shaking culture at 30° C. for 15 hours, and bacterial cells were harvested at the logarithmic growth phase by centrifugation (8,000 rpm, 10 min.). The harvested cells were suspended in 20 ml of A buffer (25% sucrose, 50 mM Tris-HCl (pH 8.0)) and 2.5 ml of a lysozyme chloride solution (50 mg/ml) was added, followed by incubation at 37° C. for 30 minutes. Then, 2.5 ml of an SDS solution (10% (v/v)) and 0.25 ml of an EDTA solution (0.5 M) were added thereto, and the resulting mixture was incubated at 37° C. for 16 hours. To the incubated mixture was added an equal amount of TE saturated phenol and the resulting mixture was slowly stirred and then centrifuged (10,000 rpm, 10 min.), after which the upper layer was recovered to carry out deproteinization. The above deproteinization procedure was repeated 5 times more. Ethanol twice volume as much as the recovered upper layer was added to the recovered upper layer to precipitate DNA. The DNA was recovered by winding it round a glass rod, washed with 70% ethanol, air-dried and then dissolved in 20 ml of TE buffer, and 20 µl of RNase (10 mg/ml) was added, followed by incubation at 37° C. for 16 hours. Thus, a DNA solution containing about 21 mg of genomic DNA of Sphingomonas sp. SC42405 was obtained.

(2-B) Preparation of a Genomic DNA Library

Fifty micrograms of the genomic DNA obtained in (2-A) was treated with 15 U of a restriction enzyme Sau 3 AI at 37° C. for 2.5 minutes to be partially digested. The genomic DNA fragments obtained by the partial digestion were mixed with a plasmid vector pUC19 (available from TAKARA SHUZO Co., Ltd.) cleaved by a restriction enzyme BamHI and then dephosphorylated. Using a ligation kit (available from TAKARA SHUZO Co., Ltd.), the genomic DNA fragments obtained by the partial digestion were ligated with the plasmid vector pUC19 according to the attached operating manual to prepare recombinant plasmids containing various DNA fragments.

(2-C) Selection of Recombinant Plasmids Containing a DNA Fragment Concerned in Biotin Biosynthesis The recombinant plasmids obtained in (2-B) were introduced into strains of bio F deletion mutant E. coli (R874), bio A deletion mutant E. coli (R879), bio B deletion mutant E. coli (R875) and bio C deletion mutant E. coli (R876), respectively (Journal of Bacteriology, vol. 94, 2065–2066 (1972), Journal of Bacteriology, vol. 112, 830–839 (1972)) with a gene pulser (mfd. by Bio-Rad Laboratories Inc.) by an electroporation method (applied voltage 18 kV/cm, capacitance 25 µF, resistance 400Ω). The strains thus treated were streaked on biotin-free selective agar plate (1.71% $Na_2HPO_4$-$12H_2O$, 0.3% $KH_2PO_4$, 0.05 NaCl, 0.1% $NH_4Cl$, 0.005% ampicillin, 0.2 mM IPTG, 1.5% agar) and the agar plate was incubated at 37° C. for 2 days. Strains growing on the plate and forming colonies were picked up and then incubated on LB medium at 37° C. for 16 hours. Plasmids were extracted from these strains by the alkali lysis method (Molecular Cloning, 2nd ed., Cold Spring Harbor Laboratory Press(1989)), cleaved with restriction enzymes and investigated by agarose gel electrophoresis to find that the recombinant plasmid introduced into each deletion mutant contained an inserted fragment having a size shown in Table 4.

TABLE 4

| Recombinant plasmids complementing defective strains for growth | | |
|---|---|---|
| Defective strain | Plasmid obtained | Size of inserted fragment |
| R874 | pBC11 | 2.3 |
| R879 | pBC12 | 2.2 |
|  | pBC13 | 2.6 |
| R875 | pBC14 | 1.9 |
| R876 | pBC15 | 2.0 |

(2-D) Analysis of the Base Sequence of a DNA Fragment Containing a Gene Concerned in Biotin Biosynthesis For the recombinant plasmids pBC11, pBC12, pBC13 pBC14 and pBC15 obtained in (2-C), deletion clones containing inserted fragments of various sizes were prepared by the use of a deletion kit for kilo sequence (available from TAKARA SHUZO Co., Ltd.) in the manner described below.

Twenty micrograms of each of the recombinant plasmids pBC11, pBC12, pBC13, pBC14 and pBC15 was cleaved with the following enzymes; pBC11: Xba I and Sse 8387 I, pBC12 and pBC13: Pst I and Xba I, pBC14 and pBC15: Xba I and Kpn I. The enzymes were removed by extraction with phenol, followed by precipitation of DNA with ethanol. The obtained DNA was dissolved in 100 µl of Exo III buffer (50 mM Tris-HCl (pH 8.0), 100 mM NaCl, 5 mM $MgCl_2$, 10 mM 2-mercaptoethanol), followed by adding thereto 180 units of exonuclease III, and the resulting mixture was stirred and then incubated at 37° C. At intervals of 1 minute, 10 µl of the resulting solution was sampled and then mixed with 100 µl of ice-cooled MB nuclease buffer (40 mM Na-acetate (pH 4.5), 100 mM NaCl, 2 mM $ZnCl_2$, 10% glycerol) and the exonuclease III was inactivated by treatment at 65° C. for 5 minutes. The thus obtained solution was cooled to 37° C. and then 50 units of MB nuclease was added, followed by incubation for 60 minutes. The enzymes were removed by extraction with phenol, followed by precipitation of DNA with ethanol. The obtained DNA was dissolved in 50 µl of Klenow buffer (7 mM Tris-HCl (pH 7.5), 0.1 mM EDTA, 20 mM NaCl, 7 mM MgCl$_2$, dNTP's 0.1 mM each) and 2 units of Klenow fragment was added, followed by incubation at 37° C. for 15 minutes. To 100 µl of ligation solution A were added 10 µl of the resulting solution and then 12 µl of ligation solution B, followed by incubation at 16° C. for 1 hour. Then, DNA was concentrated by precipitation with ethanol and dissolved in 5 µl of sterilized water, and the resulting solution was introduced into E. coli JM109. The thus treated E. coli JM109 was streaked on agar plate of ampicillin (0.005%)-containing LB culture medium (1% tryptone, 0.5% yeast extract, 1% NaCl, 1.5% agar) and the agar plate was incubated at 37° C. for 16 hours. Plasmids were extracted from the developed colonies and the sizes of the inserted DNA fragments were investigated. Nine clones containing inserted fragments, respectively, varying in size from 250 bp to 2.3 kbp by about 250 bp each were selected as deletion clones of pBC11. Eight clones containing inserted fragments, respectively, varying in size from 250 bp to 2.2 kbp by about 250 bp each were selected as deletion clones of pBC12. Ten clones containing inserted fragments, respectively, varying in size from 250 bp to 2.6 kbp by about 250 bp each were selected as deletion clones of pBC13. Eight clones containing inserted fragments, respectively, varying in size from 250 bp to 1.9 kbp by about 250 bp each were, selected as deletion clones of pBC14. Eight clones containing inserted fragments, respectively, varying in size from 250 bp to 2.0 kbp by about 250 bp each were selected as deletion clones of pBC15.

Each deletion clone was extracted by the alkali lysis method (Molecular Cloning, 2nd ed., Cold Spring Harbor Laboratory Press(1989)). Using 300 ng of the extract as a template and M13 primer M4 (available from TAKARA SHUZO Co., Ltd.) or M13 primer RV (available from TAKARA SHUZO Co., Ltd.) as a primer, sequence reaction was carried out by the use of an ABI prism dye terminator cycle sequencing ready reaction kit (mfd. by Perkin-Elmer Corporation), and the base sequence was analyzed by means of an automatic base sequence analyzer 373A (mfd. by Perkin-Elmer Corporation).

For specifying a gene concerned in biotin biosynthesis among the base sequences of the inserted fragments of the recombinant plasmids, regions coding for a protein which were highly homologous in base sequence with known bio F gene, bio A gene, bio D gene, bio B gene and bio C gene, respectively, were selected from open reading frames of 500 bp or more present in the fragments and specified as the genes of the bacterium of the genus Sphingomonas which correspond to the above genes, respectively. pBC11 contained bio F (SEQ ID NO: 5). Each of pBC12 and pBC13 contained bio D (SEQ ID NO: 19) and bio A (SEQ ID NO: 13). pBC14 contained bio B (SEQ ID NO: 25). pBC15 contained bio C (SEQ ID NO: 34). As a result of comparing the base sequences of the inserted fragments of pBC12, pBC13 and pBC15 which had been independently obtained, the following became clear: a combination of the inserted fragments of pBC12, pBC13 and pBC15 is continuous DNA on genome; the termination codon TGA of bio C and the initiation codon ATG of bio D overlap with each other at the base sequence TG; the termination codon TGA of bio D and the initiation codon ATG of bio A overlap with each other at the base sequence TG; and bio C, bio D and bio A forms an operon.

EXAMPLE 3

Preparation of a Recombinant Plasmid pJAW (E) Preparation of a Plasmid Vector pJA β2

One microgram of a plasmid vector pJAJ7 derived from a plasmid vector RK2 (Journal of Bacteriology, vol. 162, 604–614 (1986)) was cleaved with restriction enzymes Pst I and Bam HI, and both ends of the resulting fragments were blunted by the use of a DNA blunting kit (available from TAKARA SHUZO Co., Ltd.) according to the attached operating manual. The thus treated fragments were separated by agarose gel electrophoresis to isolate a DNA fragment of about 10 kbp. Separately, 2 µg of a plasmid vector pBluescript SK(+) (available from stratagene Cloning Systems) was cleaved with a restriction enzyme Hae III, and both ends of the resulting fragments were blunted by the use of the DNA blunting kit (available from TAKARA SHUZO Co., Ltd.) according to the attached operating manual. The thus treated fragments were separated by agarose gel electrophoresis to isolate a DNA fragment of about 0.7 kbp. The whole aprox. 10 kbp DNA fragment and the whole aprox. 0.7 kbp DNA fragment thus obtained were mixed and then ligated with each other by the use of a ligation kit (available from TAKARA SHUZO Co., Ltd.) according to the attached operating manual. The resulting plasmid was named pJA β2 (FIG. 1).

(F) Preparation of a Plasmid pJAW

Figure 2:
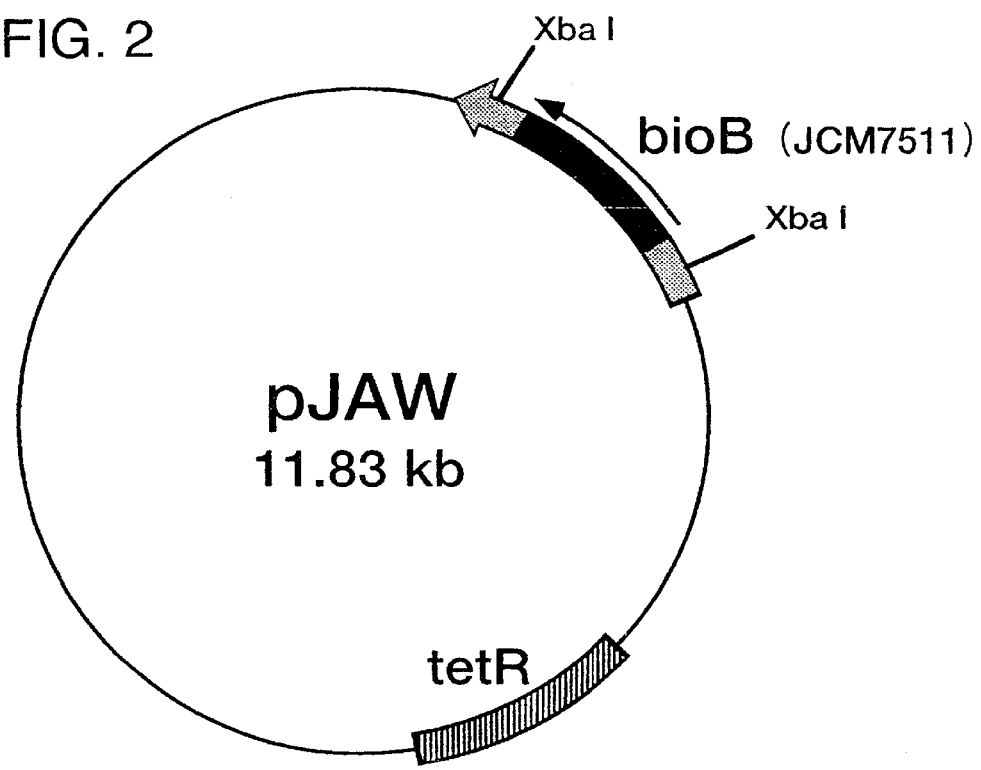
FIG. 2 shows the structure and restriction map of plasmid pJAW.

Using the genomic DNA obtained in Example 1, (1-A), as a template and the primers BF and BR shown in Table 5, there was carried out PCR [reaction composition: 10 mM Tris-HCl (pH 8.8), 10 mM KCl, 0,002(v/v)% Tween 20, 1.5 mM MgCl$_2$, 40 µM each dNTP, 20 pmol each primer, 0.5 to 100 ng genomic DNA, 3U UlTma™DNA polymerase (available from Perkin-Elmer Corporation)/100 µl; reaction cycles: 1 cycle of reaction at 97° C. for 2 minutes, 30 cycles of reactions at 97° C. for 1 minute, at 55° C. for 1 minute and then at 72° C. for 1.5 minutes, respectively, and 1 cycle of reaction at 72° C. for 7 minutes]. Thus, there was prepared a DNA fragment containing 1325 bp in total from 145 bp upstream to a coding region of bio B to 154 bp downstream to the coding region and having a Xba I site introduced into each end of the 1325 bp sequence. This DNA fragment was cleaved with a restriction enzyme Xba I, and the resulting DNA fragment and a DNA fragment obtained by cleaving the plasmid vector pJA β2 with a restriction enzyme Xba I and dephosphorylating the cleaved plasmid vector were mixed and then ligated with each other by the use of a ligation kit (available from TAKARA SHUZO Co., Ltd.) according to the attached operating manual. The plasmid thus obtained was named pJAW (FIG. 2).

TABLE 5

PCR primers

| Primer | Base sequence |
|---|---|
| BF | 5'-ATTCTAGAACAGGACTATCAGGCACTCT-3' |
| BR | 5'-TTTCTAGATTCCCCGCGATTGGCGATCA-3' |
| BF1 | 5'-AGCGGCCGAGGATGTGCTTAGGCTGCT-3' |
| BR1 | 5'-CCGTGCCCTTGACCGACACCAGCGCGT-3' |
| C1 | 5'-GCAAGCTTTGTCGCTGCCGCTCGTCATGCTGT-3' |
| C6 | 5'-CGCTCGAGATTCGCGCTTCCTGTTCCTGAC-3' |

EXAMPLE 4

Preparation of Transformants Having pJAW Introduced Thereinto

Sphingomonas paucimobilis JCM7511/pJAW was obtained as transformants by introducing the plasmid pJAW obtained in Example 3 into *Sphingomonas paucimobilis* JCM7511 with a gene pulser (mfd. by Bio-Rad Laboratories Inc.) by an electroporation method (applied voltage 18 kV/cm, capacitance 25 µF, resistance 400Ω).

EXAMPLE 5

Preparation of a Recombinant Plasmid pJA41

Figure 3:
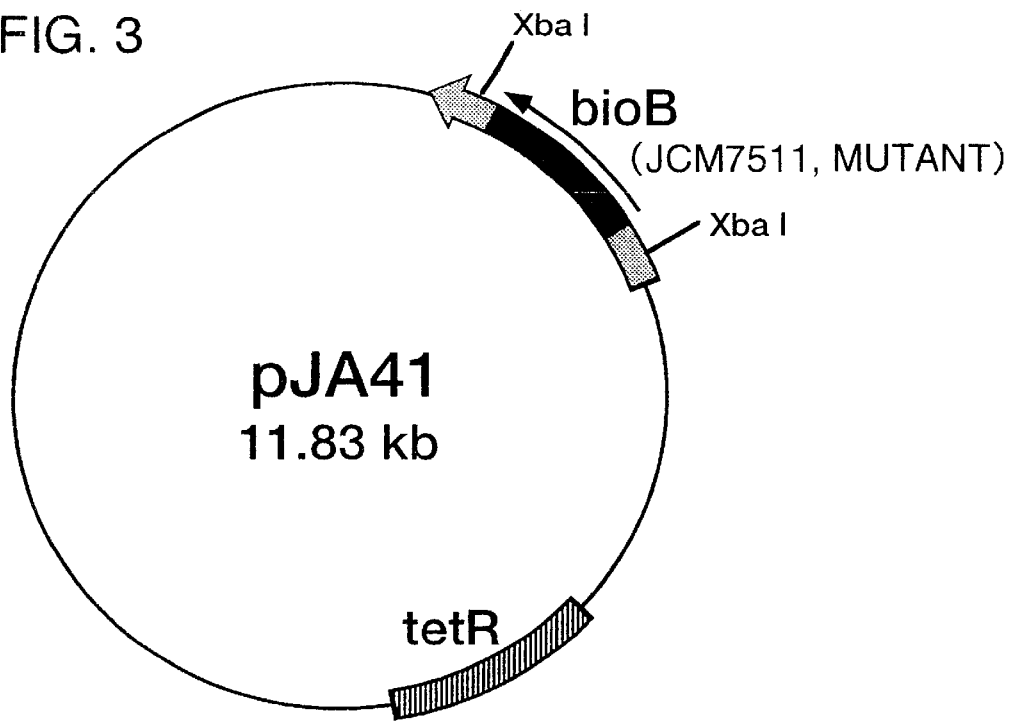
FIG. 3 shows the structure and restriction map of plasmid pJA41.

DNA fragments obtained by partially digesting the plasmid pJAW obtained in Example 3 with restriction enzymes Eco 52I and Bsp 1286I were separated by agarose gel electrophoresis to recover a DNA fragment of about 11.8 kbp formed by the deletion from pJAW of a base sequence from the −72th base to the 718th base in the case of taking A of the initiation codon ATG of bio B as the +1st base. On the other hand, using the genomic DNA obtained in Example 1, (1-A), as a template and the primers BF1 and BR1 shown in Table 5, there was carried out PCR [reaction composition: 10 10 mM Tris-HCl (pH 8.8), 10 mM KCl, 0,002(v/v)% Tween 20, 1.5 mM $MgCl_2$, 40 µM each dNTP, 20 pmol each primer, 0.5 to 100 ng genomic DNA, 3U UlTma™DNA polymerase (available from Perkin-Elmer Corporation)/100 µl; reaction cycles: 1 cycle of reaction at 97° C. for 1 minute, 30 cycles of reactions at 970C for 0.5 minute, at 60° C. for 1 minute and then at 72° C. for 1.5 minutes, respectively, and 1 cycle of reaction at 72° C. for 7 minutes]. Thus, there was prepared a DNA fragment having a base sequence from the −75th base to the 721th base in the case of taking A of the initiation codon ATG of bio B as the +1st base. Then, this DNA fragment was partially digested with restriction enzymes Eco 52I and Bsp 1286I and the resulting DNA fragments were separated by agarose gel electrophoresis to recover a DNA fragment of about 0.8 kbp. The base sequence of the recovered DNA fragment was analyzed to confirm a base sequence of base Nos. 1 to 1336 shown in SEQ ID NO: 28. The DNA fragments thus obtained were ligated with each other by the use of a ligation kit (available from TAKARA SHUZO Co., Ltd.) according to the attached operating manual. The plasmid thus obtained was named pJA41 (FIG. 3).

EXAMPLE 6

Preparation of Transformants Having pJA41 Introduced Thereinto

*Sphingomonas paucimobilis* JCM7511/pJA41 was obtained by introducing the plasmid pJA41 obtained in Example 5 into *Sphingomonas paucimobilis* JCM7511 with a gene pulser (mfd. by Bio-Rad Laboratories Inc.) by an electroporation method (applied voltage 18 kV/cm, capacitance 25 µF, resistance 400Ω).

EXAMPLE 7

Biotin Productivity of *Sphingomonas Paucimobilis* JCM7511/pJAW and JCM7511/pJA41

A loopful of each of *Sphingomonas paucimobilis* JCM7511/pJAW and Sphingomonas paucimobilis JCM7511/pJA41 was inoculated into a small test tube (18× 150 mm) containing 3 ml of a culture medium (1% glycerol, 2% peptone, 0.15% $K_2HPO_4$, 0.15% $MgSO_4$ $7H_2O$, 0.005% tetracycline (pH 7.2)). As a control, a loopful of *Sphingomonas paucimobilis* JCM7511 having no gene introduced thereinto was inoculated into a small test tube (18×150 mm) containing 3 ml of a culture medium (1% glycerol, 2% peptone, 0.15% $K_2HPO_4$ 0.15% $MgSO_4$ $7H_2O$ (pH 7.2)). The above three kinds of the bacteria were cultured at 30° C. for 2 days (250 rpm) to obtain pre-culture broths. Then, 200 µl of each of the thus obtained pre-culture broths of *Sphingomonas paucimobilis* JCM7511/pJAW and *Sphingomonas paucimobilis* JCM7511/pJA41 was inoculated into a large test tube (22×220 mm) containing 10 ml of a culture medium (4% glycerol, 2% yeast extract, 0.5% casamino acid, 0.1% $K_2HPO_4$, 0.05% KCl, 0.05% $MgSO_4$-$7H_2O$, 0.001% $FeSO_4$-$7H_2O$, 0.001% $MnSO_4$-4–$6H_2O$, 0.000002% thiamine HCl, 0.005% tetracycline (pH 7.0)). As a control, 200 µl of the pre-culture broth of *Sphingomonas paucimobilis* JCM7511 was inoculated into a large test tube (22×220 mm) containing 10 ml of a culture medium (4% glycerol, 2% yeast extract, 0.5% casamino acid, 0.1% $K_2HPO_4$, 0.05% KCl, 0.05% $MgSO_4$-$7H_2O$, 0.001% $FeSO_4$-$7H_2O$, 0.001% $MnSO_4$-4–$6H_2O$, 0.000002% thiamine HCl (pH 7.0)). The above three kinds of the bacteria were cultured at 30° C. for 4 days (250 rpm). The concentration of biotin produced and accumulated in each culture broth was determined by a microbiological quantitation method using *Lactobacillus plantarum* IFO 3070 strain (Izumi and Yamada "Vitaminological Experimental Method II. Water-soluble Vitamins", p. 481–499, Vitaminological Society of Japan, Tokyo Kagaku Dojin, 1985) to find that the concentration of biotin produced was as shown in Table 6.

TABLE 6

| Strain | Biotin productivity* | Biotin concentration (mg/L) |
|---|---|---|
| *Sphingomonas paucimobilis* JCM7511 | 1 | 0.037 |
| *Sphingomonas paucimobilis* JCM7511/pJAW | 2.1 | 0.078 |
| *Sphingomonas paucimobilis* JCM7511/pJA41 | 6.9 | 0.260 |

EXAMPLE 8

Preparation of a Recombinant Plasmid pSP302

The plasmid pBC01 obtained in Example 1 was cleaved with restriction enzymes Bam HI and Pst I and the resulting DNA fragments were separated by agarose gel electrophoresis to obtain a DNA fragment of about 1.4 kbp containing a large portion of a coding region of bio F and a region controlling the expression of bio F, bio D and bio A which region was upstream to bio F. The thus obtained DNA fragment and a plasmid vector pBluescript SKII(+) (available from Stratagene Cloning Systems) cleaved by restriction enzymes Bam HI and Pst I were mixed and then ligated with each other by the use of a ligation kit (available from TAKARA SHUZO Co., Ltd.) according to the attached operating manual. The plasmid thus obtained was named pBC06.

In addition, the plasmid pBC02 obtained in Example 1 was cleaved with restriction enzymes Pst I and Eco RI and the resulting DNA fragments were separated by agarose gel electrophoresis to obtain a DNA fragment of about 2.2 kbp containing a portion of coding region of bio F, coding regions of bio D and bio A, and a 3'-untranslated region of bio F, bio D and bio A which was downstream to bio A. The thus obtained DNA fragment and a plasmid pBC06 cleaved by restriction enzymes Pst I and Eco RI were mixed and then ligated with each other by the use of a ligation kit (available from TAKARA SHUZO Co., Ltd.) according to the attached operating manual. The plasmid thus obtained was named pSP105.

Figure 4:
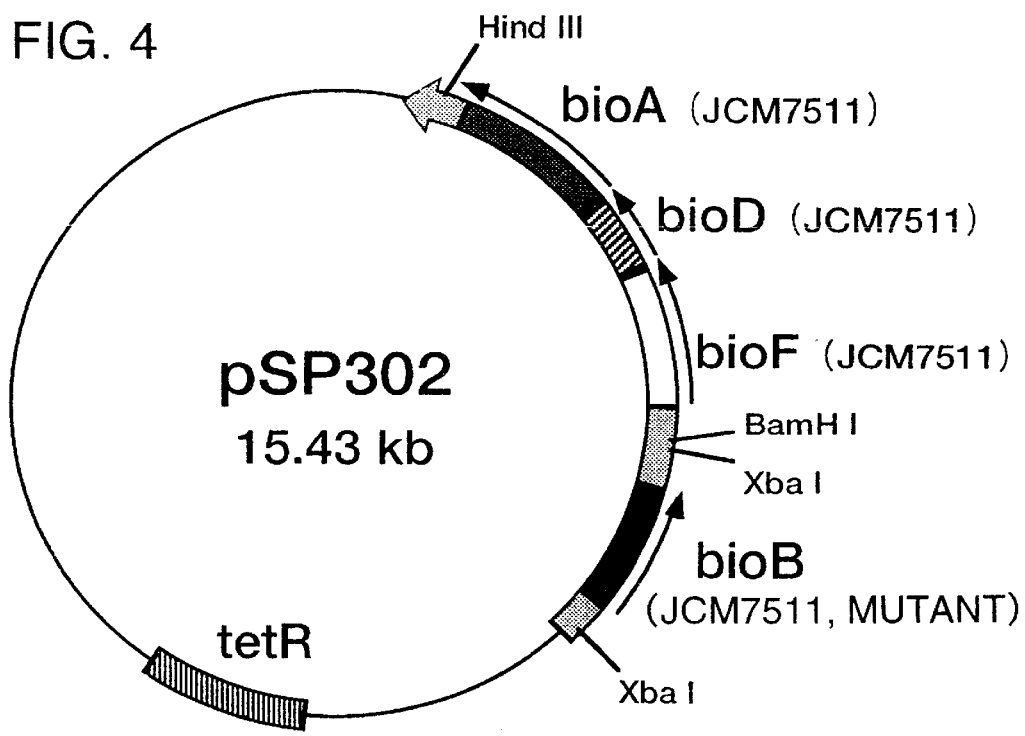
FIG. 4 shows the structure and restriction map of plasmid pSP302.

Further, the plasmid pSP105 was cleaved with restriction enzymes Bam HI and Hind III and the resulting DNA fragments were separated by agarose gel electrophoresis to obtain a DNA fragment of about 3.6 kbp containing coding regions of bio F, bio D and bio A and a region regulating the expression of bio F, bio D and bio A. The thus obtained DNA fragment and a plasmid pJA41 cleaved by restriction enzymes Bam HI and Hind III were mixed and then ligated with each other by the use of a ligation kit (available from TAKARA SHUZO Co., Ltd.) according to the attached operating manual. The plasmid thus obtained was named pSP302 (FIG. 4).

EXAMPLE 9

Preparation of Transformants Having pSP302 Introduced Thereinto

*Sphingomonas paucimobilis* JCM7511/pSP302 was obtained by introducing the plasmid pSP302 obtained in Example 8 into *Sphingomonas paucimobilis* JCM7511 with a gene pulser (mfd. by Bio-Rad Laboratories Inc.) by an electroporation method (applied voltage 18 kV/cm, capacitance 25 $\mu$F, resistance 400$\Omega$).

EXAMPLE 10

Preparation of a Recombinant Plasmid pSP304

Figure 5:
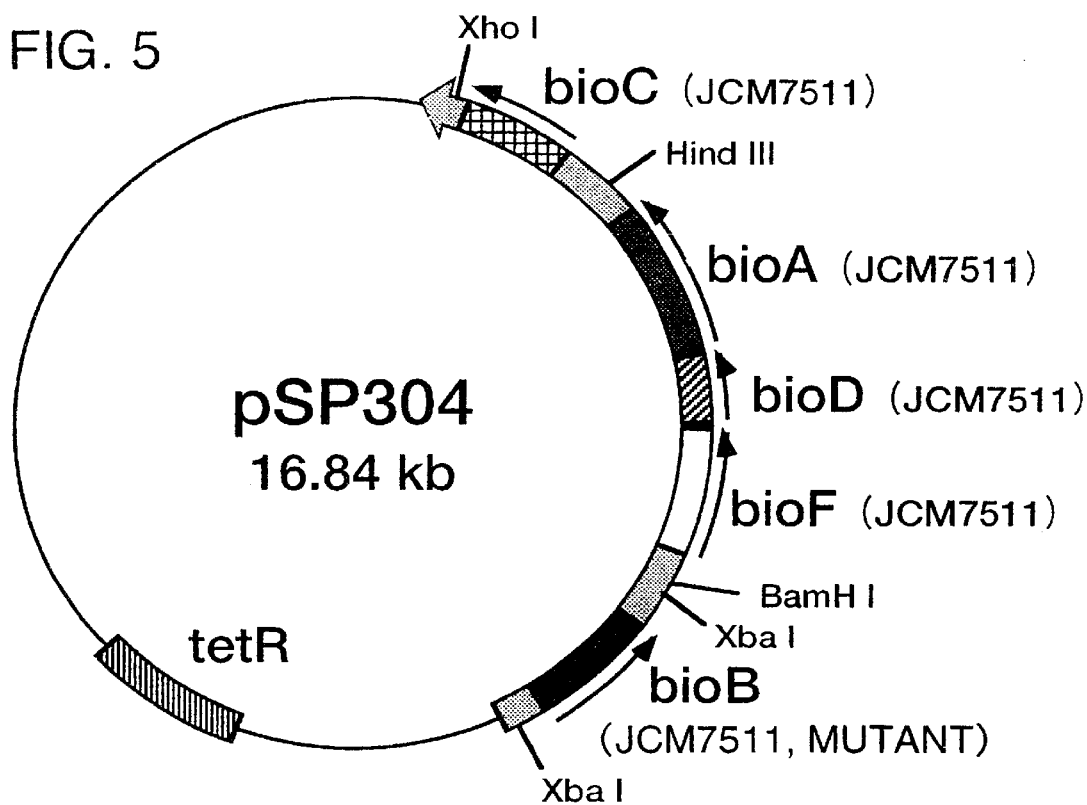
FIG. 5 shows the structure and restriction map of plasmid pSP304.

PCR was carried out using the genomic DNA obtained in Example 1, (1-A), as a template and the primers C1 and C6 shown in Table 5, to prepare a DNA fragment containing 1435 bp in total from 387 bp upstream to a coding region of bio C to 196 bp downstream to the coding region and having a Hind III site introduced into the upstream end of the 1435 bp sequence and a Xho I site introduced into the downstream end. A fragment obtained by cleaving this DNA fragment with restriction enzymes Hind III and Xho I and a DNA fragment obtained by cleaving the plasmid pSP302 with restriction enzymes Hind III and Xho I were mixed and then ligated with each other by the use of a ligation kit (available from TAKARA SHUZO Co., Ltd.) according to the attached operating manual. The plasmid thus obtained was named pSP304 (FIG. 5).

EXAMPLE 11

Preparation of Transformants Having pSP304 Introduced Thereinto

*Sphingomonas paucimobilis* JCM7511/pSP304 was obtained by introducing the plasmid pSP304 obtained in Example 10 into *Sphingomonas paucimobilis* JCM7511 with a gene pulser (mfd. by Bio-Rad Laboratories Inc.) by an electroporation method (applied voltage 18 kV/cm, capacitance 25 $\mu$F, resistance 400$\Omega$).

EXAMPLE 12

Biotin productivity of *Sphingomonas Paucimobilis* JCM7511/pSP302 and JCM7511/pSP304

A loopful of each of *Sphingomonas paucimobilis* JCM7511/pSP302 and *Sphingomonas paucimobilis* JCM7511/pSP302 was inoculated into a small test tube (18×150 mm) containing 3 ml of a culture medium (1% glycerol, 2% peptone, 0.15% $K_2HPO_4$, 0.15% $MgSO_4 \cdot 7H_2O$, 0.005% tetracycline (pH 7.2)). As a control, a loopful of *Sphingomonas paucimobilis* JCM7511 having no gene introduced thereinto was inoculated into a small test tube (18×150 mm) containing 3 ml of a culture medium (1% glycerol, 2% peptone, 0.15% $K_2HPO_4$ 0.15% $MgSO_4 \cdot 7H_2O$ (pH 7.2)). The above three kinds of the bacteria were cultured at 30° C. for 2 days (250 rpm) to obtain pre-culture broths. Then, 200 $\mu$l of each of the thus obtained pre-culture broths of *Sphingomonas paucimobilis* JCM7511/pSP302 and *Sphingomonas paucimobilis* JCM7511/pSP304 was inoculated into a large test tube (22×220 mm) containing 10 ml of a culture medium (4% glycerol, 2% yeast extract, 0.5% casamino acid, 0.1% $K_2HPO_4$, 0.05% KCl, 0.05% $MgSO_4 \cdot 7H_2O$, 0.001% $FeSO_4 \cdot 7H_2O$, 0.001% $MnSO_4$-4–6$H_2O$, 0.005% tetracycline (pH 7.0)). As a control, 200 $\mu$l of the pre-culture broth of *Sphingomonas paucimobilis* JCM7511 was inoculated into a large test tube (22×220 mm) containing 10 ml of a culture medium (4% glycerol, 2% yeast extract, 0.5% casamino acid, 0.1% $K_2HPO_4$, 0.05% KCl, 0.05% $MgSO_4 \cdot 7H_2O$, 0.001% $FeSO_4 \cdot 7H_2O$, 0.001% $MnSO_4$-4–6$H_2O$ (pH 7.0)). The above three kinds of the bacteria were cultured at 30° C. for 4 days (250 rpm). The concentration of biotin produced and accumulated in each culture broth was determined by the microbiological quantitation method using Lactobacillus plantarum IFO 3070 strain (Izumi and Yamada "Vitaminological Experimental Method II. Water-soluble Vitamins", p. 481–499, Vitaminological Society of Japan, Tokyo Kagaku Dojin, 1985) to find that the concentration of biotin produced was as shown in Table 7.

TABLE 7

Biotin productivity of *Sphingomonas paucimobilis* JCM7511/pSP305

| Strain | Biotin productivity* | Biotin concentration (mg/L) |
|---|---|---|
| *Sphingomonas paucimobilis* JCM7511 | 1 | 0.12 |
| *Sphingomonas paucimobilis* JCM7511/pSP302 | 2.8 | 0.33 |
| *Sphingomonas paucimobilis* JCM7511/pSP304 | 8.6 | 1.0 |

*Values relative to the biotin productivity of the strain having no gene introduced thereinto.

EXAMPLE 13

Preparation of a Recombinant Plasmid pSS301

Figure 6:
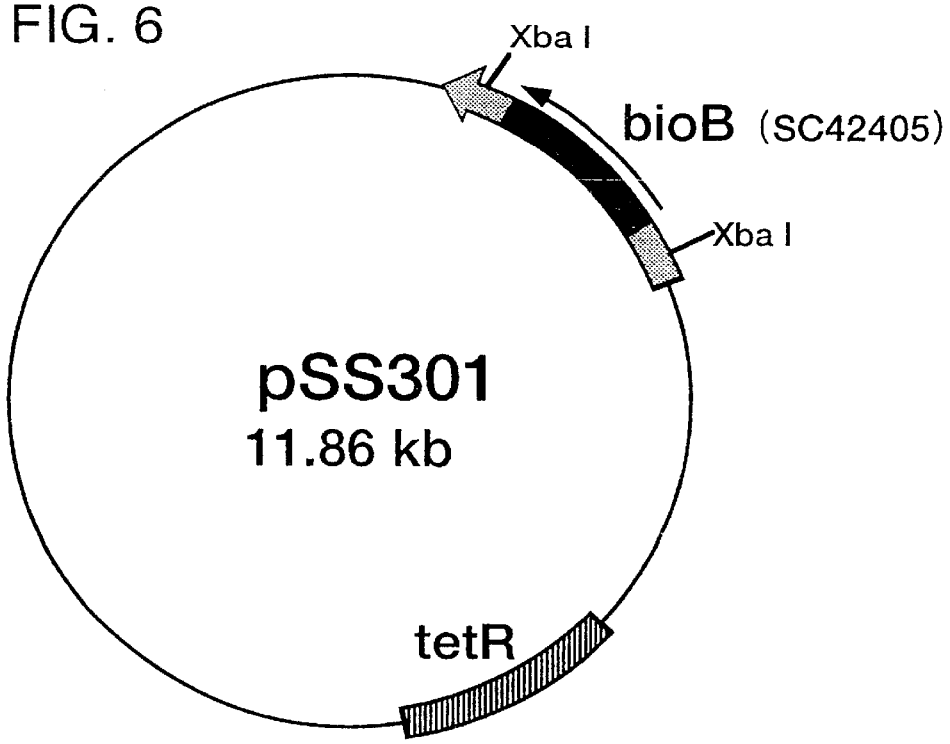
FIG. 6 shows the structure and restriction map of plasmid pSS301.

Using the genomic DNA obtained in Example 2, (2-A), as a template and the primers BF4 and BR4 shown in Table 8, there was carried out PCR [reaction composition: 1×Expand HF buffer, 1.5 mM $MgCl_2$, 200 $\mu$M each dNTP, 300 nM each primer, 0.5 to 100 ng genomic DNA, 2.6 U Expand™ high fidelity PCR System enzyme mix (available from Boehringer Mannheim Co., Ltd.)/50 $\mu$l; reaction cycles: 1 cycle of reaction at 97° C. for 2 minutes, 10 cycles of reactions at 97° C. for 15 seconds, at 60° C. for 30 seconds and then at 72° C. for 1.5 minutes, respectively, 15 cycles of reactions at 97° C. for 15 seconds, at 60° C. for 30 seconds and then at 72° C. for 1.5 minutes (the time of the reaction at 72° C. for 1.5 minutes was increased by 20 seconds in every cycle), respectively, and 1 cycle of reaction at 72° C. for 7 minutes]. Thus, there was prepared a DNA fragment containing 1358 bp in total from 151 bp upstream to a coding region of bio B to 151 bp downstream to the coding region and having a Xba I site introduced into each end of the 1358 bp sequence. This DNA fragment was cleaved with a restriction enzyme Xba I, and the resulting DNA fragment and a DNA fragment obtained by cleaving the plasmid vector pJA 82 with a restriction enzyme Xba I and dephosphorylating the cleaved plasmid vector were mixed and then ligated with each other by the use of a ligation kit (available from TAKARA SHUZO Co., Ltd.) according to the attached operating manual. The plasmid thus obtained was named pSS301 (FIG. 6).

TABLE 8

| Primer | Base sequence |
|---|---|
| BF4 | 5'-CGTGATGCTGCGCCTGCTCGGCCACAACAT-3' |
| BR4 | 5'-GCTCTAGACCTCATCGTCCCCCTGAACTTGTT-3' |
| F2 | 5'-GGACTAGTACCGGAATGACAGGCGGACA-3' |
| F3 | 5'-GCCTGCAGCAGAACGTGTGGTCGAAGCC-3' |
| CDA1 | 5'-ATCTGCAGTTGCGCGATGAGGAGGCCACCTTGC-3' |
| CDA6 | 5'-GCAAGCTTATGACGCCGCCTGCGCCTTCGACCA-3' |
| CDA3 | 5'-CTAAGCTTCGAGATCGACGGGGTGGAAATCGAT-3' |
| CDA7 | 5'-CGCTCGAGGGGAGAAGTCCTGGGGGATGATCCC-3' |
| R1 | 5'-CCCTGCCCGTATGGCAAGCG-3' |
| (SEQ ID NO:52) | |

EXAMPLE 14

Preparation of Transformants Having pSS301 Introduced Thereinto

Sphingomonas sp. SC42405/pSS301 was obtained as transformants by introducing the plasmid pSS301 obtained in Example 13 into sphingomonas sp. SC42405 with a gene pulser (mfd. by Bio-Rad Laboratories Inc.) by an electroporation method (applied voltage 18 kV/cm, capacitance 25 µF, resistance 400Ω).

EXAMPLE 15

Biotin Productivity of Sphingomonas sp. SC42405/pSS301

A loopful of Sphingomonas sp. SC42405/pSS301 was inoculated into a small test tube (18×150 mm) containing 3 ml of a culture medium (1% glycerol, 2% peptone, 0.15% $K_2HPO_4$, 0.15% $MgSO_4 \cdot 7H_2O$, 0.005% tetracycline (pH 7.2)). As a control, a loopful of Sphingomonas sp. SC42405 having no gene introduced thereinto was inoculated into a small test tube (18×150 mm) containing 3 ml of a culture medium (1% glycerol, 2% peptone, 0.15% $K_2HPO_4$ 0.15% $MgSO_4 \cdot 7H_2O$ (pH 7.2)). The above two kinds of the bacteria were cultured at 30° C. for 2 days (250 rpm) to obtain pre-culture broths. Then, 160 µl of the thus obtained pre-culture broth of Sphingomonas sp. SC42405/pSS301 was inoculated into a large test tube (22×220 mm) containing 8 ml of a culture medium (6% glycerol, 2% yeast extract, 0.5% casamino acid, 0.1% $K_2HPO_4$, 0.05% KCl, 0.05% $MgSO_4 \cdot 7H_2O$, 0.01% $FeSO_4 \cdot 7H_2O$, 0.1% $MnSO_4 \cdot 4 \sim 6H_2O$, 0.005% tetracycline (pH 7.0)). As a control, 160 µl of the pre-culture broth of Sphingomonas sp. SC42405 was inoculated into a large test tube (22×220 mm) containing 8 ml of a culture medium (6% glycerol, 2% yeast extract, 0.5% casamino acid, 0.1% $K_2HPO_4$, 0.05% KCl, 0.05% $MgSO_4 \cdot 7H_2O$, 0.01% $FeSO_4 \cdot 7H_2O$, 0.1% $MnSO_4 \cdot 4 \sim 6H_2O$ (pH 7.0)). The above two kinds of the bacteria were cultured at 30° C. for 4 days (250 rpm).

The concentration of biotin produced and accumulated in each culture broth was determined by the microbiological quantitation method using Lactobacillus plantarum IFO 3070 strain (Izumi and Yamada "Vitaminological Experimental Method II. Water-soluble Vitamins", p. 481–499, Vitaminological Society of Japan, Tokyo Kagaku Dojin, 1985) to find that the concentration of biotin produced was as shown in Table 9.

TABLE 9

| Strain | Biotin productivity* | Biotin concentration (mg/L) |
|---|---|---|
| Sphingomonas sp. SC42405 | 1 | 4.1 |
| Sphingomonas sp. C42405/pSS301 | 4.0 | 17 |

*Values relative to the biotin productivity of the strain having no gene introduced thereinto.

EXAMPLE 16

Preparation of a Recombinant Plasmid pSS305

Using the genomic DNA obtained in Example 2, (2-A), as a template and the primers F2 and F3 shown in Table 8, there was carried out PCR [reaction composition: 1×Expand HF buffer, 1.5 mM $MgCl_2$, 200 AM each dNTP, 300 nM each primer, 0.5 to 100 ng genomic DNA, 2.6 U Expand™ high fidelity PCR System enzyme mix (available from Boehringer Mannheim Co., Ltd.)/50 µl; reaction cycles: 1 cycle of reaction at 97° C. for 2 minutes, 10 cycles of reactions at 97° C. for 15 seconds, at 60° C. for 30 seconds and then at 72° C. for 1.5 minutes, respectively, 15 cycles of reactions at 97° C. for 15 seconds, at 60° C. for 30 seconds and then at 72° C. for 1.5 minutes (the time of the reaction at 72° C. for 1.5 minutes was increased by 20 seconds in every cycle), respectively, and 1 cycle of reaction at 72° C. for 7 minutes]. Thus, there was prepared a DNA fragment containing 1408 bp in total from 201 bp upstream to a coding region of bio F to 46 bp downstream to the coding region and having a Spe I site introduced into the upstream end of the 1408 bp sequence and a Pst I site introduced into the downstream end. This DNA fragment was cleaved with a restriction enzymes Spe I and Pst I, and the resulting DNA fragment and a DNA fragment obtained by cleaving a plasmid vector pBluescript SK(+) (available from Stratagene Cloning Systems) with restriction enzymes Spe I and Pst I were mixed and then ligated with each other by the use of a ligation kit (available from TAKARA SHUZO Co., Ltd.) according to the attached operating manual. The plasmid thus obtained was named pSS202.

In addition, using the genomic DNA obtained in Example 2, (2-A), as a template and the primers CDA1 and CDA6 shown in Table 8, there was carried out PCR [reaction composition: 1×Expand HF buffer, 1.5 mM $MgCl_2$, 200 µM each dNTP, 300 nM each primer, 0.5 to 100 ng genomic DNA, 2.6 U Expan™ high fidelity PCR System enzyme mix (available from Boehringer Mannheim Co., Ltd.)/50 µl; reaction cycles: 1 cycle of reaction at 97° C. for 2 minutes, 10 cycles of reactions at 97° C. for 15 seconds, at 60° C. for 30 seconds and then at 72° C. for 1.5 minutes, respectively, 15 cycles of reactions at 97° C. for 15 seconds, at 60° C. for 30 seconds and then at 72° C. for 1.5 minutes (the time of the reaction at 72° C. for 1.5 minutes was increased by 20 seconds in every cycle), respectively, and 1 cycle of reaction at 72° C. for 7 minutes]. Thus, there was prepared a DNA fragment which contained 1287 bp (in total) composed of a 209 bp sequence upstream to a coding region of bio C, the 726 bp coding region of bio C and the first half about 300 bp of a coding region of bio D, and had a Pst I site introduced into the upstream end of the 1287 bp sequence and a Hind III site introduced into the downstream end. This DNA fragment was cleaved with a restriction enzyme Pst I and Hind III, and the resulting DNA fragment and a DNA fragment obtained by cleaving a plasmid vector pbluescript SK(+) (available from Stratagene Cloning Systems) with restriction enzymes Pst I and Hind III were mixed and then ligated with each other by the use of a ligation kit (available from TAKARA SHUZO Co., Ltd.) according to the attached operating manual. The plasmid thus obtained was named pSS205.

Further, using the genomic DNA obtained in Example 2, (2-A), as a template and the primers CDA3 and CDA7 shown in Table 8, there was carried out PCR [reaction composition: 1×Expand HF buffer, 1.5 mM $MgCl_2$, 200 $\mu$M each dNTP, 300 nM each primer, 0.5 to 100 ng genomic DNA, 2.6 U Expand™ high fidelity PCR System enzyme mix (available from Boehringer Mannheim Co., Ltd.)/50 $\mu$l; reaction cycles: 1 cycle of reaction at 97° C. for 2 minutes, 10 cycles of reactions at 97° C. for 15 seconds, at 60° C. for 30 seconds and then at 72° C. for 1.5 minutes, respectively, 15 cycles of reactions at 97° C. for 15 seconds, at 60° C. for 30 seconds and then at 72° C. for 1.5 minutes (the time of the reaction at 72° C. for 1.5 minutes was increased by 20 seconds in every cycle), respectively, and 1 cycle of reaction at 72° C. for 7 minutes]. Thus, there was prepared a DNA fragment which contained 1653 bp (in total) composed of the second half about 400 bp of a coding region of bio D, a 1251 bp coding region of bio A, a 208 bp sequence downstream to the coding region of bio A, and had a Hind III site introduced into the upstream end of the 1653 bp sequence and a Xho I site introduced into the downstream end. This DNA fragment was cleaved with restriction enzymes Hind III and Xho I, and the resulting fragment and a DNA fragment obtained by cleaving a plasmid vector pBluescript SK(+) (available from Stratagene Cloning Systems) with restriction enzymes Hind III and Xho I were mixed and then ligated with each other by the use of a ligation kit (available from TAKARA SHUZO Co., Ltd.) according to the attached operating manual. The plasmid thus obtained was named pSS206.

The plasmid pSS205 obtained in the manner described above was cleaved with restriction enzymes Pst I and Hind III, and the resulting DNA fragments were separated by agarose electrophoresis to prepare a DNA fragment which contained 1287 bp (in total) composed of a 209 bp sequence upstream to a coding region of bio C, the 762 bp coding region of bio C and the first half about 300 bp of a cording region of bio D, and had a Pst I site introduced into the upstream end of the 1287 sequence and a Hind III site introduced into the downstream end. The thus obtained DNA fragment and pSS206 cleaved by restriction enzymes Pst I and Hind III were mixed and these DNA fragments were ligated with each other by the use of a ligation kit (available from TAKARA SHUZO Co., Ltd.) according to the attached operating manual. The plasmid thus obtained was named pSS2071.

Next, pSS2071 was cleaved with a restriction enzyme Cla I and the resulting DNA fragments were subjected to self ligation by the use of a ligation kit (available from TAKARA SHUZO Co., Ltd.) according to the attached operating manual. The plasmid thus obtained was named pSS207.

In addition, the plasmid pSS202 was cleaved with restriction enzymes Spe I and Pst I, and the resulting DNA fragments were separated by agarose electrophoresis to prepare a DNA fragment containing 1408 bp in total from 201 bp upstream to a coding region of bio F to 46 bp downstream to the coding region, and having Spe I site introduced into the upstream end of the 1406 bp sequence and a Pst I site introduced into the downstream end. The thus obtained DNA fragment was mixed with pSS207 cleaved by restriction enzymes Spe I and Pst I and these DNA fragments were ligated with each other by the use of a ligation kit (available from TAKARA SHUZO Co., Ltd.) according to the attached operating manual. The plasmid thus obtained was named pSS209.

Figure 7:
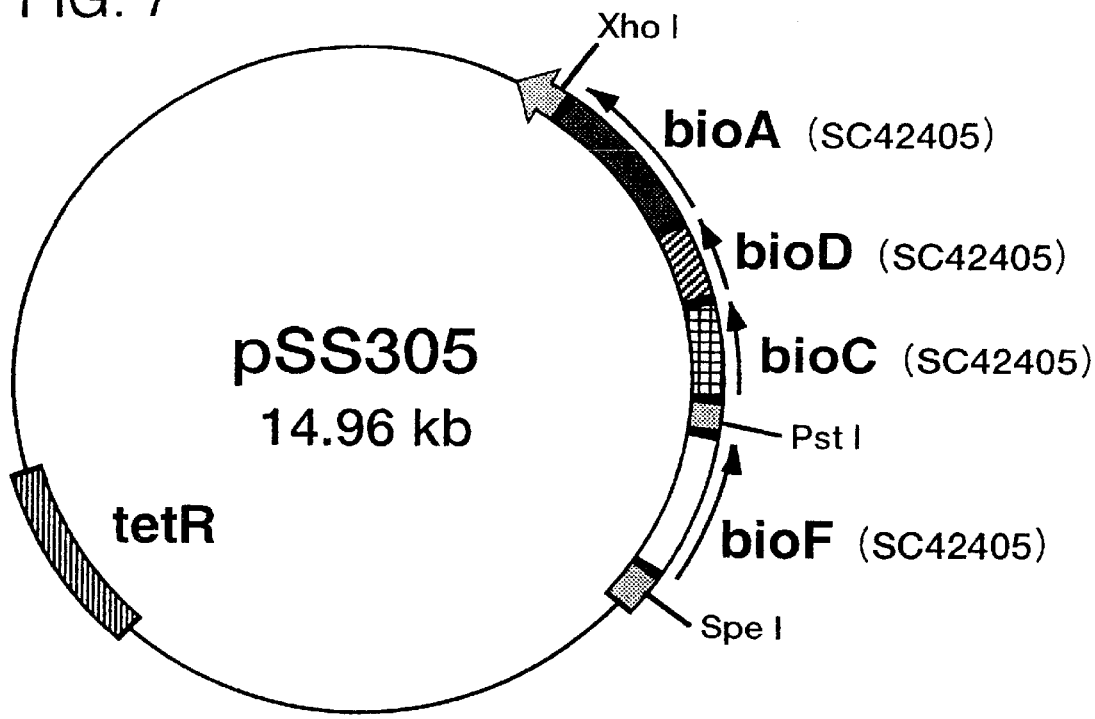
FIG. 7 shows the structure and restriction map of plasmid pSS305.

The plasmid pSS209 was cleaved with restriction enzymes Spe I and Xho I, and the resulting DNA fragments were separated by agarose electrophoresis to prepare a DNA fragment containing bio F, bio C, bio D and bio A and having a Spe I site introduced into the upstream end and a Xho I site introduced into the downstream end. The thus obtained DNA fragment was mixed with pJA β2 cleaved by restriction enzymes Spe I and Xho I and these DNA fragments were ligated with each other by the use of a ligation kit (available from TAKARA SHUZO Co., Ltd.) according to the attached operating manual. The plasmid thus obtained was named pSS305 (FIG. 7).

EXAMPLE 17

Preparation of a Recombinant Plasmid pSS304

Using the plasmid pSS305 obtained in Example 16, as a template and each of a combination of M13 primer RV (available from TAKARA SHUZO Co., Ltd.) and the primer R1 shown in Table 8 and a combination of M13 primer M4 (available from TAKARA SHUZO Co., Ltd.) and MUTB1 primer (available from TAKARA SHUZO Co., Ltd.), there was carried out PCR [reaction composition: 1×Expand HF buffer, 1.5 mM $MgCl_2$, 200 $\mu$M each dNTP, 300 nM each primer, 0.5 to 100 ng template DNA, 2.6 U Expand™ high fidelity PCR System enzyme mix (available from Boehringer Mannheim Co., Ltd.)/50 $\mu$l; reaction cycles: 1 cycle of reaction at 97° C. for 2 minutes, 10 cycles of reactions at 97° C. for 15 seconds, at 60° C. for 30 seconds and then at 72° C. for 1.5 minutes, respectively, 15 cycles of reactions at 97° C. for 15seconds, at 60° C. for 30 seconds and then at 72° C. for 1.5 minutes (the time of the reaction at 72° C. for 1.5 minutes was increased by 20 seconds in every cycle), respectively, and 1 cycle of reaction at 72° C. for 7 minutes]. The excess primers and the excess dNTP's were removed from the reaction solution after PCR by means of Centricon-100 (mfd. by Amicon Inc.), after which TF buffer was added to the residue to make a total volume of 50 $\mu$l. Then, 0.5 $\mu$l each of the thus obtained solutions were mixed. To the resulting mixture were added 50 $\mu$l of 10×Expand HF buffer, 4 $\mu$l of each 2.5 mM dNTP, 38.62 $\mu$l of sterilized distilled water and 0.38 $\mu$l of Expand™ high fidelity PCR System enzyme mix (3.5 U/$\mu$l) (available from Boehringer Mannheim Co., Ltd.), and the mixture thus obtained was heated at 94° C. for 10 minutes, cooled to 37° C. over a period of 60 minutes, and then incubated at 37° C. for 15 minutes. To this reaction solution were added 0.5 $\mu$l of 20 pmol M13 primer RV (available from TAKARA SHUZO Co., Ltd.) and 0.5 $\mu$l of 20 pmol M13 primer M4 (available from TAKARA SHUZO Co., Ltd.), followed by PCR [reaction cycles: 1 cycle of reaction at 97° C. for 2 minutes, 10 cycles of reactions at 97° C. for 15 seconds, at 60° C. for 30 seconds and then at 72° C. for 1.5 minutes, respectively, 15 cycles of reactions at 97° C. for 15 seconds, at 60° C. for 30 seconds and then at 72° C. for 1.5 minutes (the time of the reaction at 72° C. for 1.5 minutes was increased by 20 seconds in every cycle), respectively, and 1 cycle of reaction at 72° C. for 7 minutes]. The DNA fragment thus obtained was cleaved with restriction enzymes Not I and Hind III and mixed with a plasmid vector pBluescript SK(+) (available from Stratagene Cloning Systems) cleaved by restriction enzymes Not I and Hind III, followed by ligation by the use of a ligation kit (available from TAKARA SHUZO Co., Ltd.) according to the attached operating manual. From the resulting clones, a clone having a base sequence (SEQ ID NO: 7) of mutant bio F having G as a substituent for the −11th base C in the case of taking A of the initiation codon (ATG) of bio F as the +1st base was selected by base sequence analysis. The plasmid thus obtained was named plasmid pSS201. Then, the plasmid pSS201 was cleaved with restriction enzymes Spe I and Pst I and the resulting DNA fragments were separated by agarose gel electrophoresis to prepare a DNA fragment containing 1408 bp in total from 201 bp upstream to a coding region of bio F to 46 bp downstream to the coding region, and having Spe I site introduced into the upstream end and a Pst I site introduced into the downstream end. The thus obtained DNA fragment was mixed with pSS207 cleaved by restriction enzymes Spe I and Pst I and these DNA fragments were ligated with each other by the use of a ligation kit (available from TAKARA SHUZO Co., Ltd.) according to the attached operating manual. The plasmid thus obtained was named pSS208.

Figure 8:
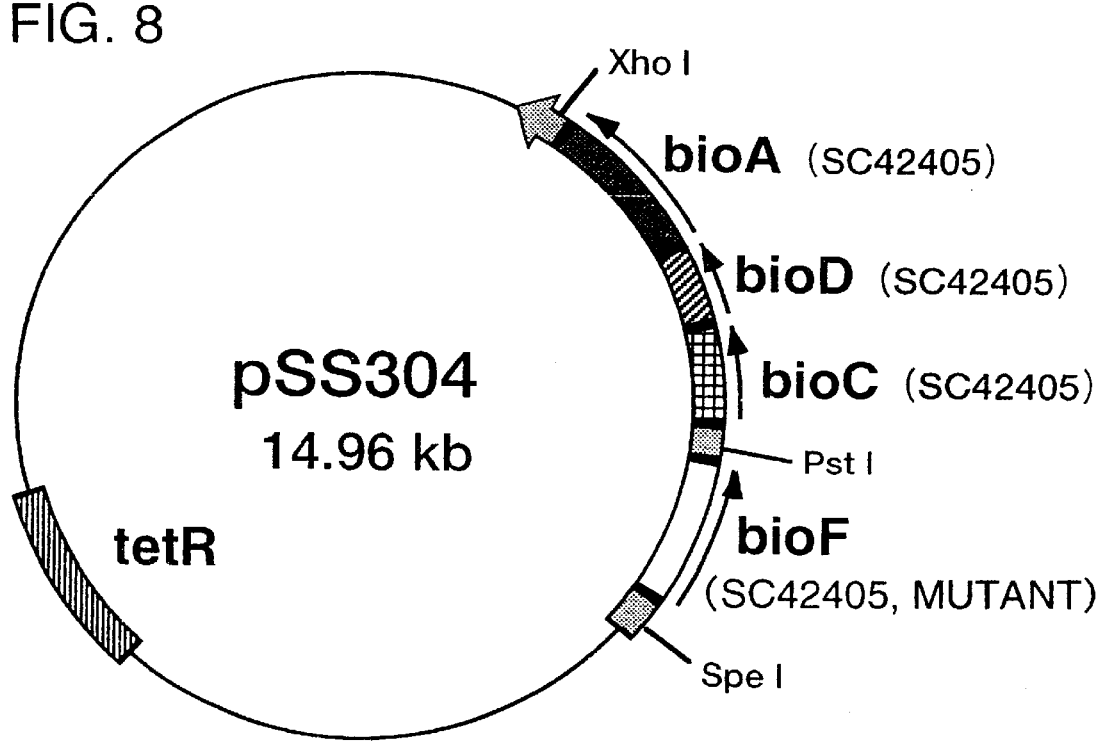
FIG. 8 shows the structure and restriction map of plasmid pSS304.

In addition, the plasmid pSS208 was cleaved with restriction enzymes Spe I and Xho I and the resulting DNA fragments were separated by agarose gel electrophoresis to prepare a DNA fragment containing mutant bio F as well as bio C, bio D and bio A and having Spe I site introduced into the upstream end and a Xho I site introduced into the downstream end. The thus obtained DNA fragment was mixed with pJAβ2 cleaved by restriction enzymes Spe I and Xho I and these DNA fragments were ligated with each other by the use of a ligation kit (available from TAKARA SHUZO Co., Ltd.) according to the attached operating manual. The plasmid thus obtained was named pSS304 (FIG. 8).

EXAMPLE 18

Preparation of Transformants Having pSS304 Introduced Thereinto and Transformants Having pSS305 Introduced Thereinto Sphingomonas sp. SC42405/pSS304 and Sphingomonas sp. SC42405/pSS305 were obtained by introducing the plasmid pSS304 obtained in Example 17 and the plasmid pSS305, respectively, into Sphingomonas sp. SC42405 with a gene pulser (mfd. by Bio-Rad Laboratories Inc.) by an electroporation method (applied voltage 18 kV/cm, capacitance 25 μF, resistance 400Ω).

EXAMPLE 19

Biotin Productivity and Biotin-related Substance Productivity of Sphingomonas sp. SC42405/pSS304 and Sphingomonas sp. SC42405/pSS305

A loopful of each of Sphingomonas sp. SC42405/pSS304 and Sphingomonas sp. SC42405/pSS305 was inoculated into a small test tube (18×150 mm) containing 3 ml of a culture medium (1% glycerol, 2% peptone, 0.15% $K_2HPO_4$, 0.15% $MgSO_4.7H_2O$, 0.005% tetracycline (pH 7.2)). As a control, a loopful of Sphingomonas sp. SC42405 having no gene introduced thereinto was inoculated into a small test tube (18×150 mm) containing 3 ml of a culture medium (1% glycerol, 2% peptone, 0.15% $K_2HPO_4$ 0.15% $MgSO_4.7H_2O$ (pH 7.2)). The above three kinds of the bacteria were cultured at 30° C. for 2 days (250 rpm) to obtain pre-culture broths. Then, 160 μl of each of the thus obtained pre-culture broths of Sphingomonas sp. SC42405/pSS304 and Sphingomonas sp. SC42405/pSS305 was inoculated into a large test tube (22×220 mm) containing 8 ml of a culture medium (6% glycerol), 2% yeast extract, 0.5% casamino acid, 0.1% $K_2HPO_4$, 0.05% KCl, 0.05% $MgSO_4.7H_2O$, 0.01% $FeSO_4.7H_2O$, 0.1% $MnSO_4.4$~$6H_2O$, 0.005% tetracycline (pH 7.0)). As a control, 160 μl of the pre-culture broth of Sphingomonas sp. SC42405 was inoculated into a large test tube (22×220 mm) containing 8 ml of a culture medium (6% glycerol, 2% yeast extract, 0.5% casamino acid, 0.1% $K_2HPO_4$, 0.05% KCl, 0.05% $MgSO_4.7H_2O$, 0.01% $FeSO_4.7H_2O$, 0.1% $MnSO_4.4$~$6H_2O$ (pH 7.0)). The above three kinds of the bacteria were cultured at 30° C. for 4 days (250 rpm). The concentrations of biotin and biotin-related compounds produced and accumulated in each culture broth were determined by the microbiological quantitation method (Izumi and Yamada "Vitaminological Experimental Method II. Water-soluble Vitamins", p. 481–499, Vitaminological Society of Japan, Tokyo Kagaku Dojin, 1985) by using *Lactobacillus plantarum* IFO 3070 strain and *Saccharomyces cerevisiae*, respectively. As a result, the concentrations of biotin and precursors in biotin biosynthesis, i.e., 7-keto-8-aminopelargonic acid, 7,8-diaminopelargonic acid and desthiobiotin (hereinafter referred to as "biotin-vitamers") were found to be as shown in Table 10.

TABLE 10

Biotin productivity and biotin-vitamer productivity of Sphingomonas sp. SC42405/pSS304 and Sphingomonas sp. SC42405/pSS305

| Strain | Biotin productivity* | Biotin concentration (mg/L) | Biotin-vitamer productivity* | Biotin-vitamer concentration |
|---|---|---|---|---|
| Sphingomonas sp. | 1 | 4.1 | 1 | 25.2 |
| Sphingomonas sp. SC42405/pSS304 | 0.9 | 3.5 | 11 | 271 |
| Sphingomonas sp. SC42405/pSS305 | 0.8 | 3.5 | 5.9 | 149 |

*Values relative to the biotin productivity of the strain having no gene introduced thereinto.

EXAMPLE 20

Preparation of a Recombinant Plasmid pSS306

Figure 9:
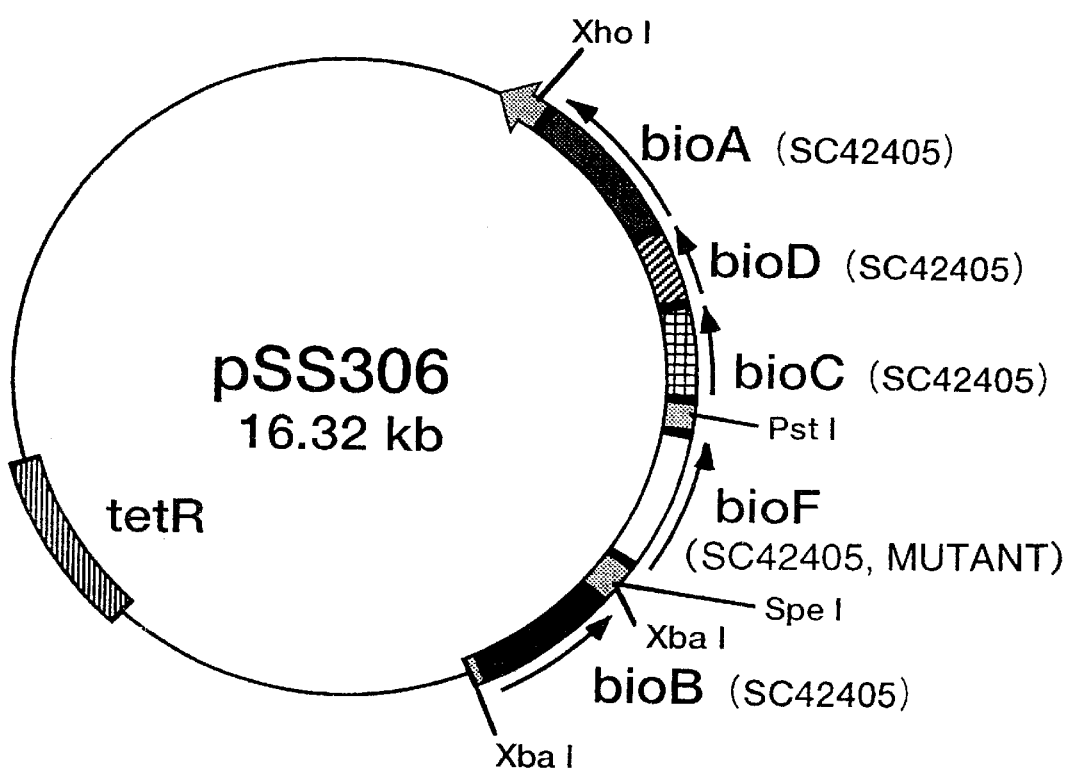
FIG. 9 shows the structure and restriction map of plasmid pSS306.

The plasmid pSS209 was cleaved with restriction enzymes Spe I and Xho I, and the resulting DNA fragments were separated by agarose electrophoresis to prepare a DNA fragment containing bio F, bio C, bio D and bio A and having a Spe I site introduced into the upstream end and a Xho I site introduced into the downstream end. The thus obtained DNA fragment was mixed with pSS301 cleaved by restriction enzymes Spe I and Xho I and these DNA fragments were ligated with each other by the use of a ligation kit (available from TAKARA SHUZO Co., Ltd.) according to the attached operating manual. The plasmid thus obtained was named pSS306 (FIG. 9).

EXAMPLE 21

Preparation of Transformants Having pSS306 Introduced Thereinto

Sphingomonas sp. SC42405/pSS306 was obtained by introducing the plasmid pSS306 obtained in Example 20 into Sphingomonas sp. SC42405 with a gene pulser (mfd. by Bio-Rad Laboratories Inc.) by an electroporation method (applied voltage 18 kV/cm, capacitance 25 μF, resistance 400Ω).

EXAMPLE 22

Biotin Productivity of Sphingomonas sp. SC42405/pSS306

A loopful of Sphingomonas sp. SC42405/pSS306 was inoculated into a small test tube (18×150 mm) containing 3 ml of a culture medium (1% glycerol, 2% peptone, 0.15% $K_2HPO_4$, 0.15% $MgSO_4.7H_2O$, 0.005% tetracycline (pH 7.2)). As a control, a loopful of Sphingomonas sp. SC42405 having no gene introduced thereinto was inoculated into a small test tube (18×150 mm) containing 3 ml of a culture medium (1% glycerol, 2% peptone, 0.15% $K_2HPO_4$ 0.15% $MgSO_4.7H_2O$ (pH 7.2)). The above two kinds of the bacteria were cultured at 30° C. for 2 days (250 rpm) to obtain pre-culture broths. Then, 160 μl of the thus obtained pre-culture broth of Sphingomonas sp. SC42405/pSS306 was inoculated into a large test tube (22×220 mm) containing 8 ml of a culture medium (6% glycerol, 2% yeast extract, 0.5% casamino acid, 0.1% $K_2HPO_4$, 0.05% KCl, 0.05% $MgSO_4.7H_2O$, 0.01% $FeSO_4.7H_2O$, 0.1% $MnSO_4.4~6H_2O$, 0.005% tetracycline (pH 7.0)). As a control, 160 μl of the pre-culture broth of Sphingomonas sp. SC42405 was inoculated into a large test tube (22×220 mm) containing 8 ml of a culture medium (6% glycerol, 2% yeast extract, 0.5% casamino acid, 0.1% $K_2HPO_4$, 0.05% KCl, 0.05% $MgSO_4.7H_2O$, 0.01% $FeSO_4.7H_2O$, 0.1% $MnSO_4.4~6H_2O$ (pH 7.0)). The above two kinds of the bacteria were cultured at 30° C. for 4 days (250 rpm). The concentrations of biotin and biotin-related compounds produced and accumulated in each culture broth were determined by the microbiological quantitation method (Izumi and Yamada "Vitaminological Experimental Method II. Water-soluble Vitamins", p. 481–499, Vitaminological Society of Japan, Tokyo Kagaku Dojin, 1985) by using *Lactobacillus plantarum* IFO 3070 strain and *Saccharomyces cerevisiae*, respectively. As a result, the concentrations of biotin produced were found to be as shown in Table 11.

TABLE 11

Biotin productivity of Sphingomonas sp. SC42405/pSS306

| Strain | Biotin productivity* | Biotin concentration |
|---|---|---|
| Sphingomonas sp. SC42405 | 1 | 4.1 |
| Sphingomonas sp. C42405/pSS306 | 3.9 | 16 |

*Values relative to the biotin productivity of the strain having no gene introduced thereinto.

INDUSTRIAL APPLICABILITY

The present invention provides a DNA fragment containing at least one gene concerned in biotin biosynthesis and derived from a microorganism belonging to the genus Sphingomonas, and biotin-producing transformants obtained by utilizing said DNA fragment, and is useful for improving the productivity of biotin, an essential vitamin for animals, plants and some microorganisms.

---

What is claimed is:

1. An isolated DNA, containing a gene for coding biotin synthase and derived from a microorganism belonging to genus Sphingomonas.

2. An isolated DNA containing a gene coding for a protein having the amino acid sequence shown as SEQ ID NO: 21, and having biotin synthase activity.

3. An isolated DNA containing a gene coding for a protein having the amino acid sequence shown as SEQ ID NO: 22, and having biotin synthase activity.

4. An isolated DNA containing a gene coding for a protein having the amino acid sequence shown as SEQ ID NO: 27, and having biotin synthase activity.

5. An isolated DNA containing a gene having the nucleotide sequence shown in SEQ ID NO: 23, 25 or 28, said gene coding for a protein having biotin synthase activity.

6. An isolated DNA, containing a gene expression regulatory region of a biotin synthase gene and derived from a microorganism belonging to genus Sphingomonas, wherein said biotin synthase gene comprises the gene expression regulatory region linked upstream to a region coding for biotin synthase.

7. An isolated DNA having the nucleotide sequence shown as SEQ ID NO: 36 or 37.

8. An isolated DNA according to any one of claims 1, and 6, wherein the microorganism belonging to the genus Sphingomonas is *Sphingomonas paucimobilis* JCM7511 or Sphingomonas sp. Sc42405.

9. A vector containing a DNA according to any one of claims 1 to 5, and 6 to 7.

10. A method for preparing a vector which comprises inserting a DNA according to any one of claims 1 to 5, and 6 to 7 to a vector replicable in host cells.

11. A vector comprising the gene expression regulatory region according to claim 6 and a region coding for a protein, wherein the gene expression regulatory region is linked upstream to the region coding for a protein.

12. A transformant having at least one DNA fragment according to claim 9.

13. A transformant according to claim 12, wherein the host cell is a microorganism.

14. A method for preparing transformants which comprises introducing a vector according to claim 9 into a host cell.

15. An isolated DNA containing a partial nucleotide sequence of a biotin synthase gene derived from a microorganism belonging to the genus Sphingomonas, wherein said partial nucleotide sequence contains a nucleotide sequence selected from SEQ ID No.: 38, 39, 40, 41, 44, and 45.

16. An isolated DNA, containing a gene coding a protein having the amino acid sequence as shown as SEQ ID NO: 21, 22 or 27, wherein said protein has biotin synthase activity.

17. An isolated DNA, containing at least one gene selected from:
  (a) a gene coding for a protein having biotin synthase activity and derived from a microorganism belonging to the genus Sphingomonas, wherein in said gene the region coding for said protein having biotin synthase activity has at least a 78% homology with the region coding for a protein in the nucleotide sequence shown as SEQ ID No.: 25 or 28; and
  (b) a gene coding for a protein having biotin synthase activity and derived from a microorganism belonging to the *Sphingomonas paucimobilis* JCM7511 or Sphingomonas sp. SC 42405, wherein in said gene the region coding for said protein having biotin synthase activity has at least a 78% homology with the region coding for a protein in the nucleotide sequence shown as SEQ ID No.: 25 or 28.

18. An isolated DNA, containing at least one gene selected from:
  (a) a gene coding for a protein having biotin synthase activity and derived from Sphingomonas, wherein the protein having biotin synthase activity has at least a 82% homology with the amino acid sequence shown as SEQ ID No.: 22 or 27; and
  (b) a gene coding for a protein having biotin synthase activity and derived from Sphingomonas paucimobilis JCM7511 or Sphingomonas sp. SC42405, wherein the protein having biotin synthase activity has at least a 82% homology with the amino acid sequence shown as SEQ ID No.: 22 or 27.

19. A vector containing a DNA according to claim 8.

20. A method for preparing a vector which comprises inserting a DNA according claim 8 to a vector replicable in host cells.

21. A transformant having at least one DNA fragment according claim 8 introduced into a host cell.

22. A transformant having at least one vector according to claim 9 introduced into a host cell.

23. A transformant having at least one vector according to claim 11 introduced into a host cell.

24. A method for preparing transformants which comprises introducing a vector according to claim 11 into a host cell.

* * * * *